United States Patent
Mooney et al.

(10) Patent No.: US 9,693,954 B2
(45) Date of Patent: Jul. 4, 2017

(54) CO-DELIVERY OF STIMULATORY AND INHIBITORY FACTORS TO CREATE TEMPORALLY STABLE AND SPATIALLY RESTRICTED ZONES

(75) Inventors: David J. Mooney, Sudbury, MA (US); William W. Yuen, Chicago, IL (US); Praveen Arany, Fairfax, VA (US)

(73) Assignee: President and Fellows of Harvard College, Cambridge, MA (US)

( * ) Notice: Subject to any disclaimer, the term of this patent is extended or adjusted under 35 U.S.C. 154(b) by 466 days.

(21) Appl. No.: 13/805,840

(22) PCT Filed: Jun. 27, 2011

(86) PCT No.: PCT/US2011/042051
§ 371 (c)(1),
(2), (4) Date: Jul. 31, 2013

(87) PCT Pub. No.: WO2011/163669
PCT Pub. Date: Dec. 29, 2011

(65) Prior Publication Data
US 2013/0302396 A1    Nov. 14, 2013

Related U.S. Application Data

(60) Provisional application No. 61/358,499, filed on Jun. 25, 2010.

(51) Int. Cl.
| | |
|---|---|
| A61K 38/18 | (2006.01) |
| A61K 39/395 | (2006.01) |
| A61K 31/33 | (2006.01) |
| A61K 35/28 | (2015.01) |
| A61K 35/54 | (2015.01) |
| A61P 19/02 | (2006.01) |
| A61K 9/00 | (2006.01) |
| A61F 2/30 | (2006.01) |
| A61K 45/06 | (2006.01) |
| A61K 35/545 | (2015.01) |
| A61K 31/16 | (2006.01) |
| A61K 31/335 | (2006.01) |
| A61K 31/381 | (2006.01) |
| A61K 31/4192 | (2006.01) |
| A61K 31/454 | (2006.01) |
| A61K 35/12 | (2015.01) |

(52) U.S. Cl.
CPC ........ *A61K 9/0087* (2013.01); *A61F 2/30756* (2013.01); *A61K 31/16* (2013.01); *A61K 31/335* (2013.01); *A61K 31/381* (2013.01); *A61K 31/4192* (2013.01); *A61K 31/454* (2013.01); *A61K 35/12* (2013.01); *A61K 35/28* (2013.01); *A61K 35/545* (2013.01); *A61K 38/185* (2013.01); *A61K 38/1808* (2013.01); *A61K 38/1841* (2013.01); *A61K 38/1866* (2013.01); *A61K 38/1875* (2013.01); *A61K 39/3955* (2013.01); *A61K 45/06* (2013.01); *A61F 2002/30766* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,522,811 | A | 6/1985 | Eppstein et al. |
| 4,946,778 | A | 8/1990 | Ladner et al. |
| 5,073,627 | A | 12/1991 | Curtis et al. |
| 5,091,513 | A | 2/1992 | Huston et al. |
| 5,132,405 | A | 7/1992 | Huston et al. |
| 5,885,829 | A | 3/1999 | Mooney et al. |
| 5,888,987 | A | 3/1999 | Haynes et al. |
| 6,129,716 | A | 10/2000 | Steer |
| 6,193,970 | B1 | 2/2001 | Pardoll et al. |
| 6,251,396 | B1 | 6/2001 | Gaur et al. |
| 6,281,256 | B1 | 8/2001 | Harris et al. |
| 6,334,968 | B1 | 1/2002 | Shapiro et al. |
| 6,403,374 | B1 | 6/2002 | Tsien et al. |
| 6,429,199 | B1 | 8/2002 | Krieg et al. |
| 6,511,650 | B1 | 1/2003 | Eiselt et al. |
| 6,541,022 | B1 | 4/2003 | Murphy et al. |
| 6,642,363 | B1 | 11/2003 | Mooney et al. |
| 6,685,963 | B1 | 2/2004 | Taupin et al. |
| 6,748,954 | B2 | 6/2004 | Lee et al. |
| 6,767,928 | B1 | 7/2004 | Murphy et al. |
| 6,783,712 | B2 | 8/2004 | Slivka et al. |
| 6,790,840 | B1 | 9/2004 | Lee et al. |
| 6,797,738 | B2 | 9/2004 | Harris et al. |
| 6,800,733 | B2 | 10/2004 | Tsien et al. |
| 7,157,566 | B2 | 1/2007 | Tsien et al. |
| 7,186,413 | B2 | 3/2007 | Bouhadir et al. |
| 7,192,693 | B2 | 3/2007 | Bryant et al. |
| 7,427,602 | B1 | 9/2008 | Shea et al. |
| 7,575,759 | B2 | 8/2009 | Murphy et al. |
| 7,790,699 | B2 | 9/2010 | Melvik et al. |
| 8,067,237 | B2 | 11/2011 | Mooney et al. |
| 8,188,058 | B2 | 5/2012 | Hackam et al. |
| 8,273,373 | B2 | 9/2012 | Alsberg et al. |
| 8,728,456 | B2 | 5/2014 | Sands et al. |
| 8,932,583 | B2 | 1/2015 | Mooney et al. |
| 2002/0131853 | A1 | 9/2002 | Nagasawa |
| 2002/0150604 | A1 | 10/2002 | Yi et al. |

(Continued)

FOREIGN PATENT DOCUMENTS

| | | |
|---|---|---|
| CN | 101655611 A | 2/2010 |
| EP | 0562862 A1 | 9/1993 |

(Continued)

OTHER PUBLICATIONS

"Wound Management: Past, Present, and Future." *Clinicians' Pocket Guide to Chronic Wound Repair*. Mulder et al., eds. Springhouse, PA: Springhouse Corporation. (1998):85-90.

(Continued)

*Primary Examiner* — Xiaozhen Xie
(74) *Attorney, Agent, or Firm* — McCarter & English, LLP; Maria Laccotripe Zacharakis

(57) ABSTRACT

The invention provides methods and compositions for local manipulation of regenerative processes via exogenous factor delivery.

38 Claims, 32 Drawing Sheets

(56) References Cited

U.S. PATENT DOCUMENTS

| | | |
|---|---|---|
| 2003/0075822 A1 | 4/2003 | Slivka et al. |
| 2003/0082806 A1 | 5/2003 | Berenson et al. |
| 2003/0095994 A1 | 5/2003 | Geistlich et al. |
| 2003/0100527 A1 | 5/2003 | Krieg et al. |
| 2003/0232895 A1 | 12/2003 | Omidian et al. |
| 2004/0058883 A1 | 3/2004 | Phillips et al. |
| 2004/0063206 A1 | 4/2004 | Rowley et al. |
| 2004/0136968 A1 | 7/2004 | Zheng et al. |
| 2004/0151764 A1 | 8/2004 | Zamora |
| 2004/0220111 A1 | 11/2004 | Kleinman et al. |
| 2004/0242469 A1 | 12/2004 | Lee et al. |
| 2004/0242482 A1 | 12/2004 | Gehring et al. |
| 2005/0002915 A1 | 1/2005 | Atala et al. |
| 2005/0053667 A1 | 3/2005 | Irvine et al. |
| 2005/0079159 A1 | 4/2005 | Shastri et al. |
| 2005/0090008 A1 | 4/2005 | Segura et al. |
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2006/0083712 A1 | 4/2006 | Anversa |
| 2006/0141018 A1 | 6/2006 | Cochrum et al. |
| 2006/0264380 A1 | 11/2006 | Hellstrom et al. |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0138416 A1 | 6/2008 | Rauh et al. |
| 2008/0206308 A1 | 8/2008 | Jabbari et al. |
| 2008/0268052 A1 | 10/2008 | Voytik-Harbin et al. |
| 2009/0017096 A1 | 1/2009 | Lowman et al. |
| 2009/0192079 A1 | 7/2009 | Santos et al. |
| 2009/0238853 A1 | 9/2009 | Liu et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0159008 A1 | 6/2010 | Barron et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0020216 A1 | 1/2011 | Mooney et al. |
| 2011/0117170 A1 | 5/2011 | Cao et al. |
| 2012/0100182 A1 | 4/2012 | Mooney et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |
| 2012/0329791 A1 | 12/2012 | Ashwell et al. |
| 2013/0029030 A1 | 1/2013 | Larsen |
| 2013/0177536 A1 | 7/2013 | Mooney et al. |
| 2013/0202707 A1 | 8/2013 | Ali et al. |
| 2013/0331343 A1 | 12/2013 | Cao et al. |
| 2014/0079752 A1 | 3/2014 | Huebsch et al. |
| 2014/0112990 A1 | 4/2014 | Bencherif et al. |
| 2014/0178964 A1 | 6/2014 | Mooney et al. |
| 2014/0193488 A1 | 7/2014 | Kim et al. |
| 2014/0227327 A1 | 8/2014 | Bencherif et al. |
| 2014/0234423 A1 | 8/2014 | Sands et al. |
| 2015/0024026 A1 | 1/2015 | Mooney et al. |

FOREIGN PATENT DOCUMENTS

| | | | |
|---|---|---|---|
| EP | 1452191 A2 | | 9/2004 |
| EP | 1561481 A2 | | 8/2005 |
| JP | 2005170816 A | | 6/2005 |
| WO | WO-9616086 A1 | | 5/1996 |
| WO | WO-9812228 A1 | | 3/1998 |
| WO | WO-9951259 A2 | | 10/1999 |
| WO | WO 01/35932 | * | 5/2001 |
| WO | WO-0135932 A2 | | 5/2001 |
| WO | WO-0216557 A2 | | 2/2002 |
| WO | WO-03020884 A2 | | 3/2003 |
| WO | WO-2004006990 A2 | | 1/2004 |
| WO | WO-2004030706 A2 | | 4/2004 |
| WO | WO-2004089413 A1 | | 10/2004 |
| WO | WO-2005026318 A2 | | 3/2005 |
| WO | WO-2005037190 A2 | | 4/2005 |
| WO | WO-2005037293 A1 | | 4/2005 |
| WO | WO-2005046748 A1 | | 5/2005 |
| WO | WO-2005072088 A2 | | 8/2005 |
| WO | WO 2006/092718 | * | 9/2006 |
| WO | WO-2006119619 A1 | | 11/2006 |
| WO | WO-2006136905 A2 | | 12/2006 |
| WO | WO-2007030901 A1 | | 3/2007 |
| WO | WO-2007064152 A1 | | 6/2007 |
| WO | WO-2007070660 A2 | | 6/2007 |
| WO | WO-2007078196 A1 | | 7/2007 |
| WO | WO-2007107739 A1 | | 9/2007 |
| WO | WO-2007150020 A1 | | 12/2007 |
| WO | WO-2008018707 A1 | | 2/2008 |
| WO | WO-2009002401 A2 | | 12/2008 |
| WO | WO-2009005769 A2 | | 1/2009 |
| WO | WO-2009074341 A1 | | 6/2009 |
| WO | WO-2009102465 A2 | | 8/2009 |
| WO | WO-2009146456 A1 | | 12/2009 |
| WO | WO-2009155583 A1 | | 12/2009 |
| WO | WO-2010120749 A2 | | 10/2010 |
| WO | WO-2011014871 A1 | | 2/2011 |
| WO | WO-2011063336 A2 | | 5/2011 |
| WO | WO-2011109834 A2 | | 9/2011 |
| WO | WO-2011130753 A2 | | 10/2011 |
| WO | WO-2011150240 A1 | | 12/2011 |
| WO | WO-2011151431 A1 | | 12/2011 |
| WO | WO-2012009611 A2 | | 1/2012 |
| WO | WO-2012019049 A1 | | 2/2012 |
| WO | WO-2012048165 A2 | | 4/2012 |
| WO | WO-2012064697 A2 | | 5/2012 |
| WO | WO-2012148684 A1 | | 11/2012 |
| WO | WO-2012149358 A1 | | 11/2012 |
| WO | WO-2012167230 A1 | | 12/2012 |
| WO | WO-2013106852 A1 | | 7/2013 |
| WO | WO-2013158673 A1 | | 10/2013 |

OTHER PUBLICATIONS

Anderson et al. "Biomaterial Microarrays: Rapid, Microscale Screening of Polymer-Cell Interaction." *Biomaterials.* 26.23(2005):4892-4897.

Anderson et al. "Nanoliter-Scale Synthesis of Arrayed Biomaterials and Application to Human Embryonic Stem Cell.s" *Nat. Biotechnol.* 22.7(2004):863-866.

Bar-Cohen et al. "Electroactive Polymer Actuators and Sensors." *MRS Bullet.* 33.3(2008):173-181.

Bates. "Improved Muscle Regeneration by Combining VEGF With IGF1." *Regen. Med.* 5.6(2010):853-854.

Beaucage et al. "The Functionalization of Oligonucleotides Via Phosphoramidite Derivatives." *Tetrahedron.* 49.10(1993):1925-1963.

Beebe et al. "Functional Hydrogel Structures for Autonomous Flow Control Inside Microfluidic Channels." *Nature.* 404(2000):588-590.

Bekiari et al. "Study of Poly(N,N-dimethylacrylamide)/CdS Nanocomposite Organic/Inorganic Gels." *Langmuir.* 20.19(2004):7972-7975.

Blumenthal et al. "Polyurethane Scaffolds Seeded with Genetically Engineered Skeletal Myoblasts: A Promising Tool to Regenerate Myocardial Function." *Artificial Organs.* 34.2(2010):E46-E54.

Calvert. "Electroactive Polymer Gels." *Electroactive Polymer (EAP) Actuators as Artificial Muscle: Reality, Potential, and Challenges.* Bar-Cohen, ed. Bellingham, WA: Spie Press. (2004):151-170.

Calvert. "Gel Sensors and Actuators." *MRS Bullet.* 33.3(2008):207-212.

(56) References Cited

OTHER PUBLICATIONS

Conconi et al. "In vitro and in vivo Evaluation of Acellular Diaphragmatic Matrices Seeded with Muscle Precursors Cells and Coated with VEGF Silica Gel to Repair Muscle Defect of the Diaphragm." *J. Biomed. Mater. Res.* 89A.2(2009):304-316.
Coulson et al. "Flow of Fluids through Granular Beds and Packed Columns." *Chemical Engineering*. New York: Pergamon Press. 2(1978):125-171.
Crameri et al. "Improved Green Fluorescent Protein by Molecular Evolution Using DNA Shuffling." *Nat. Biotechnol.* 14.3(1996):315-319.
Doan et al. "Subcellular Localizatino of a Sporulation Membrane Protein is Achieved Through a Network of Interactions Along and Across the Septum." *Mol. Microbiol.* 55.6(2005):1767-1781.
Egholm et al. "Peptide Nucleic Acids (PNA). Oligonucleotide Analogues with an Achiral Peptide Backbone." *J. Am. Chem. Soc.* 114.5(1992):1895-1897.
Egholm et al. "PNA Hybridizes to Complementary Oligonucleotides Obeying the Watson-Crick Hydrogen-Bonding Rules." *Nature.* 365.6446(1993):566-568.
Falsey et al. "Peptide and Small Molecule Microarray for High Throughput Cell Adhesion and Functional Assays." *Bioconjug. Chem.* 12.3(2001):346-353.
Fischer et al. "A Brilliant Monomeric Red Fluorescent Protein to Visualize Cytoskeleton Dynamics in *Dictyostelium*." *FEBS Lett.* 577.1-2(2004):227-232.
Fischer et al. "Visualizing Cytoskeleton Dynamics in Mammalian Cells Using a Humanized Variant of Monomeric Red Fluorescent Protein." *FEBS Lett.* 580.10(2006):2495-2502.
Fox. "Management of Worsening Multiple Sclerosis with Mitoxantrone: A Review." *Clin. Ther.* 28.4(2006):461-474.
GenBank Accession No. AAI44040, Mar. 18, 2009.
GenBank Accession No. CAG29322.1, Oct. 16, 2008.
GenBank Accession No. CAG33149.1, Oct. 21, 2008.
GenBank Accession No. EF064765.1, Nov. 13, 2006.
Glasbey et al. "Image Analysis and Three-Dimensional Modelling of Pores in Soil Aggregates." *Eur. J. Soil Sci.* 42.2(1991):479-486.
Gupta et al. "Magnetically Controlled Targeted Micro-Carrier Systems." *Life Sci.* 44.3(1989):175-186.
Heath. "Cells for Tissue Engineering." *Trends Biotechnol.* 18.1(2006):17-19.
Iwamoto et al. "Preparation of an Ionic Polymer Gel Microactuator and Measurement of its Periodic Motions." *Nippon Kagaku Kaishi.* 9(1997):609-614. (Japanese Orginal and English Abstract).
Juntanon et al. "Electrically Controlled Release of Sulfosalicylic Acid from Crosslinked Poly(Vinyl Alcohol)Hydrogel." *Int. J. Pharm.* 356(2008):1-11.
Kim et al. "The Effect of VEGF on the Myogenic Differentiation of Adipose Tissue Derived Stem Cells Within Thermosensitive Hydrogel Matrices." *Biomaterials.* 31.6(2010):1213-1218.
Kwon et al. "Electrically Erodible Polymer Gel for Controlled Release of Drugs." *Nature.* 354(1991):291-293.
Lao et al. "Magnetic and Hydrogel Composite Materials for Hyperthermia Applications." *J. Mater. Sci. Mater. Med.* 15.10(2004):1061-1064.
Letsinger et al. "Phosphoramidate Analogs of Oligonucleotides." *J. Org. Chem.* 35.11(1970):3800-3803.
Liu et al. "Nanostructured Materials Designed for Cell Binding and Transduction." *Biomacromolecules.* 2.2(2001):362-368.
López et al. "Magnetic Applications of Polymer Gels." *Macromol. Symp.* 166.1(2001):173-178.
Meier et al. "Peptide Nucleic Acids (PNAs)—Unusual Properties of Noionic Oligonucleotide Analogues." *Angew. Chem. Int. Ed.* 31.8(1992):1008-1010.
Meraz et al. "Mesoporous Silicon Particles for the Presentation of Tumor Antigens and Adjuvant for Anti-Cancer Immunity." *Cancer Res.* 71.S24(2011):159s-160s. (Abstract #P1-01-12).
Miyata et al. "Biomolecule-Sensitive Hydrogels." *Adv. Drug Deliv. Rev.* 54.1(2002):79-98.

Murdan. "Electro-Responsive Drug Deliverly from Hydrogels." *J. Control. Release.* 92(2003):1-17.
Nagai et al. "A Variant of Yellow Fluorescent Protein with Fast and Efficient Maturation for Cell-Biological Applications." *Nat. Biotechnol.* 20.1(2002):87-90.
NCBI Accession No. NM_004119, Apr. 14, 2013.
NCBI Accession No. NM_006274.2, Mar. 31, 2013.
Niamlang et al. "Electrically Controlled Release of Salicylic Acid from poly(p-phenylene vinylene) Polyacrylamide Hydrogels." *Int. J. Pharm.* 371(2009):126-133.
Orner et al. "Arrays for the Combinatorial Exploration of Cell Adhesion." *J. Am. Chem. Soc.* 126.35(2004):10808-10809.
Paradee et al. "Effects of Crosslinking Ratio, Model Drugs, and Electric Field Strength on Electrically Controlled Release for Alginate-Based Hydrogels." *J. Mater. Sci. Mater. Med.* 23(2012):999-1010.
Parker et al. "Effect of Mitoxantrone on Outcome of Children with First Relapse of Acute Lymphoblastic Leukemia (ALL R3): An Open-Label Radomised Trial." *Lancet.* 376(2010):2009-2017.
Porter et al. "Separation of Natural Populations of Coliform Bacteria from Freshwater and Sewage by Magnetic-Bead Cell Sorting." *J. Microbiol. Meth.* 33.3(1998):221-226.
Qui et al. "Environment-Sensitive Hydrogels for Drug Delivery." *Adv. Drug Deliv. Rev.* 53.3(2001):321-339.
Rhoads et al. "Satellite Cell-Mediated Angiogenesis in vitro Coincides with a Functional Hypoxia-Inducible Factor Pathway." *Am. J. Physiol. Cell Physiol.* 296.6(2009):C1321-C1328.
Rizzo et al. "An Improved Cyan Fluorescent Protein Variant Useful for FRET." *Nat. Biotechnol.* 22.4(2004):445-449.
Shaner et al. "Improved Monomeric Red, Orange and Yellow Fluorescent Proteins Derived from *Discosoma* sp. Red Fluorescent Protein." *Nat. Biotechnol.* 22.12(2004):1567-1572.
Takahashi et al. "Induction of Pluripotent Stem Cells from Adult Human Fibroblasts by Defined Factors." *Cell.* 131.5(2007):861-872.
Tanaka et al. "Collapse of Gels in an Electric Field." *Science.* 218(1982):467-469.
ten Dijke et al. "Growth Factors for Wound Healing." *Nat. Biotechnol.* 7(1989):793-798.
Tomer et al. "Electrically Controlled Release of Macromolecules from Cross-Linked Hyaluronic Acid Hydrogels." *J. Control. Release.* 33.3(1995):405-413.
Tourniaire et al. "Polymer Microarrays for Cellular Adhesion." *Chem. Commun.* 20(2006):2118-2120.
Tsien. "The Green Fluorescent Protein." *Annu. Rev. Biochem.* 67(1998):509-544.
Wang et al. "Evolution of New Nonantibody Proteins via Iterative Somatic Hypermutation." *PNAS.* 101.48(2004):16745-16749.
Xie et al. "Preparation and Application of Surface-Coated Superparamagnetic Nanobeads in the Isolation of Genomic DNA." *J. Magn. Magnetic Mater.* 277.1(2004):16-23.
Yu et al. "Induced Pluripotent Stem Cell Lines Derived from Human Somatic Cells." *Science.* 318-5858(2007):1917-1920.
Yuk et al. "Electric Current-Sensitive Drug Delivery System Using Sodium Alginate/Polyacrylic Acid Composites." *Pharm. Res.* 9.7(1992):955-957.
"Collagen: The Fibrous Proteins of the Matrix." *Molecular Cell Biology.* Lodish et al., eds. New York: W.H. Freeman. Section 22.3(2000):979-985.
"Transient." Merriam-Webster Dictionary. Web. Jul. 18, 2014. www.merriam-webster.com/dictionary/transient.
Agache et al."Mechanical Properties and Young's Modulus of Human Skin in Vivo." *Arch. Dermatol. Res.* 269.3(1980):221-232.
Aguado et al. "Improving Viability of Stem Cells During Syringe Needle Flow Through the Design of Hydrogel Cell Carriers." *Tissue Eng. Part A.* 18.7-8(2012):806-815.
Akpalo et al. "Fibrin-Polyethylene Oxide Interpenetrating Polymer Networks: New Self-Supported Biomaterials Combining the Properties of Both Protein Gel and Synthetic Polymer." *Acta Biomater.* 7.6(2011):2418-2427.
Alsberg et al. "Regulating Bone Formation via Controlled Scaffold Design." *J. Dent. Res.* 82.11(2003):903-908.

(56) References Cited

OTHER PUBLICATIONS

American Diabetes Association. "Standards of Medical Care in Diabetes—2013." *Diabetes Care*. 36.S1(2013):S11-S66.

Annaidh et al. "Characterization of the Anistropic Mechanical Properties of Excised Human Skin." *J. Mech. Behav. Biomed. Mater.* 5.1(2012):139-148.

Aschner et al. "Metabolic Memory for Vascular Disease in Diabetes." *Diabetes Technol. Ther.* 14.S1(2012):S68-S74.

Aubin et al. "Directed 3D Cell Alignment and Elongation in Microengineered Hydrogels." *Biomater*. 31.27(2010):6941-6951.

Augst et al. "Alginate Hydrogels as Biomaterials." *Macromol. Biosci.* 6(2006):623-633.

Babensee et al. "Host Response to Tissue Engineered Device." *Adv. Drug Deli. Rev.* 33.1-2(1998):111-139.

Bachem et al. "Superior Antigen Cross-Presentation and XCR1 Expression Define Human CD11c+CD141+ Cells as Homologues of Mouse CD8+ Dendritic Cells." *J. Exp. Med.* 207.6(2010):1273-1281.

Becker et al. "Cytological Demonstration of the Clonal Nature of Spleen Colonies Derived from Transplanted Mouse Marrow Cells." *Nature*. 197(1963):452-454.

Bell. "Models for the Specific Adhesion of Cells to Cells." *Science*. 200.4342(1978):618-627.

Bencherif et al. "Influence of Cross-Linker Chemistry on Release Kinetics of PEG-co-PGA Hydrogels." *J. Biomed. Mater. Res. A.* 90.1(2009):142-153.

Bencherif et al. "End-Group Effects on the Properties of PEG-co-PGA Hydrogels." *Acta Biomater.* 5.6(2009):1872-1883.

Bencherif et al. "Influence of the Degree of Methacrylation of Hyaluronic Acid Hydrogels Properties." *Biomater*. 29.12(2008):1739-1749.

Bencherif et al. "Injectable Preformed Scaffolds with Shape-Memory Properties." *PNAS*. 109.48(2012):19590-19595.

Bencherif et al. "Nanostructured Hybrid Hydrogels Prepared by a Combination of Atom Transfer Radical Polymerization and Free Radical Polymerization." *Biomater*. 30.29(2009):5270-5278.

Bencherif et al. "Synthesis by AFET ATRP of Degradable Nanogel Precursors for in situ Formation of Nanostructured Hyaluronic Acid Hydrogel." *Biomacromol*. 10.9(2009):2499-2507.

Benton et al. "Photocrosslinking of Gelatin Macromers to Synthesize Porous Hydrogels that Promote Valvular Interstitial Cell Function." *Tissue Eng. Part A*. 15.11(2009):3221-3230.

Berg et al. "IL-10 is a Central Regulator of Cyclooxygenase-2 Expression and Prostaglandin Production." *J. Immunol.* 166.4(2001):2674-2680.

Bergstraesser et al. "Stimulation and Inhibition of Human Mammary Epithelial Cell Duct Morphogenesis in Vitro." *Proc. Assoc. Am. Physicians*. 108.2(1996):140-154.

Bianco et al. "The Meaning, the Sense and the Significance: Translating the Science of Mesenchymal Stem Cells into Medicine." *Nat. Med.* 19.1(2013):35-42.

Bilodeau et al. "Regular Pyramid Punch Problem." *J. Appl. Mech.* 59.3(1992):519-523.

Boateng et al. "Wound Healing Dressings and Drug Delivery Systems: A Review." *J. Pharm. Sci.* 97.8(2008):2892-2923.

Boerckel et al. "Mechanical Regulation of Vascular Growth and Tissue Regeneration in vivo." *PNAS*. 108.37(2011):E674-E680.

Boontheekul et al. "Controlling Alginate Gel Degradation Utilizing Partial Oxidation and Bimodal Molecular Weight Distribution." *Biomaterials*. 26.15(2005):2455-2465.

Bouhadir et al. "Degradation of Partially Oxidized Alginate and its Potential Application for Tissue Engineering." *Biotechnol. Prog.* 17.5(2001):945-950.

Brignone et al. "A Phase I Phamacokinetic and Biological Correlative Study of IMP321, a Novel MHC Class II Agonist, in Patients with Advanced Renal Cell Carcinoma." *Clin. Cancer Res.* 15.19(2009):6225-6231.

Broxmeyer et al. "Insights into the Biology of Cord Blood Stem/Progenitor Cells." *Cell Prolif.* 44.S1(2011):55-59.

Bryant et al. "Photo-Patterning of Porous Hydrogels for Tissue Engineering." *Biomater*. 28.19(2007):2978-2986.

Buckwalter et al. "Form of Antigen Dictates Immunity: Irradiated Cell vs. Whole Cell Lysate Vaccination." *J. Immunol.* 178(2007).

Bullard et al. "Fetal Wound Healing: Current Biology." *World J. Surg.* 27.1(2003):54-61.

Buonaguro et al. "Translating Tumor Antigens into Cancer Vaccines." *Clin. Vaccine Immunol.* 18.1(2011):23-34.

Burdick et al. "Controlled Degradation and Mechanical Behavior of Photopolymerized Hyaluronic Acid Networks." *Biomacromol*. 6.1(2005):386-391.

Burdick et al. "Photoencapsulation of Osteoblasts in Injectable RGD-Modified PEG Hydrogels for Bone Tissue Engineering." *Biomater*. 23.22(2002):4315-4323.

Bégué et al. "Vaccination Against Human Papillomavirus. Implementation and Efficacy Against Cervical Cancer Control." *Bull. Acad. Natl. Med.* 191.9(2007):1805-1816. (French original and English abstract).

Bürger et al. "Effect of VEGF and its Receptor Antagonist SU-5416, an Inhibitor of Angiogenesis, on Processing of the β-amyloid Precursor Protein in Primary Neuronal Cells Derived From Brain Tissue of Tg2576 Mice." *Int. J. Dev. Neurosci.* 28.7(2010):597-604.

Cameron et al. "The Influence of Substrate Creep on Mesenchymal Stem Cell Behaviour and Phenotype." *Biomater*. 32.26(2011):5979-5993.

Caulfield et al. "Regulation of Major Histocompatibility Complex Class II Antigens on Human Alveolar Macrophages by Granulocyte-Macrophage Colony-Stimulating Factor in the Presence of Glucocorticoids." *Immunol.* 98.1(1999):104-110.

Ceriello et al. "The 'Metabolic Meory': Is more than just Tight Glucose Control Necessary to Prevent Diabetic Complications?" *J. Clin. Endocrinol. Metab.* 94.2(2009):410-415.

Ceriello et al. "The Emerging Challenge in Diabetes: The 'Metabolic Memory.'" *Vascular Pharmacol.* 57.5-6(2012):133-138.

Chan et al. "Traction Dynamics of Filopodia on Compliant Substrates." *Science*. 322.5908(2008):1687-1691.

Chang. "Mouse Models for Studies of Retinal Degeneration and Diseases." *Methods Mol. Biol.* 935(2013):27-39.

Chen et al. "Adipogenic Differentiation of Adipose Tissue-Derived Human Mesenchymal Stem Cells: Effects of Gastric Bypass Surgery." *Surg. Endosc.* 26(2012):3449-3456.

Chen et al. "Functional Human Vascular Network Generated in Photocrosslinkable Gelatin Methacrylate Hydrogels." *Adv. Funct. Mater*. 22.10(2012):2027-2039.

Chiang et al. "Whole Tumor Antigen Vaccines." *Semin. Immunol.* 22.3(2010):132-143.

Choi et al. "In Vitro Mineralization by Preosteoblasts in Poly(DL-lactide-co-glycolide) Inverse Opal Scaffolds Reinforced with Hydrozyapatite Nanoparticles." *Langmuir*. 26.14(2010):12126-12131.

Choi et al. "Three-Dimentional Scaffolds for Tissue Engineering: The Importance of Uniformity in Pore Size and Structure." *Langmuir*. 26.24(2010):19001-19006.

Chou et al. "Characterization of Photocross Linked Alginate Hydrogels for Nucleus Pulposus Cell Encapsulation." *J. Biomed. Mater. Res. A.* 91A.1(2009):187-194.

Clark et al. "Myosin II and Mechanotransduction: A Balancing Act." *Trends Cell Biol*. 17.4(2007):178-186.

Comisar et al. "Engineering RGD Nanopatterned Hydrogels to Control Preosteoblast Behavior: A Combined Computational and Experimental Approach." *Biomaterials*. 28(2007):4409-4417.

Cook et al. "A Sialomucopeptide Liberated by Trypsin from the Human Erythrocyte." *Nature* 188(1960):1011-1012.

Cooper. "Metabolic Memory: Implications for Diabetic Vascular Complications." *Pediatr. Diabetes.* 10.5(2009):343-346.

Cuda et al. "In Vitro Actin Filament Sliding Velocities Produced by Mixtures of Different Types of Myosin." *Biophys. J.* 72.4(1997):1767-1779.

Cukierman et al. "Taking Cell-Matrix Adhesions to the Third Dimension." *Science*. 294.5547(2001):1708-1712.

Dar et al. "Optimization of Cardiac Cell Seeding and Distribution in 3D Porous Alginate Scaffolds." *Biotechnol. Bioeng.* 80(2002):305-312.

(56) References Cited

OTHER PUBLICATIONS

David et al. "The in vitro Desensitization of Sensitive Cells by Trypsin." *J. Exp. Med.* 120(1964):1189-1200.
Davies et al. "Antibody-Antigen Complexes." *Annu. Rev. Biochem.* 59(1990):439-473.
de Jong et al. "Regulation of Notch Signaling Genes During BMP2-Induced Differentiation of Osteoblast Precursor Cells." *Biochem. Biophys. Res. Commun*.320(2004):100-107.
Dembo et al. "Stresses at the Cell-to-Substrate Interface During Locomotion of Fibroblasts." *Biophys. J.* 76.4(1999):2307-2316.
Dexter et al. "Conditions Controlling the Proliferation of Haemopoietic Stem Cells in Vitro." *J. Cell. Physiol.* 91.3(1977):335-344.
Di Nicola et al. "Human Bone Marrow Stromal Cells Suppress T-Lymphocyte Proliferation Induced by Cellular or Nonspecific Mitogenic Stimuli." *Blood.* 99.10(2002):3838-3843.
Diduch et al. "Two Cell Lines from Bone Marrow tht Differ in Terms of Collagen Synthesis, Osteogenic Characteristics, and Matrix Mineralization." *J. Bone Joint Surg. Am.* 75.1(1993):92-105.
Diridollou et al. "Skin Ageing: Changes of Physical Properties of Human Skin in vivo." *J. Cosmet. Sci.* 23.6(2001):353-362.
Discher et al. "Tissue Cells Feel and Respond to the Stiffness of their Substrate." *Science.* 310.5751(2005):1139-1143.
Disis et al. "Granulocyte-Macrophage Colony-Stimulating Factor: An Effective Adjuvant for Protein and Peptide-Based Vaccines." *Blood.* 88.1(1996):202-210.
Donati et al. "New Hypothesis on the Role of Alternating Sequences in Calcium-Alginate Gels." *Biomacromol.* 6.2(2005):1031-1040.
Douay et al. "Ex vivo Production of Human Red Blood Cells from Hematopoietic Stem Cells: What is the Future in Transfusion?" *Transfus. Med. Rev.* 21.2(2007):91-100.
Dranoff. "GM-CSF-Based Cancer Vaccines." *Immunol. Rev.* 188(2002):147-154.
DuFort et al. "Balancing Forces: Architectural Control of Mechanotransduction." *Nat. Rev. Mol. Cell Biol.* 12.5(2011):308-319.
Dupont et al. "Role of YAP/TAZ in Mechanotransduction." *Nature.* 474.7350(2011):179-183.
Edwards et al. "Evaluation of Biomechanical Properties of Human Skin." *Clin. Dermatol.* 13.4(1995):375-380.
Eming et al. "Inflammation in Wound Repair: Molecular and Cellular Mechanisms." *J. Invest. Dermatol.* 127.3(2007):514-525.
Engler et al. "Microtissue Elasticity: Measurements by Atomic Force Microscopy and its Influence on Cell Differentiation." *Methods Cell. Biol.* 83(2007):521-545.
Engler et al. "Substrate Compliance Versus Ligand Density in Cell on Gel Response." *Biophys. J.* 86.1 Pt1(2004):617-628.
Exposito et al. "The Fibrallar Collagen Family." *Int. J. Mol. Sci.* 11.2(2010):407-426.
Falanga. "Wound Healing and its Impairment in the Diabetic Foot." *Lancet.* 366.9498(2005):1736-1743.
Fauquemberque et al. "HLA-A*0201-Restricted CEA-Derived Peptide CAP1 is not a Suitable Target for T-Cell-Based Immunotherapy." *J. Immunother.* 33.4(2010):402-413.
Fisher et al. "The Study of Protein Mechanics with the Atomic Force Microscope." *Trends Biochem. Sci.* 24.10(1999):379-384.
Friedenstein et al. "Fibroblast Precursors in Normal and Irradiated Mouse Hematopoietic Organs." *Exp. Hematol.* 4.5(1976):267-274.
Gardel et al. "Traction Stress in Focal Adhesions Correlates Biphasically with Actin Retrograde Flow Speed." *J. Cell Biol.* 183.6(2008):999-1005.
Gasic et al. "Removal and Regeneration of the Cell Coating in Tumour Cells." *Nature.* 196(1962):170.
Gauthier et al. "Temporary Increase in Plasma Membrane Tension Coordinates the Activation of Exocytosis and Contraction During Cell Spreading." *PNAS.* 108.35(2011):14467-14472.
Geerligs et al. "Linear Viscoelastic Behavior of Subcutaneous Adipose Tissue." *Biorheol.* 45.6(2008):677-688.
GenBank Accession No. AAA36738.1, Aug. 3, 1993.
GenBank Accession No. AAA60022.1, Jan. 7, 1995.
GenBank Accession No. AAA64239.1, Mar. 23, 1995.
GenBank Accession No. AAB18786.3, Jul. 12, 1999.
GenBank Accession No. AAH94877.1, May 20, 2005.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01955.1, Nov. 14, 2006.
GenBank Accession No. DQ103757.1, Jul. 25, 2005.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_000091.4, May 10, 2014.
GenBank Accession No. NM_000572.2, May 18, 2014.
GenBank Accession No. NM_000638.3, May 4, 2014.
GenBank Accession No. NM_000758.3, May 4, 2014.
GenBank Accession No. NM_000885.4, Apr. 13, 2014.
GenBank Accession No. NM_000963.3, Jun. 13, 2014.
GenBank Accession No. NM_001001522.1, May 18, 2014.
GenBank Accession No. NM_001845.4, May 3, 2014.
GenBank Accession No. NM_001901.2, May 18, 2014.
GenBank Accession No. NM_002421.3_05112014.
GenBank Accession No. NM_002982.3, May 3, 2014.
GenBank Accession No. NM_003377.4, May 5, 2014.
GenBank Accession No. NM_003392.4, May 5, 2014.
GenBank Accession No. NM_004469.4, May 25, 2014.
GenBank Accession No. NM_005429.3, Mar. 31, 2014.
GenBank Accession No. NM_015719.3, Feb. 26, 2014.
GenBank Accession No. NP_000082.2, May 10, 2014.
GenBank Accession No. NP_000629.3, May 4, 2014.
GenBank Accession No. NP_000749.2, May 4, 2014.
GenBank Accession No. NP_000876.3, Apr. 13, 2014.
GenBank Accession No. NP_000954.1, Jun. 13, 2014.
GenBank Accession No. NP_001001522.1, May 18, 2014.
GenBank Accession No. NP_001836.2, May 3, 2014.
GenBank Accession No. NP_001892.1, May 18, 2014.
GenBank Accession No. NP_002973.1, May 3, 2014.
GenBank Accession No. NP_003239.2, Feb. 18, 2014.
GenBank Accession No. NP_003368.1, May 5, 2014.
GenBank Accession No. NP_003383.2, May 5, 2014.
GenBank Accession No. NP_004460.1, May 25, 2014.
GenBank Accession No. NP_005420.1, May 11, 2014.
GenBank Accession No. NP_056534.2, Feb. 26, 2014.
GenBank Accession No. U76381.2, Jul. 12, 1999.
Genes et al. "Effect of Substrate Mechanics on Chondrocyte Adhesion to Modified Alginate Surfaces." *Arch. Biochem. Biophys.* 422.2(2004):161-167.
Graessley. "Entangled Linear, Branched and Network Polymer Systems—Molecular Theories." *Adv. Poly. Sci.* 47(1982):67-117.
Guillaume et al. "Two Abundant Proteasome Subtypes that Uniquely Process Some Antigens Presented by HLA Class I Molecules." *PNAS.* 107.43(2010):18599-18604.
Guo et al. "Droplet Microfluidics for High-Throughput Biological Assays." *Lab Chip.* 12.12(2012):2146-2155.
Gurkan et al. "The Mechanical Environment of Bone Marrow: A Review." *Ann. Biomed. Eng.* 36.12(2008):1978-1991.
Halim et al. "Biologic and Synthetic Skin Substitutes: An Overview." *Indian J. Plast. Surg.* 43(2010):S23-S28.
Harris. "Classification, Diagnostic Criteria, and Screening for Diabetes." *Diabetes in America*. NIH Publication No. 95-1468. Chapter 2. (1995):15-36.
Holland et al. "Transforming Growth Factor-β1 Release from Oligo(poly(ethylene glycol) Fumarate) Hydrogels in Conditions that Model the Cartilage Wound Healing Environment." *J. Control. Release.* 94(2004):101-1 14.
Humphries et al. "Integrin Ligands at a Glance." *J. Cell. Sci.* 119.Pt19(2006):3901-3903.

(56) References Cited

OTHER PUBLICATIONS

Huston et al. "Protein Engineering of Antibody Binding Sites: Recovery of Specific Activity in an Anti-Digoxin Single-Chain Fv Analogue Produced in *Escherichia coli.*" *PNAS.* 85.16(1988):5879-5883.
Hutson et al. "Synthesis and Characterization of Tunable Poly(ethylene Glycol): Gelatin Methacrylate Composite Hydrogels." *Tissue Eng. Part A.* 17.13-14(2011):1713-1723.
Hwang et al. "Fabrication of Three-Dimensional Porous Cell-Laden Hydrogel for Tissue Engineering." *Biofabrication.* 2.3(2010):035003.
Ihnat et al. "Hypothesis: The 'Metabolic Memory', The New Challenge of Diabetes." *Diabet. Med.* 24.6(2007)582-586.
Isern et al. "Self-Renewing Human Bone Marrow Mesenspheres Promote Hematopoietic Stem Cell Expansion." *Cell Rep.* 3.5(2013):1714-1724.
Janmey et al. "From Tissue Mechanics to Transcription Factors." *Differentiation.* 86.3(2013):112-120.
Jiang et al. "Two-Piconewton Slip Bond Between Fibronectin and the Cytoskeleton Depends on Talin." *Nature.* 424.6946(2003):334-337.
Jokinen et al. "Integrin-Mediated Cell Adhesion to Type I Collagen Fibrils." *J. Biol. Chem.* 279.30(2004):31956-31963.
Jugdutt et al. "Aging and Defective Healing, Adverse Remodeling, and Blunted Post-Conditioning in the Reperfused Wounded Heart." . *Am. Coll. Cardiol.* 51.14(2008):1399-1403.
Kang et al. "Effect of Porous Structure on the Degradation of Freeze-Dried Gelatin Hydrogels." *J. Bioact. Compat. Poly.* 14.4(1999):331-343.
Katayama et al. "Integrated Analysis of the Genome and the Transcriptome by FANTOM." *Brief Bioinform.* 5.3(2004):249-258.
Kearney et al. "Macroscale Delivery Systems for Molecular and Cellular Payloads." *Nat. Mater.* 12.11(2013):1004-10017.
Kennedy et al. "Rapid and Extensive Collapse from Electrically Responsive Macroporous Hydrogels." *Adv. Healthc. Mater.* 3.4(2014):500-507.
Khetan et al. "Degradation-Mediated Cellular Traction Directs Stem Cell Fate in Covalently Crosslinked Three-Dimensional Hydrogels." *Nat. Mater.* 12.5(2013):458-465.
Kim et al. "Multifunctional Capsule-in-Capsules for Immunoprotection and Trimodal Imaging." *Angew. Chem. Int. Ed.* 50.10(2011):2317-2321.
Klein et al. "Cell-Cycle Control by Physiological Matrix Elasticity and in Viivo Tissue Stiffening." *Curr. Biol.* 19.18(2009):1511-1518.
Kohane. "Microparticles and Nanoparticles for Drug Delivery." *Biotechnol. Bioeng.* 96.2(2007):203-209.
Kong et al. "Controlling Degradation of Hydrogels via the Size of Crosslinked Junctions." *Adv. Mater.* 16.21(2004):1917-1921.
Kong et al. "Decoupling the Dependence of Rheological/Mechanical Properties of Hydrogels from Solids Concentration." *Polymer.* 43(2002):6239-6246.
Kong et al. "Design of Biodegradable Hydrogel for the Local and Sustained Delivery of Angiogenic Plasmid DNA." *Pharma. Res.* 25.5(2008):1230-1238.
Kong et al. "FRET Measurements of Cell-Traction Forces and Nano-Scale Clustering of Adhesion Ligands Varied by Substrate Stiffness." *PNAS.* 102.12(2005):4300-4305.
Kratky et al. "Direct Activation of Antigen-Presenting Cells is Required for CD8+ T-Cell Priming and Tumor Vaccination." *PNAS.* 108.42(2011):17414-17419.
Kuwahara et al. "Cell Delivery Using an Injectable and Adhesive Transglutaminase-Gelatin Gel." *Tissue Eng. Part C Methods.* 16.4(2010):609-618.
Langenkamp et al. "Kinetics of Dendritic Cell Activation: Impact on Priming of TH1, TH2 and Nonpolarized T Cells." *Nat. Immunol.* 1.4(2000):311-316.
Lauterbach et al. "Mouse CD8α+ DCs and Human BDCA3+ DCs are Major Producers of IFN-λ in Response to Poly IC." *J. Exp. Med.* 207.12(2010):2703-2717.
Lee et al. " Intravenous hMSCs Improve Myocardial Infarction in Mice because Cells Embolized in Lung are Activated to Secrete the Anti-Inflammatory Protein TSG-6." *Cell Stem Cell.* 5.1(2009):54-63.
Lee et al. "Engineering Liver Tissue Spheroids with Inverted Colloidal Crystal Scaffolds." *Biomater.* 30.27(2009):4687-4694.
Lele et al. "Investigating Complexity of Protein-Protein Interactions in Focal Adhesions." *Biochem. Biophys. Res. Commun.* 369.3(2008):929-934.
Leor et al. "Cells, Scaffolds, and Molecules for Myocardial Tissue Engineering." *Pharmacol. Therapeutics.* 105(2005):151-163.
Levental et al. "Soft Biological Materials and their Impact on Cell Function." *Soft Matter.* 3(2007):299-306.
Li et al. "A Novel Cyclohexene Derivate, Ethyl (6R)-6-[N-(2-Chloro-4-fluorophenyl)sulfamoyl]cyclohex-1-ene-1-carboxylate (TAK-242), Selectively Inhibits Toll-Like Receptor 4-Mediated Cytokine Production Through Suppression of Intracellular Signaling." *Mol. Pharmacol.* 69.4(2006):1288-1295.
Li et al. "Purified Hybrid Cells from Dendritic Cell and Tumor Cell Fusions are Superior Activators of Antitumor Immunity." *Cancer Immunol. Immunother.* 50.9(2001):456-462.
Lin et al. "Transdermal Regulation of Vascular Network Bioengineering Using a Photopolymerizable Methacrylated Gelatin Hydrogel." *Biomater.* 34.28(2013):6785-6796.
Liu et al. "Heterobifunctional Poly(Ethylene Glycol)-Tethered Bone Morphogenetic Protein-2-Stimulated Bone Marrow Mesenchymal Stromal Cell Differentiation and Osteogenesis." *Tissue Eng.* 13.5(2007):1113-1124.
Liu et al. "On the Viscoelastic Character of Liver Tissue: Experiments and Modelling of the Linear Behaviour." *Biorheol.* 37.3(2000):191-201.
Lo et al. "Cell Movement is Guided by the Rigidity of the Substrate." *Biophys. J.* 79.1(2000):144-152.
Ludewig et al. "Immunotherapy with Dendritic Cells Directed Against Tumor Antigens Shared with Normal Host Cells Results in Severe Autoimmune Disease." *J. Exp. Med.* 191.5(2000):795-804.
Lutolf et al. "Repair of Bone Defects Using Synthetic Mimetics of Collagenous Extracellular Matrices." *Nat. Biotechnol.* 21.5(2003):513-518.
Majeti et al. "Identification of a Hierarchy of Multipotent Hematopoietic Progenitors in Human Cord Blood." *Cell Stem Cell.* 1.6(2007):635-645.
Malmqvist. "Biospecific Interaction Analysis Using Biosensor Technology." *Nature.* 361.6408(1993):186-187.
Mammoto et al. "Mechanical Control of Tissue and Organ Development." *Development.* 137.9(2010):1407-1420.
Manavski et al. "Vascular Niche Controls Organ Regeneration." *Circ. Res.* 114.17(2014):1077-1079.
Mansoor et al. "Engineering T Cells for Cancer Therapy." *Br. J. Cancer.* 93.10(2005):1085-1091.
Marui et al. "Simultaneous Application of Basic Fibroblast Growth Factor and Hepatocyte Growth Factor to Enhance the Blood Vessels Formation." *J. Vasc. Surg.* 41.1(2005):82-90.
Masedunskas et al. "Role for the Actomyosin Complex in Regulated Exocytosis Revealed by Intravital Microscopy." *PNAS.* 108.33(2011):13552-13557.
McDonald et al. "Early Fracture Callus Displays a Smooth Muscle-Like Viscoelastic Properties Ex Viivo: Implications for Fracture Healing." *J. Orthop. Res.* 27.11(2009):1508-1513.
McKinnon et al. "Biophysically Defined and Cytocompatible Covalently Adaptable Networks as Viscoelastic 3D Cell Culture Systems." *Adv. Mater.* 26.6(2014):865-872.
McWhorter et al. "Modulation of Macrophage Phenotype by Cell Shape." *PNAS.* 1 10.43(2013):17253-17258.
Melief et al. "Immunotherapy of Established (Pre)Malignant Disease by Synthetic Long Peptide Vaccines." *Nat. Rev. Cancer.* 8(2008):351-360.
Merkel et al. "Using Mechanobiological Mimicry of Red Blood Cells to Extend Circulation Times of Hydrogel Microparticles." *PNAS.* 108.2(2011):586-591.
Metters et al. "Fundamental Studies of Biodegradable Hydrogels as Cartilage Replacement Materials." *Biomed. Sci. Instrum.* 35(1999):33-38.

(56) References Cited

OTHER PUBLICATIONS

Miljkovic et al. "Chondrogenesis, Bone Morphogenetic Protein-4 and Mesenchymal Stem Cells." *Osteoarthritis Cartilage.* 16(2008):1121-1130.
Miller et al. "Melanoma." *N. Engl. J. Med.* 355.1(2006):51-65.
Miralles et al. "Actin Dynamics Control SRF Activity by Regulation of its Coactivator MAL." *Cell.* 113.3(2003):329-342.
Mohan et al. "Novel Porous, Polysaccharide Scaffolds for Tissue Engineering Applications." *Trends Biomater. Artif. Organs.* 18.2(2005):219-224.
Molinari et al. "Modification of Surface Membrane Antigens by Trypsin." *Proc. Soc. Exp. Biol. Med.* 148.4(1975):991-994.
Molloy et al. "Movement and Force Produced by a Single Myosin Head." *Nature.* 378.6553(1995):209-212.
Mooney et al. "Cytoskeletal Filament Assembly and the Control of Cell Spreading and Function by Extracellular Matrix." *J. Cell Sci.* 108(1995):2311-2320.
Muralidharan-Chari et al. "ARF6-Regulated Shedding of Tumor Cell-Derived Plasma Membrane Microvesicles." *Curr. Biol.* 19.22(2009):1875-1885.
NCBI Accession No. NM_001561.5, Mar. 16, 2014.
NCBI Accession No. NM_004448.3, Apr. 23, 2014.
NCBI Accession No. NM_005018.2, Apr. 27, 2014.
NCBI Accession No. NM_181780.3, Jan. 27, 2014.
NCBI Accession No. Np_001193, May 3, 2014.
NCBI Accession No. NP_001552.2, Mar. 16, 2014.
NCBI Accession No. NP_003237.2, May 25, 2014.
NCBI Accession No. NP_003318.1, May 4, 2014.
NCBI Accession No. NP_003327.3, May 4, 2014.
NCBI Accession No. NP_005009.2, Apr. 27, 2014.
NCBI Accession No. NP_861445.3, Jan. 27, 2014.
Nichol et al. "Cell-Laden Microengineered Gelatin Methacrylate Hydrogels." *Biomater.* 31.21(2010):5536-5544.
Nicodemus et al. "Cell Encapsulation in Biodegradable Hydrogels for Tissue Engineering Applications." *Tissue Eng. Part B Rev.* 14.2(2008):149-165.
Niessen et al. "The $\alpha 6\beta 4$ Integrin is a Receptor for Both Lamin and Kalinin." *Exp. Cell Res.* 211.2(1994):360-367.
Ohashi et al. "Surgical Excision Combined with Autologous Whole Tumor Cell Vaccination is an Effective Therapy for Murine Neuroblastoma." *J. Ped. Surg.* 41(2006):1361-1368.
Osunkoya et al. "Synthesis and Fate of Immunological Surface Receptors on Cultured Burkitt Lymphoma Cells." *Int. J. Cancer.* 4.2(1969):159-165.
Page-McCaw et al. "Matrix Metalloproteinases and the Regulation of Tissue Remodelling." *Nat. Rev. Mol. Cell Biol.* 8.3(2007):221-233.
Pailler-Mattei et al. "In vivo Measurements of the Elastic Mechanical Properties of Human Skin by Indentation Tests." *Med. Eng. Phys.* 30.5(2008):599-606.
Pardoll. "The Blockade of Immune Checkpoints in Cancer Immunotherapy." *Nat. Rev. Cancer.* 12.4(2012):252-264.
Parekh et al. "Modulus-Driven Differentiation of Marrow Stromal Cells in 3D Scaffolds that is Independent of Myosin-Based Cytoskeletal Tension." *Biomater.* 32.9(2011):2256-2264.
Parekkadan et al. "Mesenchymal Stem Cell-Derived Molecules Reverse Fulminant Hepatic Failure." *PLoS One.* 2.9(2007):e941.
Park et al. "Photopolymerized Hyaluronic Acid-Based Hydrogels and Interpenetrating Networks." *Biomater.* 24.6(2003):893-900.
Pawlaczyk et al. "Age-Dependent Biomechanical Properties of the Skin." *Postepy. Dermatol. Alergol.* 30.5(2013):302-306.
Pedersen et al. "Induction of Regulatory Dendritic Cells by Desamethasone and $1\alpha,25$-Dihydroxyvitamin D3." *Immunol. Lett.* 91(2004):63-69.
Pek et al. "The Effect of Matrix Stiffness on Mesenchymal Stem Cell Differentiation in a 3D Thixotropic Gel." *Biomater.* 31.3(2010):385-391.

Pena et al. "Effects of TGF-$\beta$ and TGF-$\beta$ Neutralizing Antibodies on Fibroblast-Induced Collagen Gel Contraction: Implications for Proliferative Vitroretinpathy." *Invest. Ophthalmol. Vis. Sci.* 35.6(1994):2804-2808.
Peyton et al. "The Use of Poly(ethylene glycol) Hydrogels to Investigate the Impact of ECM Chemistry and Mechanics on Smooth Muscle Cells." *Biomater.* 27.28(2006):4881-4893.
Pinho et al. "PDGFR$\alpha$ and CD51 Mark Human Nestin+ Sphere-Forming Mesenchymal Stem Cells Capable of Hematopoietic Progenitor Cell Expansion." *J. Exp. Med.* 210.7(2013):1351-1367.
Qi et al. "Patterned Differentiation of Individual Embryoid Bodies in Spatially Organized 3D Hybrid Microgels." *Adv. Mater.* 22.46(2010):5276-5281.
Qin et al. "Soft Lithography for Micro- and Nanoscale Patterning." *Nat. Protoc.* 5.3(2010):491-502.
Raeber et al. "Molecularly Engineered PEG Hydrogels: A Novel Model System for Proteolyrically Mediated Cell Migration." *Biophys. J.* 89.2(2005):1374-1388.
Ramón-Azcón et al. "Gelatin Methacrylate as a Promising Hydrogel for 3D Microscale Organization and Proliferation of Dielectroretically Patterned Cells." *Lab on a Chip.* 12.16(2012):2959-2969.
Ranganath et al. "Harnessing the Mesenchymal Stem Cell Secretome for the Treatment of Cardiovascular Disease." *Cell Stem Cell.* 10.3(2012):244-258.
Raposo et al. "Extracellular Vesicles: Exosomes, Microvesicles, and Friends." *J. Cell. Biol.* 200.4(2013):373-383.
Reis e Sousa. "Activation of Dendritic Cells: Translating Innate into Adaptive Immunity." *Curr. Opin. Immunol.* 16.1(3005):21-25.
Roccaro et al. "BM Mesenchymal Stromal Cell-Derived Exosomes Facilitate Multiple Myeloma Progression." *J. Clin. Invest.* 123.4(2013):1542-1555.
Rodriguez et al. "Minimal "Self" Peptides that Inhibit Phagocytic Clearance and Enhance Delivery of Nanoparticles." *Science.* 339.6122(2013):971-975.
Sacchetti et al. "Self-Renewing Osteoprogenitors in Bone Marrow Sinusoids can Organize a Hematopoietic Microenvironment." *Cell.* 131.2(2007):324-336.
Sakai et al. "An Injectable, in situ Enzymatically Gellable, Gelatin Derivative for Drug Delivery and Tissue Engineering." *Biomater.* 30.20(2009):3371-3377.
Salem et al. "Defining the Antigen-Specific T-Cell Response to Vaccination and Poly(I:C)/TLR3 Signaling." *J. Immunother.* 28.3(2005):220-228.
Sarkar et al. "Condensation of Oligonucleotides Assembled into Nicked and Gapped Duplexes: Potential Structures for Oligonucleotide Delivery." *Nucleic Acids Res.* 33.1(2005):143-151.
Scheel et al. "Toll-Like Receptor-Dependent Activation of Several Human Blood Cell Types by Protamine Condensed mRNA." *Eur. J. Immunol.* 35(2005)1557-1566.
Schofield. "The Relationship Between the Spleen Colony-Forming Cell and the Haemopoietic Stem Cell." *Blood. Cells.* 4.1-2(1978):7-25.
Schwartz. "Integrins and Extracellular Matrix in Mechanotransduction." *Cold Spring Harb. Perspect. Biol.* 2.12(2010):a005066.
Sensi et al. "Unique Tumor Antigens: Evidence for Immune Control of Genome Integrity and Immunogenic Targets for T Cell-Mediated Patient-Specific Immunotherapy." *Clin. Cancer Res.* 12.17(2006):5023-5032.
Shi et al. "Granulocyte-Macrophage Colony-Stimulating Factor (GM-CSF) and T-Cell Responses: What we do and don't know." *Cell Res.* 16.2(2006):126-133.
Shin et al. "Contractile Forces Sustain and Polarize Hematopoiesis from Stem and Progenitor Cells." *Cell Stem Cell.* 14.1(2014):81-93.
Shin et al. "Lamins Regulate Cell Trafficking and Lineage Maturation of Adult Human Hematopoetic Cells." *PNAS.* 110.47(2013):18892-18897.
Shin et al. "Myonsin-II Inhibition and Soft 2D Matrix Maximize Multinucleation and Cellular Projections Typical of Platelet-Producing Megakaryocytes." *PNAS.* 108.28(2011):11458-11463.
Shoichet et al. "Stability of Hydrogels Used in Cell Encapsulation: An In Vitro Comparison of Alginate and Agarose." *Biotechnol. Bioeng.* 50(1996):374-381.

(56) References Cited

OTHER PUBLICATIONS

Siegwart et al. "Synthesis, Characterization, and in vitro Cell Culture Viability of Degradable Poly(N-isopropylacrylamide-co-5,6-benzo-2-methylene-1,3-dioxepane)-Based Polymers and Cross-linked Gels." *J. Biomed. Mater. Res. A*. 87.2(2008):345-358.
Silva et al. "Effects of VEGF Temporal and Spatial Presentation on Angiogenesis." *Biomaterials*. 31.6(2010):1235-1241.
Silva et al. "Material-Based Deployment Enhances Efficacy of Endothelial Progenitor Cells." *PNAS*. 105.38(2008):14347-14352.
Singer et al. "Cutaneous Wound Healing." *N. Engl. J. Med*. 341.10(1999):738-746.
Solon et al. "Fibroblast Adaptation and Stiffness Matching to Soft Elastic Substrates." *Biophys. J*. 93.12(2007):4453-4461.
Stachowiak et al. "Inverse Opal Hydrogel-Collagen Composite Scaffolds as a Supportive Microenvironment for Immune Cell Migration." *J. Biomed. Mater. Res*. 85A(2008):815-828.
Sun et al. "Biomimetic Interpenetrating Polymer Network Hydrogels Based on Methacrylated Alginate and Collagen for 3D Pre-Osteoblast Spreading and Osteogenic Differentiation." *Soft Matter*. 8(2012):2398-2404.
Sun et al. "Highly Stretchable and Tough Hydrogels." *Nature*. 489.7414(2012):133-136.
Suri et al. "Photopatterned Collagen-Hyaluronic Acid Interpenetrating Polymer Network Hydrogels." *Acta Biomater*. 5.7(2009):2385-2397.
Swift et al. "Nuclear Lamin-A Scales with Tissue Stiffness and Enhances Matrix-Directed Differentiation." *Science*. 341.6149(2013):1240104.
Syed et al. "Stem Cell Therapy Market." *Nat. Rev. Drug Discov*. 12.3(2013):185-186.
Tabata et al. "Enhanced Vascularization and Tissue Granulation by Basic Fibroblast Growth Factor Impregnated in Gelatin Hydrogels." *J. Control. Release*. 31.2(1994):189-199.
Tannous. "*Gaussia* Luciferase Reporter Assay for Monitoring Biological Processes in Culture and in vivo." *Nat. Protoc*. 4.4(2009):582-591.
Thomas et al. "Intravenous Infusion of Bone Marrow in Patients Receiving Radiation and Chemotherapy." *N. Engl. J. Med*. 257.11(1957):491-496.
Thurner et al. "Vaccination with Mage-3A1 Peptide-Pulsed Mature, Monocyte-Derived Dendritic Cells Expands Specific Cytotoxic T Cells Induces Regression of Some Metastases in Advanced Stage IV Melanoma." *J. Exp. Med*. 190.11(1999):1669-1678.
Tong et al. "Engineering Interpenetrating Network Hydrogels as Biomimetic Cell Niche with Independently Tunable Biochemical and Mechanical Properties." *Biomater*. 35.6(2014):1807-1815.
Trappmann et al. "Extracelluar-Matrix Tethering Regulates Stem-Cell Fate." *Nat. Mater*. 11.7(2012):642-649.
Trappmann et al. "How Cells Sense Extracellular Matrix Stiffness: A Material's Perspective." *Curr. Opin. Biotechnol*. 24.5(2013):948-953.
Ugarte et al. "Notch Signaling Enhances Osteogenic Differentiation While Inhibiting Adipogenesis in Primary Human Bone Marrow Stromal Cells." *Exp. Hematol*. 37(2009):867-875.
Uhlenbruck. "Action of Proteolytic Enzymes on the Human Erythrocyte Surface." *Nature*. 190(1961):181.
Ulrich et al. "Probing Cellular Mechanobiology in Three-Dimensional Culture with Collagen-Agarose Matrices." *Biomater*. 31.7(2010):1875-1884.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
van der Bruggen et al. "T Cell-Defined Tumor Antigens." *Cancer Immunity*. (2013). Http:www.cancerimmunity.org/peptide.
Venturoni et al. "Investigations into the Polymorphism of Rat Tail Tendon Fibrils Using Atomic Force Microscopy." *Biochem. Biophys. Res. Commun*. 303.2(2003):508-513.
Vincent et al. "Stem Cell Differentiation: Post-Degradation Forces Kick in." *Nat. Mater*. 12.5(2013):384-386.
Vogel et al. "Local Force and Geometry Sensing Regulate Cell Functions." *Nat. Rev. Mol. Cell Biol*. 7.4(2006):265-275.
Wang et al. "Mechanotransduction at a Distance: Mechanically Coupling the Extracellular Matric with the Nucleus." *Nat. Rev. Mol. Cell. Biol*. 10.1(2009):75-82.
Wang-Gillam et al. "A Phase I Study of IMP321 and Gemcitabine as the Front-Line Therapy in Patients with Advanced Pancreatic Adenocarcinoma." *Invest. New Drugs*. 31.3(2013):707-713.
Warner et al. "Cyclooxygenases: New Forms, New Inhibitors, and Lessons from the Clinic." *FASEB J*. 18.7(2004):790-804.
Weisenberger et al. "Comprehensive DNA Methylation Analysis on the Illumina® Infinium® Assay Platform." Illumina, Inc. Mar. 25, 2008. Web.
Weiss et al. "The Demonstration of Rupture of Cell Surfaces by an Immunological Technique." *Exp. Cell Res*. 30(1963):331-338.
Wen et al. "Mechanically Robust Gelatin-Alginate IPN Hydrogels by a Combination of Enzymatic and Ionic Crosslinking Approaches." *Macromol. Mater. Eng*. 299(2013):504-513.
Wieland et al. "Engineering Molecular Circuits Using Synthetic Biology in Mammalian Cells." *Annu. Rev. Chem. Biomol. Eng*. 3(2012):209-234.
Wipff et al. "Myofibroblast Contraction Activates Latent TGF-β1 from the Extracellular Matrix." *J. Cell Biol*. 179.6(2007):1311-1323.
Wong et al. "Focal Adhesion Kinase Links Mechanical Force to Skin Fibrosis via Inflammatory Signaling." *Nat. Med*. 18.1(2011):148-152.
Wong et al. "Mechanical Force Prolongs Acute Inflammation via T-Cell-Dependent Pathways During Scar Formation." *FASEB. J*. 25.12(201 1):4498-4510.
Wong et al. "Pushing Back: Wound Mechanotransduction in Repair and Regeneration." *J. Invest. Dermatol*. 131.11(2011):2186-2196.
Wozniak et al. "Mechanotransduction in Development: A Growing Role for Contractility." *Nat. Rev. Mol. Cell Biol*. 10.1(2009):34-43.
Yeung et al. "Effects of Substrate Stiffness on Cell Morphology, Cytoskeletal Structure, and Adhesion." *Cell Motif. Cytoskeleton*. 60.1(2005):24-34.
Yoo et al. "Bio-Inspired, Bioengineered and Biomimetic Drug Delivery Carriers." *Nat. Rev. Drug Discov*. 10.7(2011):521-535.
Yoon. "Hidden Markov Models and their Applications in Biological Sequene Analysis." *Curr. Genomics*. 10.6(2009):402-415.
Young et al. "Gelatin as a Delivery Vehicle for the Controlled Release of Bioactive Molecules." *J. Control. Release*. 109.1-3(2005):256-274.
Zemel et al. "Optimal Matrix Rigiditiy for Stress Fibre Polarization in Stem Cells." *Nat. Phys*. 6.6(2010):468-473.
Zhang et al. "A Tension-Induced Mechanostransduction Pathway Promotes Epithelial Morphogenesis." *Nature*. 471.7336(2011):99-103.
Zhang et al. "Talin Depletion Reveals Independence of Initial Cell Spreading from Integrin Activation and Traction." *Nat. Cell Biol*. 10.9(2008):1062-1068.
Zhao et al. "Stress-Relaxation Behavior in Gels with Ionic and Covalent Crosslinks." *J. Appl. Phys*. 107.6(2010):63509.

(56) References Cited

OTHER PUBLICATIONS

Yang, Fan et al., "The effect of incorporating RGD adhesive peptide in polyethylene glycol diacrylate hydrogel on osteogenesis of bone marrow stromal cells," *Biomaterials*, vol. 26(2005):5991-5998.
"Antigens and Receptors." *Immunology*. Doan et al., eds. Philadelphia: Wolters Kluwer/Lippincott Williams & Wilsons. (2008):11-23.
Abrahams et al. "Expression and Secretion of Antiviral Factors by Trophoblast Cells Following Stimulation by the TLF-3 Agonist, Poly (I:C)." *Hum. Reprod.* 21.9(2006):2432-2439.
Agrawal et al. "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos." *J. Immunol.* 171.10(2003):4984-4989.
Akira et al. "Pathogen Recognition and Innate Immunity." *Cell.* 124.4(2006):783-801.
Akira et al. "Toll-Like Receptors: Critical Proteins Linking Innate and Acquired Immunity." *Nat. Immunol.* 2.8(2001):675-680.
Aldhous. "Print Me a Heart and a Set of Arteries." *New Scientist.* 2547(2006):19.
Ali et al. "Controlled Local Delivery of GM-CSF From Polymer-Based Vaccines Enhances Anti-Tumor Immune Responses by Priming Host Dendritic Cells." *2007 AACR Annual Meeting.* 48(2007):652. (Abstract #2736).
Ali et al. "Converging Cell Therapy with Biomaterials." *Cell Transplantation from Laboratory to Clinic.* Burlington, MA: Elsevier, Inc. (2006):591-609.
Ali et al. "In situ Regulation of DC Subsets and T Cells Mediates Tumor Regression in Mice." *Sci. Transl. Med.* 1.8(2009):8-19.
Ali et al. "Infection-Mimicking Materials to Program Dendritic Cells in situ." *Nat. Mater.* 8.2(2009):151-158.
Ali et al. "Sustained GM-CSF and PEI Condensed pDNA Presentation Increases the Level and Duration of Gene Expression in Dendritic Cells." *J. Control. Release.* 132.3(2008):273-278.
Allen et al. "Regulation of Satellite Cells During Skeletal Muscle Growth and Development." *Proc. Soc. Exp. Biol. Med.* 194.2(1990):81-86.
Allen et al. "Regulation of Skeletal Muscle Satellite Cell Proliferation by Bovine Pituitary Fibroblast Growth Factor." *Exp. Cell Res.* 152.1(1984):154-160.
Almarza et al. "Evaluation of Three Growth Factors in Combination of Two for Temporomandibular Joint Disc Tissue Engineering." *Arch. Oral Biol.* 51.3(2006):215-221.
Alsberg et al. "Cell-Interactive Alginate Hydrogels for Bone Tissue Engineering." *J. Dent. Res.* 80.11(2001):2025-2029.
Alsberg et al. "Engineering Growing Tissues." *PNAS.* 99.18(2002):12025-12030.
Anderson et al. "The NOD Mouse: A Model of Immune Dysregulation." *Annu. Rev. Immunol.* 23(2005):447-485.
Anderson. "A Role for Nitric Oxide in Muscle Repair: Nitric Oxide-Mediated Activation of Muscle Satellite Cells." *Mol. Biol. Cell.* 11(2000):1859-1874.
Arany et al. "At the Edge of Translation—Materials to Program Cells for Directed Differentiation." *Oral Dis.* 17.3(2011):241-251.
Atala et al. "Endoscopic Treatment of Vesicoureteral Reflux with a Chondrocyte-Alginate Suspension." *J. Urol.* 152(1994):641-643.
Bachelder et al. "Acid-Degradable Polyurethane Particles for Protein-Based Vaccines: Biological Evaluation and in Vitro Analysis of Particle Degradation Products." *Mol. Pharm.* 5.5(2008):876-884.
Badovinac et al. "Regulation of CD8 T+ Cells Undergoing Primary and Secondary Responses to Infection in the Same Host." *J. Immunol.* 170(2003):4933-4942.
Bakri et al. "Pharmacokinetics of Intravitreal Bevacizumab (Avastin)." *Ophthalmology.* 114.5(2007):855-859.
Balakrishna et al. "Structural Correlates of Antibacterial and Membrane-Permeabilizing Activities in Acylpolyamines." *Antimicrob. Agents Chemother*50.3(2006):852-861.
Banchereau et al. "Dendritic Cells and the Control of Immunity." *Nature.* 392.6673(1998):245-52.
Bar-Or et al. "Induction of Antigen-Specific Tolerance in Multiple Sclerosis after Immunization with DNA Encoding Myelin Basic Protein in a Randomized, Placebo-Controlled Phase 1/2 Trial." *Arch. Neurol.* 64.10(2007):1407-1415.
Barbero et al. "Growth Factor Supplemented Matrigel Improves Ectopic Skeletal Muscle Formation—A Cell Therapy Approach." *J. Cell. Physiol.* 186(2001):183-192.
Barrio et al. "A Two-Dimensional Numerical Study of Spatial Pattern Formation in Interacting Turing Systems." *Bull. Math Biol.* 61.3(1999):483-505.
Beauchamp et al. "Dynamics of Myoblast Transplantation Reveal a Discrete Minority of Precursors with Stem Cell-Like Properties as the Myogenic Source." *J. Cell Biol.* 144.6(1999):1113-1122.
Bischoff. "Proliferation of Muscle Satellite Cells on Intact Myofibers in Culture." *Dev. Biol.* 115.1(1986):129-139.
Blanes et al. "Induction of Autoimmune Diabetes by Oral Administration of Autoantigen." *Science.* 274.5293(1996):1707-1709.
Bohl et al. "Role of Synthetic Extracellular Matrix in Development of Engineered Dental Pulp." *J. Biomater. Sci. Polym. Ed.* 9.7(1998):749-764.
Bonauer et al. "MicroRNA-92a Controls Angiogenesis and Functional Recovery of Ischemic Tissues in Mice." *Science.* 324.5935(2009):1710-1713.
Boontheekul et al. "Regulating Myoblast Phenotype Through Controlled Gel Stiffness and Degradation." *Tissue Engin.* 13.7(2007):1431-1442.
Borselli et al. "Functional Muscle Regeneration with Combined Delivery of Angiogenesis and Myogenesis Factors." *PNAS.* 107.8(2010):3287-3292.
Bouhadir et al. "Synthesis of Cross-Linked Poly(aldehyde guluronate) Hydrogels." *Polymer.* 40(1999):3575-3584.
Bowne et al. "Injection of DNA Encoding Granulocyte-Macrophage Colony-Stimulating Factor Recruits Dendritic Cells for Immune Adjuvant Effects." *Cytokines Cell Mol. Ther.* 5.4(1999):217-225.
Brinkman et al. "Photo-Cross Linking of Type 1 Collagen Gels in the Presence of Smooth Muscle Cells: Mechanical Properties, Cell Viability, and Function." *Biomacromolecules.* 4.4(2003):890-895.
Brinkmann et al. "Neutrophil Extracellular Traps Kill Bacteria." *Science.* 303.5663(2004):1532-1535.
Brouwers et al. "Can the Growth Factors PTHrP, Ihh and VEGF, Together Regulate the Development of a Long Bone?" *J. Biomech.* 39.15(2006):2774-2782.
Burdick et al. "Stimulation of Neurite Outgrowth by Neurotrophins Delivered From Degradable Hydrogels." *Biomater.* 27.3(2006):452-459.
Cao et al. "Promoting Angiogenesis via Manipulation of VEGF Responsiveness with Notch Signaling." *Biomater.* 30.25(2009):4085-4093.
Carlson et al. "Notch Signaling Pathway and Tissue Engineering." *Front. Biosci.* 12(2007):5143-5156.
Carmeliet et al. "Angiogenesis in Cancer and Other Diseases." *Nature.* 407.6801(2000):249-257.
Carmeliet. "Mechanisms of Angiogenesis and Arteriogenesis." *Nat. Med.* 6.3(2000):389-395.
Chan et al. "Antifibrotic Effects of Suramin in Injured Skeletal Muscle After Laceration." *J. Appl. Physiol.* 95(2003):771-780.
Chan et al. "Helix Induction in Antimicrobial Peptides by Alginate in Biofilms." *J. Biol. Chem.* 279.37(2004):38749-38754.
Chen et al. "Integrated Approach to Designing Growth Factor Delivery Systems." *FASEB J.* 21.14(2007):3896-3903.
Chen et al. "Polymeric Growth Factor Delivery Strategies for Tissue Engineering." *Pharm. Res.* 20.8(2003):1103-1112.
Chen et al. "Skeletal Muscle Stem Cells." *Reprod. Biol. Endocrinol.* 1(2003):101.
Chen et al. "Spatio-Temporal VEGF and PDGF Delivery Patterns Blood Vessel Formation and Maturation." *Pharm. Res.* 24.2(2007):258-264.
Choi. "Replacement Organs, Hot Off the Press." *New Scientist.* 177.2379(2003):16.
Chromiak et al. "Bioreactor Perfusion System for the Long-Term Maintenance of Tissue-Engineered Skeletal Muscle Organoids." *In Vitro Cell Dev. Biol. Anim.* 34.9(1998):694-703.

(56) References Cited

OTHER PUBLICATIONS

Clauss et al. "Interstitial Transport of Rabbit and Sheep Antibodies in Normal and Neoplastic Tissues." *Cancer Res.* 50.12(1990):3487-3492.
Cohen et al. "Controlled Delivery Systems for Proteins Based on Poly(Lactic/Glycolic Acid) Microspheres." *Pharm. Res.* 8.6(1991):713-720.
Conboy et al. "The Regulation of Notch Signaling Controls Satellite Cell Activation and Cell Fate Determination in Postnatal Myogenesis." *Dev. Cell.* 3.3(2002):397-409.
Conn et al. "Purification of a Glycoprotein Vascular Endothelial Cell Mitogen from a Rat Glioma-Derived Cell Line." *PNAS.* 87.4(1990):1323-1327.
Cooper et al. "Extended Amplification In Vitro and Replicative Senescence: Key Factors Implicated in the Success of Human Myoblast Transplantation." *Hum. Gene Ther.* 14(2003):1169-1179.
Cornelison et al. "Single-Cell Analysis of Regulatory Gene Expression in Quiescent and Activated Mouse Skeletal Muscle Satellite Cells." *Dev. Biol.* 191.2(1997):270-283.
Cornelison et al. "Syndecan-3 and Syndecan-4 Specifically Mark Skeletal Muscle Satellite Cells and are Implicated in Satellite Cell Maintenance and Muscle Regeneration." *Dev. Biol.* 239.1(2001):79-94.
Cullen et al. "Investigation of Vascular Endothelial Growth Factor Effects on Pulmonary Endothelial Monolayer Permeability and Neutrophil Transmigration." *Gen. Pharmacol.* 35.3(2000):149-157.
Curiel et al. "Tumor Immunotherapy: Inching Toward the Finish Line." *J. Clin. Invest.* 109.3(2002):311-312.
D'Amico et al. "The Early Progenitors of Mouse Dendritic Cells and Plasmacytoid Predendritic Cells are within the Bone Marrow Hemopoietic Precursors Expressing Flt3." *J. Exp. Med.* 198.2(2003):293-303.
Daro et al. "Polyethylene Glycomodified GM-CSF Expands CD11bhighCD11chigh but not CD11blowCD11chigh Murine Dendritic Cells In Vivo: A Comparative Analysis with Flt3 Ligand." *J. Immunol.* 165.1(2000):49-58.
De Temmerman et al. "Particulate Vaccines: On the Quest for Optimal Delivery and Immune Response." *Drug Disc. Today.* 16.13/14(2011):569-582.
den Haan et al. "CD8+ by not CD8- Dendritic Cells Cross-Prime Cytotoxic T Cells in Vivo." *J. Exp. Med.* 192.12(2000):1685-1696.
Dennis et al. "Excitability and Contractility of Skeletal Muscle Engineered From Primary Cultures and Cell Lines." *Am. J. Physiol. Cell Physiol.* 280(2001):C288-C295.
Dennis et al. "Excitability and Isometric Contractile Properties of Mammalian Skeletal Muscle Constructs Engineered in vitro." *In Vitro Cell Dev. Biol. Anim.* 36.5(2000):327-335.
Dieu et al. "Selective Recruitment of Immature and Mature Dendritic Cells by Distinct Chemokines Expressed in Different Anatomic Sites." *J. Exp. Med.* 188.2(1988):373-386.
Dor et al. "Making Vascular Networks in the Adult: Branching Morphogenesis Without a Roadmap." *Trends Cell Biol.* 13.3(2003):131-136.
Dranoff et al. "Vaccination with Irradiated Tumor Cells Engineered to Secrete Murine Granulocyte-Macrophage Colony-Stimulating Factor Stimulates Potent, Specific and Long-Lasting Anti-Tumor Immunity." *PNAS.* 90.8(1993):3539-3543.
Dranoff. "Cyotkines in Cancer Pathogenesis and Cancer Therapy." *Nat. Rev. Cancer.* 4.1(2004):11-22.
Dudley et al. "Adoptive Cell Transfer Therapy Following Non-Myeloablative by Lymphodepleting Chemotherapy for the Treatment of Patients with Refractory Metastatic Melanoma." *J. Clin. Oncol.* 23.10(2005):2346-2357.
Ehrbar et al. "Endothelial Cell Proliferation and Progenitor Maturation by Fibrin-Bound VEGF Variants with Differential Susceptibilities to Local Cellular Activity." *J. Control. Release.* 101(2004):93-109.
Eiselt et al. "Porous Carriers for Biomedical Applications Based on Alginate Hydrogels." *Biomat.* 21.19(2000):1921-1927.
El-Backly et al. "Regeneration of Dentine/Pulp-Like Tissue Using a Dental Pulp Stem Cell/Poly(lactic-co-glycolic) Acid Scaffold Construct in New Zealand White Rabbits." *Aust. Endod. J.* 34.2(2008):52-67.
Eldar et al. "Elucidating Mechanisms Underlying Robustness of Morphogen Gradients." *Curr. Opin. Genet. Dev.* 14.4(2004):435-439.
Eldar et al. "Robustness of the BMP Morphogen Gradient in *Drosophila* Embryonic Patterning." *Nature.* 419.6904(2002):304-308.
Eldar et al. "Self-Enhanced Ligand Degradation Underlies Robustness of Morphogen Gradients." *Dev. Cell.* 5.4(2003):635-646.
Engler et al. "Matrix Elasticity Directs Stem Cell Lingeage Specification." *Cell.* 126.4(2006):677-689.
Ennett et al. "Temporally Regulated Delivery of VEGF in vitro and in vivo." *J. Biomed. Mater. Res. A.* 79.1(2006):176-184.
Faissner et al. "Boundaries and Inhibitory Molecules in Developing Neural Tissues." *Glia.* 13.4(1995):233-254.
Farrar et al. "T Helper Subset Development: Roles of Instruction, Selection, and Transcription." *J. Clin. Invest.* 109.4(2002):431-435.
Ferrara et al. "Angiogenesis as a Therapeutic Target." *Nature.* 438.7070(2005):967-974.
Ferrara et al. "Discovery and Development of Bevacizumab, an Anti-VEGF Antibody for Treating Cancer." *Nat. Rev. Drug Discov.* 3.5(2004):391-400.
Folkman. "Angiogenesis." *Annu. Rev. Med.* 57(2006):1-18.
Fonseca et al. "Capitalizing on the Immunogenicity of Dying Tumor Cells." *Clin. Cancer Res.* 14.16(2008):1603-1608.
Fontaine et al. "Surgical Treatment of Peripheral Circulation Disorders." *Helv. Chir. Acta.* 21.56(1954):499-533. (German Original, no. English Translation Available).
Friedrich et al. "Promoter Traps in Embryonic Stem Cells: A Genetic Screen to Identify and Mutate Developmental Genes in Mice." *Genes Dev.* 5(1991):1513-1523.
Fukushima et al. "The Use of an Antifibrosis Agent to Improve Muscle Recovery After Laceration." *Am. J. Sports Med.* 29.4(2001):394-402.
Gamvrellis et al. "Vaccines that Facilitate Antigen Entry into Dendritic Cells." *Immunol. Cell Biol.* 82(2004):506-516.
GenBank Accession No. A32848.1, Jul. 5, 2002.
GenBank Accession No. AAA35789.1, Apr. 27, 1993.
GenBank Accession No. AAA56738.1, Dec. 7, 1994.
GenBank Accession No. AAA60552.1, Nov. 24, 2003.
GenBank Accession No. AAA64297.1, Mar. 24, 1995.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. ABC86910, Jan. 3, 2011.
GenBank Accession No. CAA01954.1, Jun. 15, 1995.
GenBank Accession No. CAA40093.1, Oct. 7, 2008.
GenBank Accession No. CAA62632.1, Sep. 15, 1995.
GenBank Accession No. CAG46721.1, Jun. 29, 2004.
GenBank Accession No. CBI71013.1, Feb. 2, 2010.
GenBank Accession No. EU826563.1, Jul. 23, 2008.
GenBank Accession No. NM_000230.2, Dec. 17, 2012.
GenBank Accession No. NM_000514.3, Aug. 19, 2012.
GenBank Accession No. NM_000601.4, Nov. 25, 2012.
GenBank Accession No. NM_000614.3, Sep. 9, 2012.
GenBank Accession No. NM_000660.4, Dec. 9, 2012.
GenBank Accession No. NM_000800.3, Mar. 4, 2012.
GenBank Accession No. NM_001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_002506.2, Dec. 9, 2012.
GenBank Accession No. NM_002632.4, May 4, 2011.
GenBank Accession No. NM_003236.2, Aug. 21, 2011.
GenBank Accession No. NM_003263.3, Jan. 5, 2013.

(56) References Cited

OTHER PUBLICATIONS

GenBank Accession No. NM_003264.3, Jan. 6, 2013.
GenBank Accession No. NM_003268.5, Nov. 25, 2012.
GenBank Accession No. NM_006068.4, Oct. 28, 2012.
GenBank Accession No. NM_016562.3, Jan. 6, 2013.
GenBank Accession No. NM_030956.3, Oct. 28, 2012.
GenBank Accession No. NM_033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.
GenBank Accession No. NM_205820.1, Jan. 5, 2013.
GenBank Accession No. NM_205823.2, Jan. 6, 2013.
GenBank Accession No. NP_001096124.1, Dec. 16, 2012.
GenBank Accession No. NP_002010.2, Dec. 9, 2012.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_006059.2, Oct. 28, 2012.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
Gerhardt et al. "VEGF Guides Angiogenic Sprouting Utilizing Endothelial Tip Cell Filopodia." *J. Cell Biol.* 161.6(2003):1163-1177.
Gilboa. "Dendritic-Cell Based Cancer Vaccines." *J. Clin. Invest.* 117.5(2007):1195-1203.
Gnjatic et al. "Toll-Like Receptor Agonists: Are They Good Adjuvants?" *Cancer J.* 16.4(2010):382-391.
Godbey et al. "Size Matters: Molecular Weight Affects the Efficiency of Poly(ethylenimine) as a Gene Delivery Vehicle." *J. Biomed. Mater. Res.* 45.3(1999):268-275.
Godbey et al. "Tracking the Intracellular Path of Poly(ethylenimine)/DNA Complexes for Gene Delivery." *PNAS.* 96.9(1999):5177-5181.
Gospodarowicz et al. "Effect of Fibroblast Growth Factor on the Division and Fusion of Bovine Myoblasts." *J. Cell Biol.* 70.2(1976):395-405.
Griffith et al. "Tissue Engineering—Current Challenges and Expanding Opportunities." *Science.* 295(2002):1009-1014.
Grimmer et al. "Tracheal Reconstruction Using Tissue-Engineered Cartilage." *Arch. Otolaryngot Head Neck Surg.*130.10(2004):1191-1196.
Gros et al. "A Common Somitic Origin for Embryonic Muscle Progenitors and Satellite Cells." *Nature.* 435(2005):954-958.
Gullberg et al. "Extracellular Matrix and Its Receptors During Development." *Int. J. Dev. Biol.* 39(1995):845-854.
Gussoni et al. "Dystophin Expression and in the mdx Mouse Restored by Stem Cell Transplantation." *Nature.* 401(1999):390-394.
Hamby et al. "Small Molecule Inhibitors of Tumor-Promoted Angiogenesis, Including Protein Tyrosine Kinase Inhibitors." *Pharmacol. Ther.* 82.2-3(1999):169-193.
Hamdy et al. "Targeting Dendritic Cells with Nano-Particulate PLGA Cancer Vaccine Formulations." *Adv. Drug Deliv. Rev.* 63.10(2011):943-955.
Hamilton et al. "GM-CSF Biology." *Growth Factors.* 22.4(2004):225-231.
Hamilton. "GM-CSF in Inflammation and Autoimmunity." *Trends Immunol.* 23.8(2002):403-408.
Hanada. "Efficacy of Rehabilitative Therapy in Regional Musculoskeletal Conditions." *Best Pract. Res. Clin. Rheumatol.* 17.1(2003):151-166.
Hansen et al. "Comparison of Clinical Grade Type 1 Polarized and Standard Matured Dendritic Cells for Cancer Immunotherapy." *Vaccine.* 31.4(2013):639-646.
Hansen et al. "Integrin Binding and Cell Spreading on Extracellular Matrix Act at Different Points in the Cell Cycle to Promote Hepatocyte Growth." *Mol. Biol. Cell.* 5(1994):967-975.
Harris et al. "Open Pore Biodegradable Matrices Formed with Gas Foaming." *J. Biomed. Mater. Res.* 42.3(1998):396-402.
Harrison. "What is the Status of Reaction-Diffusion Theory Thirty-Four Years After Turing?" *J. Theor. Biol.* 125.4(1987):369-384.
Hartgerink et al. "Peptide-Amphiphile Nanofibers: A Versatile Scaffold for the Preparation of Self-Assembling Materials." *PNAS.* 99.8(2002):5133-5138.
Hartmann et al. "CpG DNA: A Potent Signal for Growth, Activation, and Maturation of Human Dendritic Cells." *PNAS.* 96(1999):9305-9310.
Hashimoto et al. "Development of Alginate Wound Dressings Linked with Hybrid Peptides Derived from Laminin and Elastin." *Biomaterials.* 25.7-8(2004):1407-1414.
Hawke et al. "Myogenic Satellite Cells: Physiology to Molecular Biology." *J. Appl. Physiol.* 91(2001):534-551.
Helm et al. "Synergy Between Interstitial Flow and VEGF Directs Capillary Morphogenesis in vitro Through a Gradient Amplification Mechanism." *PNAS.* 102.44(2005):15779-15784.
Henry et al. "The VIVA Trial: Vascular Endothelial Growth Factor in Ischemia for Vascular Angiogenesis." *Circulation.* 107.10(2003):1359-1365.
Hermanson. *Bioconjugate Techniques.* New York: Academic Press. (1996):152-185.
Heslop et al. "Transplanted Primary Neonatal Myoblasts Can Give Rise to Functional Satellite Cells as Identified Using the Myf5nlacZI+ Mouse." *Gene Ther.* 8(2001):778-783.
Hildner et al. "Batf3 Deficiency Reveals a Critical Role for CD8α+ Dendritic Cells in Cytotoxic T Cell Immunity." *Science.* 322.5904(2008):1097-1100.
Hill et al. "Designing Scaffolds to Enhance Transplanted Myoblast Survival and Migration." *Tissue Engin.* 12.5(2006):1295-1304.
Hill et al. "Muscle Satellite (Stem) Cell Activation During Local Tissue Injury and Repair." *J. Anat.* 203.1(2003):89-99.
Hill. "Macroporous Scaffold Architecture, Peptide, HGF/FGF and Myoblast Incorporation Enhance Myogenesis." *IADR/AADR/CADR 83rd General Session.* (Mar. 9-12, 2005). Poster #2829.
Hirano et al. "Peptide and Protein Presenting Materials for Tissue Engineering." *Adv. Mat.* 16.1(2004):17-25.
Hodge-Dufour et al. "Inhibition of Interferon γ Induced Interleukin 12 Production: A Potential Mechanism for the Anti-Inflammatory Activities of Tumor Necrosis Factor." *PNAS.* 95.23(1998):13806-13811.
Hodi et al. "Immunologic and Clinical Effects of Antibody Blockade of Cytotoxic T Lymphocyte-Associated Antigen 4 in Previously Vaccinated Cancer Patients." *PNAS.* 105.8(2008):3005-3010.
Horsley et al. "IL-4 Acts as a Myoblast Recruitment Factor During Mammalian Muscle Growth." *Cell.* 113.4(2003):483-494.
Hsiong et al. "Differentiation Stage Alters Matrix Control of Stem Cells." *J. Biomed. Mater. Res. Part A.* 8(2007):145-156.
Huang et al. "Fabrication and in vitro Testing of Polymeric Delivery Systems for Condensed DNA." *J. Biomed. Mater. Res.* 67(2003):1384-1392.
Huang et al. "Long-Term In Vivo Gene Expression via Delivery of PEI-DNA Condensates From Porous Polymer Scaffolds." *Hum. Gene Ther.* 16.5(2005):609-617.
Hubbell et al. "Materials Engineering for Immunomodulation." *Nature.* 462(2009):449-460.
Hubbell. "Biomaterials in Tissue Engineering." *Bio/Tech.* 13(1995):565-576.
Huebsch et al. "Harnessing Traction-Mediated Manipulation of the Cell/Matrix Interface to Control Stem-Cell Fate." *Nat. Mater.* 9.6(2010):518-526.
Ishihara et al. "Roles of Bradykinin in Vascular Permeability and Angiogenesis in Solid Tumor." *Int. Immunopharmacol.* 2.4(2002):499-509.
Jain. "Molecular Regulation of Vessel Maturation." *Nat. Med.* 9.6(2003):685-693.

(56) References Cited

OTHER PUBLICATIONS

Jain. "The Manufacturing Techniques of Various Drug Loaded Biodegradable Poly(lactide-co -glycolide) (PLGA) Devices." *Biomater.* 21.23(2000):2475-2490.
Jankovic et al. "In the Absence of IL-12, CD4+ T Cell Responses to Intracellular Pathogens Fail to Default to a Th2 Pattern and are Host Protective in an IL-10-/-Setting." *Immunity.* 16.3(2002):429-439.
Jego et al. "Plasmacytoid Dendritic Cells Induce Plasma Cell Differenetiation Through Type I Interferon and Interleukin 6." *Immunity.* 19.2(2003):225-234.
Jiang et al. "Self-Organization of Periodic Patterns by Dissociated Feather Mesenchymal Cells and the Regulation of Size, Number and Spacing of Primorida." *Development.* 126.22(1999):4997-5009.
Jinushi et al. "Enhancing the Clinical Activity of Granulocyte-Macrophage Colony-Stimulating Factor-Secreting Tumor Cell Vaccines." *Immunol. Rev.* 222(2008):287-298.
Jinushi et al. "MFG-E8-Mediated Uptake of Apoptotic Cells by APCs Links the Pro- and Antiinflammatory Activities of GM-CSF." *J. Clin. Invest.* 117.7(2007):1902-1913.
Johnson et al. "Activation of Skeletal Muscle Satellite Cells and the Role of Fibroblast Growth Factor Receptors." *Exp. Cell Res.* 219.2(1995):449-453.
Kanzler et al. "Therapeutic Targeting of Innate Immunity with Toll-Like Receptor Agaonists and Antagonists." *Nat. Med.* 13.5(2007):552-559.
Kawai et al. "Innate Immune Recognition of Viral Infection." *Nat. Immunol.* 7.2(2006):131-137.
Kawashima et al. "Pulmonary Delivery of Insulin With Nebulized DL-Lactide/Glycolide Copolymer (PLGA) Nanospheres to Prolong Hypoglycemic Effect." *J. Control. Release.* 62.1-2(1999):279-287.
Khownium et al. "Novel Endotoxin-Compounds with Terephthalaldehyde-bis-guanylhydrazone Scaffolds." *Bioorg. Med. Chem. Lett.* 16(2006):1305-1308.
Kim et al. "An Overview of Cartilage Tissue Engineering." *Yonsei Med. J.* 41.6(2000):766-773.
Kinoshita et al. "Successive Injections in MDX Mice of Myoblasts Grown with bFGF." *Neuromusc. Disord.* 6.3(1996):187-193.
Kisak et al. "The Vesosome—A Multicompartment Drug Delivery Vehicle." *Curr. Med. Chem.* 11.2(2004):199-219.
Klebanoff et al. "CD8+ T-Cell Memory in Tumor Immunology and Immunotherapy." *Immunol. Rev.* 211(2006):214-224.
Klinman. "Immunotherapeutic Uses of CpG Oligodeoxynucleotides." *Nat. Rev. Immunol.* 4.4(2004):249-258.
Kondo et al. "A Reaction-Diffusion Wave on the Skin of the Marine Angelfish *Pomacanthus.*" *Nature.* 376(2002):765-768.
Kong et al. "Controlling Rigidity and Degradation of Alginate Hydrogels via Molecular Weight Distribution." *Biomacromolec.* 5.5(2004):1720-1727.
Kong et al. "Designing Alginate Hydrogels to Maintain Viability of Immobilized Cells." *Biomat.* 24.22(2003):4023-4029.
Kong et al. "Non-Viral Gene Delivery Regulated by Stiffness of Cell Adhesion Substrates." *Nat. Mater.* 4(2005):406-410.
Krieg. "Development of TLR9 Agonists for Cancer Therapy." *J. Clin. Invest.* 117.5(2007):1184-1194.
Krishnamachari et al. "PLGA Microparticles that Co-Deliver Antigen and Toll Like Receptor Ligand Adjuvants for Applications in Cancer Immunotherapy." AAPS Pharmaceutica. Nov. 11, 2009. Web. Mar. 1, 2013. http://abstracts.aapspharmaceutica.com/ExpoAAPS09/CC/forms/attendee/index.aspx?content=sessionInfo&sessionId=2716.
Kumamoto et al. "Induction of Tumor-Specific Protective Immunity by in situ Langerhans Cell Vaccine." *Nat. BioTechnol.* 20.1(2002):64-69.
Kumar et al. "Toll-Like Receptors and Innate Immunity." *Biochem. Biophys. Res. Commun.* 388.4(2009):621-625.
Kurts et al. "CD8 T Cell Ignorance or Tolerance to Islet Antigens Depends on Antigen Dose." *PNAS.* 96.22(1999):12703-12707.
Kwon et al. "In vivo Targeting Dendritic Cells for Activation of Cellular Immunity Using Vaccine Carriers Based on pH-Responsive Microparticles." *PNAS.* 102.51(2005):18264-18268.
Langer et al. "Tissue Engineering." *Science.* 260(1993):920-926.
Lanzavecchia et al. "Regulation of T Cell Immunity by Dendritic Cells." *Cell.* 106.3(2001):263-266.
Leach et al. "Coating of VEGF-Releasing Scaffolds with Bioactive Glass for Angiogenesis and Bone Regeneration." *Biomater.* 27.17(2006):3249-3255.
Lee et al. "Hydrogel Formation via Vell Crosslinking." *Adv. Mat.* 15.21(2003):1828-1832.
Lee et al. "Hydrogels for Tissue Engineering." *Chem. Rev.* 101. 7(2001):1869-1879.
Lefaucheur et al. "The Cellular Events of Injured Muscle Regeneration Depend on the Nature of the Injury." *Neuromusc. Disorders.* 5.6(1995):501-509.
Lensch et al. "Scientific and Clinical Opportunities for Modeling Blood Disorders With Embyronic Stem Cells." *Blood.* 107. 7(2006):2605-2612.
Leshem et al. "Hepatocyte Growth Factor (HGF) Inhibits Skeletal Muscle Cell Differentiation: A Role for the bHLH Protein Twist and the cdk Inhibitor p27." *J. Cell. Physiol.* 184(2000):101-109.
Li et al. "Effect of Growth Factors and Extracellular Matrix Materials on the Proliferation and Differentiation of Microencapsulated Myoblasts." *J. Biomater. Sci. Polym. Ed.* 14.6(2003):533-549.
Li et al. "Effects of Three-Dimensional Scaffolds on Cell Organization and Tissue Development." *Biotech. Bioprocess Eng.* 6.5(2001):311-325.
Li. "TNF-$\alpha$ is a Mitogen is Skeletal Muscle." *Am. J. Physiol. Cell Physiol.* 285(2003):C370-C376.
Lipton et al. "Developmental Fate of Skeletal Satellite Cells." *Science.* 205(1979):1292-1294.
Liu. "Dendritic Cell Subsets and Lineages, and Their Functions in Innate and Adaptive Immunity." *Cell.* 106.3(2001):259-262.
Lu et al. "Muscle-Derived Stem Cells Seeded Into Acellular Scaffolds Develop Calcium-Dependent Contractile Activity That is Modulated by Nicotinic Receptors." *Urology.* 61(2003):1285-1291.
Lubeck. "The Costs of Musculoskeletal Disease: Health Needs Assessment and Health Economics." *Best Pract. Res. Clin. Rheumatol.* 17.3(2003):529-539.
Lumelsky et al. "Differentiation of Embryonic Stem Cells to Insulin-Secreting Structures Similar to Pancreatic Islets." *Science.* 292. 5520(2001):1389-1394.
Mach et al. "Differences in Dendritic Cells Stimulated in Vivo by Tumors Engineered to Secrete Granulocyte-Macrophage Colony-Stimulating Factor or Flt3-Ligand." *Cancer Res.* 60.12(2000):3239-3246.
Magram et al. "IL-12-Deficient Mice are Defective but not Devoid of Type 1 Cytokine Responses." *Ann. N.Y. Acad. Sci.* 795(1996):60-70.
Maini. "Spatial and Spatio-Temporal Patterns in a Cell-Haptotaxis Model." *J. Math. Biol.* 27.5(1989):507-522.
Maley et al. "Extracellular Matrix, Growth Factors, Genetics: Their Influence on Cell Proliferation and Myotube Formation in Primary Cultures of Adult Mouse Skeletal Muscle." *Exp. Cell Res.* 219. 1(1995):169-179.
Martinsen et al. "Alginate as Immobilization Material." *Biotech. Bioeng.* 33.1(1989):79-89.
Massia et al. "An RGD Spacing of 440 nm is Sufficient for Integrin $\alpha v\beta 3$-Mediated Fibroblast Spreading and 140 nm for Focal Contact and Stress Fiber Formation." *J. Cell Biol.* 114.5(1991):1089-1100.
Matthew et al. "Subperiosteal Behaviour of Alginate and Cellulose Wound Dressing Materials." *Biomaterials.* 16.4(1995):275-278.
McKinney-Freeman et al. "Muscle-Derived Hematopoietic Stem Cells are Hematopoietic in Origin." *PNAS.* 99.3(2002):1341-1346.
McPherron et al. "Regulation of Skeletal Muscle Mass in Mice by a New TGF-$\beta$ Superfamily Member." *Nature.* 387(1997):83-90.
Melero-Martin et al. "Engineering Robust and Functional Vascular Networks In Vivo With Human Adult and Cord Blood-Derived Progenitor Cells." *Circ. Res.* 103.2(2008):194-202.
Mellman et al. "Dendritic Cells: Specialized and Regulated Antigen Processing Machines." *Cell.* 106.3(2001):255-258.

(56) References Cited

OTHER PUBLICATIONS

Menetrey et al. "Suturing Versus Immobilization of a Muscle Laceration: A Morphological and Functional Study in a Mouse Model." *Am. J. Sports Med.* 27.2(1999):222-229.
Meyer et al. "Clinical Investigations of Toll-Like Receptor Agonists." *Expert Opin. Investig. Drugs.* 17.7(2008):1051-1065.
Meylan et al. "Intracellular Pattern Recognition Receptors in the Host Response." *Nature.* 442.7098(2006):39-44.
Miller et al. "Hepatocyte Growth Factor Affects Satellite Cell Activation and Differentiation in Regenerating Skeletal Muscle." *Am. J. Physiol. Cell Physiol.* 278(2000):C174-C181.
Miller et al. "Lipopolysaccharide Sequestrants: Structural Correlates of Activity and Toxicity in Novel Acylhomospermines." *J. Med. Chem.* 48(2005):2589-2599.
Mitchell et al. "The Exogenous Administration of Basic Fibroblast Growth Factor to Regenerating Skeletal Muscle in Mice Does Not Enhance the Process of Regeneration." *Growth Factors.* 13.1-2(1996):37-55.
Moioli et al. "Matrices and Scaffolds for Drug Delivery in Dental, Oral and Craniofacial Tissue Engineering." *Adv. Drug Deliv. Rev.* 59.4-5(2007):308-324.
Mooney et al. "Switching From Differentiation to Growth in Hepatocytes: Control by Extracellular Matrix." *J. Cell. Phys.* 151.3(1992):497-505.
Moser et al. "Dendritic Cell Regulation of TH1-TH2 Regulation." *Nat. Immunol.* 1.3(2000):199-205.
Naik et al. "Development of Plasmacytoid and Conventional Dendritic Cell Subtypes From Single Precursor Cells Derived in vitro and in vivo." *Nat. Immunol.* 8.11(2007):1217-1226.
Nair et al. "Polymers as Biomaterials for Tissue Engineering and Controlled Drug Delivery." *Adv. Biochem. Eng. Biotechnol.* 102(2006):47-90.
NCBI Accession No. NM_000758, Apr. 1, 2012.
NCBI Accession No. NM_003265, Dec. 30, 2012.
NCBI Accession No. NM_017442, Apr. 14, 2012.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_003367, Jan. 30, 2011.
NCBI Accession No. NP_059138, Apr. 14, 2012.
Nehls et al. "A Novel, Microcarrier-Based in Vitro Assay for Rapid and Reliable Quantification of Three-Dimensional Cell Migration and Angiogenesis." *Microvasc. Res.* 50.3(1995):311-322.
Noguera-Troise et al. "Blockade of Dll4 Inhibits Tumour Growth by Promoting Non-Productive Angiogenesis." *Nature.* 444.7122(2006):1032-1037.
O'Garra et al. "Are Dendritic Cells Afraid of Commitment?" *Nat. Immunol.* 5.12(2004):1206-1208.
O'Shea et al. "Type 1 IFNs and Regulation of TH1 Responses: Enigmas Both Resolved and Emerge." *Nat. Immunol.* 1.1(2000):17-19.
Ohlstein et al. "The Stem Cell Niche: Theme and Variations." *Curr. Opin. Cell Biol.* 16.6(2004):693-699.
Oldenburg et al. "TLR13 Recognizes Bacterial 23S rRNA Devoid of Erythromycin Resistance-Forming Modification." *Science.* 337.6098(2012):1111-1115.
Oldenhove et al. "Decrease of Foxp3+ Treg Cell Number and Acquisition of Effector Cell Phenotype During Lethal Infection." *Immunity.* 31.5(2009):772-786.
Ota et al. "Percutaneous Subxiphoid Access to the Epicardium Using a Miniature Crawling Robotic Device." *Innovations.* 1.5(2006):227-231.
Overwijk et al. "Tumor Regression and Autoimmunity After Reversal of a Functionally Tolerant State of Self-Reactive CD8+ T Cells." *J. Exp. Med.* 198.4(2003):569-580.
Ozawa et al. "Microenvironmental VEGF Concentration, Not Total Dose, Determines a Threshold Between Normal and Aberrant Angiogenesis." *J. Clin. Invest.* 113.4(2004):516-527.
Padilla et al. "Insufficient TLR Activation Contributes to the Slow Development of CD8+ T Cell Responses in *Trypanosoma cruzi* Infection." *J. Immunol.* 183(2009):1245-1252.
Palacio et al. "Interleukin 10 and Tumor Necrosis Factor α Gene Expression in Respiratory and Peripheral Muscles." *Arch. Bronconeumol.* 38.7(2002):311-316. (Spanish Original and English Abstract).
Partridge et al. "Conversion of mdx Myofibres From Dystrophin-Negative to -Positive by Injection of Normal Myoblasts." *Nature.* 337(1989):176-179.
Pelinkovic et al. "Tissue Engineering and Gene Therapy of the Muscoskeletal System with Muscle Cells." *Z. Orthop. Ihre Grenzgeb.* 138.5(2000):402-406. (German Original and English Abstract).
Peters et al. "Engineering Vascular Networks in Porous Polymer Matrices." *J. Biomed. Mater. Res.* 60.4(2002):668-678.
Phillippi. "Patterning of Multiple Cell Lineages from a Single Stem Cell Population." Annual Meeting of the American Society for Cell Biology. (Dec. 10, 2006).
Pluen et al. "Role of Tumor-Host Interactions in Interstitial Diffusion of Macromolecules: Cranial vs. Subcutaneous Tumors." *PNAS.* 98.8(2001):4628-4633.
Pooyan et al. "Conjugates Beating Multiple Formyl-Methionyl Peptides Display Enhanced Binding to, but not Activation of Phagocytic Cells." *Bioconjugate Chem.* 13.2(2002):216-223.
Pope et al. "Organ-Specific Regulation of the CD8 T Cell Response to *Listeria monocytogenes* Infection." *J. Immunol.* 166(2001):3402-3409.
Pouzet et al. "Factors Affecting Functional Outcome After Autologous Skeletal Myoblast Transplantation." *Ann. Thorac. Surg.* 71(2001):844-851.
Pulendran et al. "Flt3-Ligand and Granulocyte Colony-Stimulating Factor Mobilize Distinct Human Dendritic Cell Subsets In Vivo." *J. Immunol.* 165(2000):566-572.
Qu et al. "Development of Approaches to Improve Cell Survival in Myoblast Transfer Therapy." *J. Cell Biol.* 142.5(1998):1257-1267.
Qu-Petersen et al. "Identification of a Novel Population of Muscle Stem Cells in Mice: Potential for Muscle Regeneration." *J. Cell Biol.* 157.5(2002):851-864.
Quezada et al. "CTLA4 Blockade and GM-CSF Combination Immunotherapy Alters the Intratumor Balance of Effector and Regulatory T Cells." *J. Clin. Invest.* 116.7(2006):1935-1945.
Rajagopalan et al. "Regional Angiogenesis With Vascular Endothelial Growth Factor in Peripheral Arterial Disease: A Phase II Randomized, Double-Blind, Controlled Study of Adenoviral Delivery of Vascular Endothelial Growth Factor 121 in Patients With Disabling Intermittent Claudication." *Circulation.* 108.16(2003):1933-1938.
Randolph et al. "Migration of Dendritic Cell Subsets and Their Precursors." *Annu. Rev. Immunol.* 26(2008):293-316.
Rappolee et al. "Macrophage-Derived Growth Factors." *Curr. Top. Microbiol. Immunol.* 181(1992):87-140.
Rapraeger. "Syndecan-Regulated Receptor Signaling." *J. Cell. Biol.* 149(2000):995-998.
Reddy et al. "Exploiting Lymphatic Transport and Complement Activation in Nanoparticle Vaccines." *Nat. Biotechnol.* 25.10(2007):1159-1164.
Reimann et al. "Satellite Cells in Normal and Regenerated Soleus Muscles of mdx and Control Mice." *Eur. J. Neurosci.*10(1998):366. (Abstract #153.07).
Richards Grayson et al. "Multi-Pulse Drug Delivery From a Resorbable Polymeric Microchip Device." *Nat. Mater.* 2.11(2003):767-772.
Richardson et al. "Polymeric System for Dual Growth Factor Delivery." *Nat. Biotech.* 19.11(2001):1029-1034.
Riddle et al. "Role of Poly(lactide-co-glycolide) Particle Size on Gas-Foamed Scaffolds." *J. Biomater. Sci. Polym. Ed.* 15.12(2004):1561-1570.

(56) References Cited

OTHER PUBLICATIONS

Ridgway et al. "Inhibition of Dll4 Signalling Inhibits Tumour Growth by Deregulating Angiogenesis." *Nature*. 444. 7122(2006):1083-1087.
Rinderknecht et al. "The Amino Acid Sequence of Human Insulin-Like Growth Factor I and its Structural Homology with Proinsulin." *J. Biol. Chem.* 253.8(1978):2769-2776.
Rosenberg et al. "Cancer Immunotherapy: Moving Beyond Current Vaccines." *Nat. Med.* 10.9(2004):909-915.
Roth et al. "SC68896, a Novel Small Molecule Proteasome Inhibitor, Exerts Antiglioma Activity In vitro and In vivo." *Clin. Cancer Res.* 15.21(2009):6609-6618.
Rowlands et al. "Directing Osteogenic and Myogenic Differentiation of MSCs: Interplay of Stiffness and Adhesive Ligand Presentation." *Am. J. Physiol Cell Physiol*. 295(2008): 1037-1044.
Rowley et al. "Alginate Type and RGD Density Control Myoblast Phenotype." *J. Biomed. Mater. Res.* 60.2(2002):217-233.
Rowley et al. "Biomaterials to Spatially Regulate Cell Fate." *Adv. Mater.* 14.12(2002):886-889.
Rowley. "Alginate Hydrogels as Synthetic Extracellular Matrix Materials." *Biomaterials*. 20.1(1999):45-53.
Rubin et al. "Dissociation of Heparan Sulfate and Receptor Binding Domains of Hepatocyte Growth Factor Reveals That Heparan Sulfate-c-Met Interaction Factilitates Signaling." *J. Biol. Chem.* 276.35(2001):32977-32983.
Ryten et al. "ATP Regulates the Differentiation of Mammalian Skeletal Muscle by Activation of a P2X5 Receptor on Satellite Cells." *J. Cell. Biol.* 158.2(2002):345-355.
Ryu et al. "The Construction of Three-Dimensional Micro-Fluidic Scaffolds of Biodegradable Polymers by Solvent Vapor Based Bonding of Micro-Molded Layers." *Biomaterials*. 28.6(2007):1174-1184.
Salvador et al. "Combination of Immune Stimulating Adjuvants With Poly(lactide-co-glycolide) Microspheres Enhances the Immune Response of Vaccines." *Vaccine*. 30.3(2011):589-596.
Salvay et al. "Inductive Tissue Engineering with Protein and DNA-Releasing Scaffolds." *Mol. Biosyst.* 2.1(2006):36-48.
Sano et al. "Swift Development of Protective Effector Functions in Naive CD8+ T Cells Against Malaria Liver Stages." *J. Exp. Med.* 194.2(2001):173-179.
Sansonetti. "The Innate Signaling of Dangers and the Dangers of Innate Signaling." *Nat. Immunol.* 7.12(2006):1237-1242.
Saxena et al. "Skeletal Muscle Tissue Engineering Using Isolated Myoblasts on Synthetic Biodegradable Polymers: Preliminary Studies." *Tissue Eng*. 5.6(1999):525-532.
Schaefer et al. "Innate Immunity in the Human Female Reproductive Tract: Antiviral Response of Uterine Epithelial Cells to TLR3 Agonist Poly (I:C)." *J. Immunol.* 174(2005):992-1002.
Schijns et al. "Mice Lacking IL-12 Develop Polarized Th1 Cells During Viral Infection." *J. Immunol.* 160(1998):3958-3964.
Schnorrer et al. "The Dominant Role of CD8+ Dendritic Cells in Cross-Presentation is not Dictated by Antigen Capture." *PNAS*. 103.28(2006):10729-10734.
Schuler et al. "The Use of Dendritic Cells in Cancer Immunotherapy." *Curr. Opin. Immunol.* 15.2(2003):138-147.
Seale et al. "Pax7 Is Required for the Specification of Myogenic Satellite Cells." *Cell*. 102.6(2000):777-786.
Shakweh et al. "Design and Characterisation of Poly(lactide-co-glycolide) Small Particulate Systems for the Delivery of Immunostimulant CpG Oligonucleotide." *J. Nanosci. Nanotechnol.* 6.9-10(2006):2811-2820.
Shansky et al. "Letter to the Editor: A Simplified Method for Tissue Engineering Skeletal Muscle Organoids In Vitro." *In Vitro Cell. Dev. Biol.* 33(1997):659-661.
Sheehan et al. "Skeletal Muscle Satellite Cell Proliferation in Response to Members of the Fibroblast Growth Factor Family and Hepatocyte Growth Factor." *J. Cell. Physiol.* 181.3(1999):499-506.
Sheridan et al. "Bioabsorbable Polymer Scaffolds for Tissue Engineering Capable of Sustained Growth Factor Delivery." *J. Control. Release*. 64.1-3(2000):91-102.

Shi et al. "A Novel Toll-Like Receptor that Recognizes Vascular Stomatitis Virus." *J. Biol. Chem.* 286.6(2011):4517-4524.
Shortman et al. "Steady-State and Inflammatory Dendritic-Cell Development." *Nat. Rev. Immunol.* 7(2007):19-30.
Sick et al. "WNT and DKK Determine Hair Follicle Spacing Through a Reaction-Diffusion Mechanism." *Science*. 314. 5804(2006):1447-1450.
Silva et al. "Spatiotemporal Control of Vascular Endothelial Growth Factor Delivery From Injectable Hydrogels Enhances Angiogenesis." *J. Thromb. Haemost*. 5.3(2007):590-598.
Skokos et al. "CD8- DCs Induce IL-12-Independent Th1 Differentiation Through Delta 4 Notch-Like Ligand in Response to Bacterial LPS." *J. Exp. Med.* 204.7(2007):1525-1531.
Skuk et al. "Efficacy of Myoblast Transplantation in Nonhuman Primates Following Simple Intramuscular Cell Injections: Toward Defining Strategies Applicable to Humans." *Exp. Neurol.* 175. 1(2002):112-126.
Skuk et al. "Myoblast Transplantation: The Current Status of a Potential Therapeutic Tool for Myopathies." *J. Musc. Res. Cell. Motil.* 24.4-6(2003):285-300.
Smidsrød et al. "Alginate as Immobilization Matrix for Cells." *Trends Biotechnol*. 8.3(1990):71-78.
Sohier et al. "Critical Factors in the Design of Growth Factor Releasing Scaffolds for Cartilage Tissue Engineering." *Exp. Opin. Drug Deliv.* 5.5(2008):543-566.
Steinman et al. "Taking Dendritic Cells into Medicine." *Nature*. 449.7161(2007):419-426.
Storrie et al. "Sustained Delivery of Plasmid DNA From Polymeric Scaffolds for Tissue Engineering." *Adv. Drug Deliv. Rev.* 58.4(2006):500-514.
Straub et al. "Animal Models for Muscular Dystrophy Show Different Patterns of Sarcolemmal Distruption." *J. Cell Biol.* 139. 2(1997):375-385.
Sun et al. "Sustained Vascular Endothelial Growth Factor Delivery Enhances Angiogenesis and Perfusion in Ischemic Hind Limb." *Pharm. Res.* 22.7(2005):1110-1116.
Takeshita et al. "Therapeutic Angiogenesis." *J. Clin. Invest.* 93.2(1994):662-670.
Tamura et al. "Immunotherapy of Tumors with Autologous Tumor-Derived Heat Shock Protein Preparations." *Science*. 278. 3(1997):117-120.
Tatsumi et al. "HGF/SF Is Present in Normal Adult Skeletal Muscle and Is Capable of Activating Satellite Cells." *Dev. Biol.* 194. 1(1998):114-128.
Thurston et al. "The Delta Paradox: DLL4 Blockade Leads to More Tumour Vessels but Less Tumour Growth." *Nat. Rev. Cancer*. 7.5(2007):327-331.
Tidball. "Inflammatory Cell Response to Acute Muscle Injury." *Med. Sci. Sports Exerc.* 27.7(1995):1022-1032.
Turing. "Discussion: Turing's Theory of Morphogenesis—Its Influence on Modelling Biological Pattern and Form." *Bull. Math. Biol.* 52.1-2(1990):119-159.
Turing. "The Chemical Basis of Morphogenesis." *Philosophical Transactions of the Royal Society of London. Series B*. 237. 641(1952):37-72.
Uchida et al. "Immunization by Particle Bombardment of Antigen-Loaded poly-(DL-lactide-co-glycolide) Microspheres in Mice." *Vaccine*. 12(2006):2120-2130.
Urbanek et al. "Stem Cell Niches in the Adult Mouse Heart." *PNAS*. 103.24(2006):9226-9231.
van Duin et al. "Triggering TLR Signaling in Vaccination." *Trends Immunol*. 27.1(2006):49-55.
Vandenburgh et al. "Tissue-Engineered Skeletal Muscle Organoids for Reversible Gene Therapy." *Hum. Gene Ther.* 17(1996):2195-2200.
Vieira et al. "The Bulk of Endogenously Produced IgG2a is Eliminated From the Serum of Adult C57BL/6 Mice With a Half-Life of 6-8 Days." *Eur. J. Immunol.* 16.7(1986):871-874.
Vieira et al. "The Half-Lives of Serum Immunoglobulins in Adult Mice." *Eur. J. Immunol.* 18.2(1988):313-316.
Villadangos et al. "Intrinsic and Cooperative Antigen-Presenting Functions of Dendritic-Cell Subsets in vivo." *Nat. Rev. Immunol.* 7.7(2007):543-555.

(56) References Cited

OTHER PUBLICATIONS

Villadangos. "Presentation of Antigens by Mhc Class Ii Molecules: Getting the Most Out of Them." *Molec. Immunol.* 38.5(2001):329-346.
von Dassow et al. "The Segment Polarity Network is a Robust Developmental Module." *Nature.* 406.6792(2000):188-192.
Wakim et al. "Dendritic Cell-Induced Memory T Cell Activation in Nonlymphoid Tissues." *Science.* 319(2008):198-202.
Waldron-Lynch et al. "Advances in Type 1 Diabetes Therapeutics: Immunomodulation and β-Cell Savage." *Endocrinol. Metab. Clin. North Am.* 38.2(2009):303-317.
Wan et al. "Peritoneal Macrophage Uptake, Pharmacokinetics and Biodistribution of Macrophage-Targeted PEG-fMLF (N-Formyl-Methionyl-Leucyl-Phenylalanine) Nanocarriers for Improving HIV Drug Delivery." *Pharm. Res.* 24.11(2007):2110-2119.
Wang et al. "Biological Activity of Bevacizumab, a Humanized Anti-VEGF Antibody in vitro." *Angiogenesis.* 7.4(2004):335-345.
Wei et al. "Global Mapping of H3K4me3 and H3K27me3 Reveals Specificity in Plasticity in Lineage Fate Determination of Differentiating CD4+ T Cells." *Immunity.* 30.1(2009):155-167.
Wernig et al. "Function of Skeletal Muscle Tissue Formed After Myoblast Transplantation into Irradiated Mouse Muscles." *J. Physiol.* 522.2(2000):333-345.
White et al. "Leukemia Inhibitory Factor Enhances Regeneration in Skeletal Muscles After Myoblast Transplantation." *Musc. Nerve.* 24.5(2001):695-697.
World Health Organization. "Global Burden of Musculoskeletal Disease Revealed in new WHO Report." *Bull. World Health Organ.* 81.11(2003):853-854.
World Health Organization. "The World Health Report 2004: Changing History." *The World Health Report.* (2004):1-169.
Wright et al. "Muscle-Based Gene Therapy and Tissue Engineering for the Musculoskeletal System." *Drug Disc. Today.* 6.14(2001):728-733.
Yancopoulos et al. "Vascular-Specific Growth Factors and Blood Vessel Formation." *Nature.* 407.6801(2000):242-248.
Yuen et al. "Mimicking Nature by Codelivery of Stimulant and Inhibitor to Create Temporally Stable and Spatially Restricted Angiogenic Zones." *PNAS.* 107.42(2010):17933-17938.
Zammit et al. "Kinetics of Myoblast Proliferation Show That Resident Satellite Cells are Competent to Fully Regenerate Skeletal Muscle Fibers." *Exp. Cell Res.* 281.1(2002):39-49.
Zammit et al. "Muscle Satellite Cells Adopt Divergent Fates: A Mechanism for Self-Renewal?" *J. Cell Biol.* 166.3(2004):347-357.
Zeltinger et al. "Effect of Pore Size and Void Fraction on Cellular Adhesion, Proliferation, and Matrix Deposition." *Tissue Eng.* 7.5(2001):557-572.
Zhang et al. "A Comparative Study of the Antigen-Specific Immune Response Induced by Co-Delivery of CpG OGN and Antigen Using Fusion Molecules or Biodegradable Microparticles." *J. Pharma. Sci.* 98.12(2007):3283-3292.
Zhao et al. "Active Scaffolds for On-Demand Drug and Cell Delivery." *PNAS.* 108.1(2011):67-72.
Zhao et al. "Directed Cell Migration via Chemoattractants Released from Degradable Microspheres." *Biomat.* 26(2005):5048-5063.
Zhou et al. "Microstructure and Mechanical Properties of Poly(L-lactide) Scaffolds Fabricated by Gelatin Particle Leaching Method." *J. Appl. Polymer Sci.* 98(2005):1373-1379.

\* cited by examiner

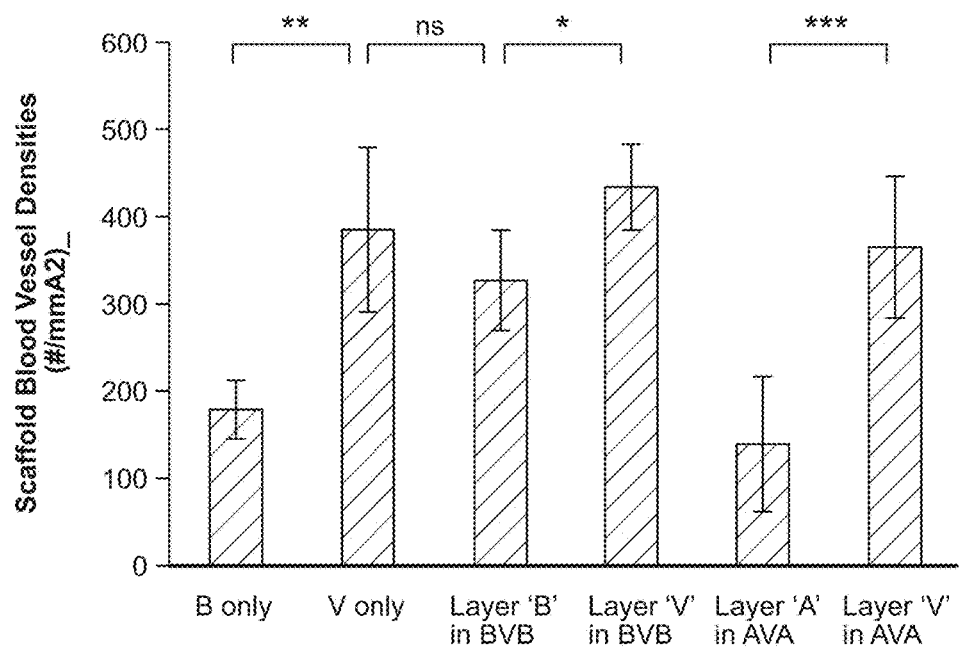

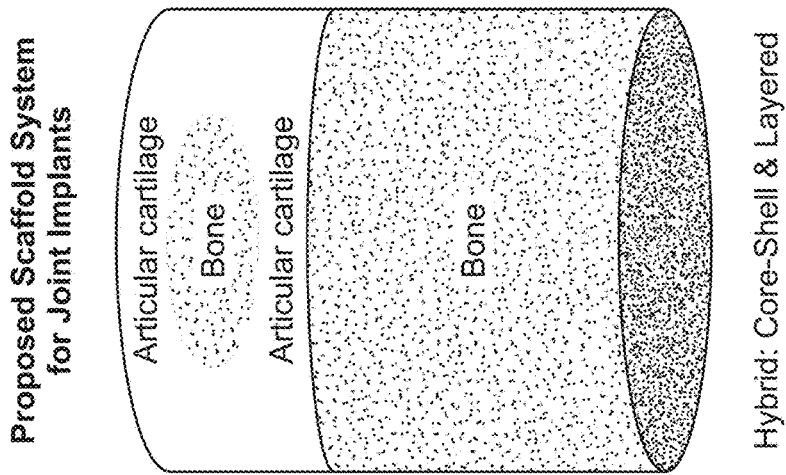
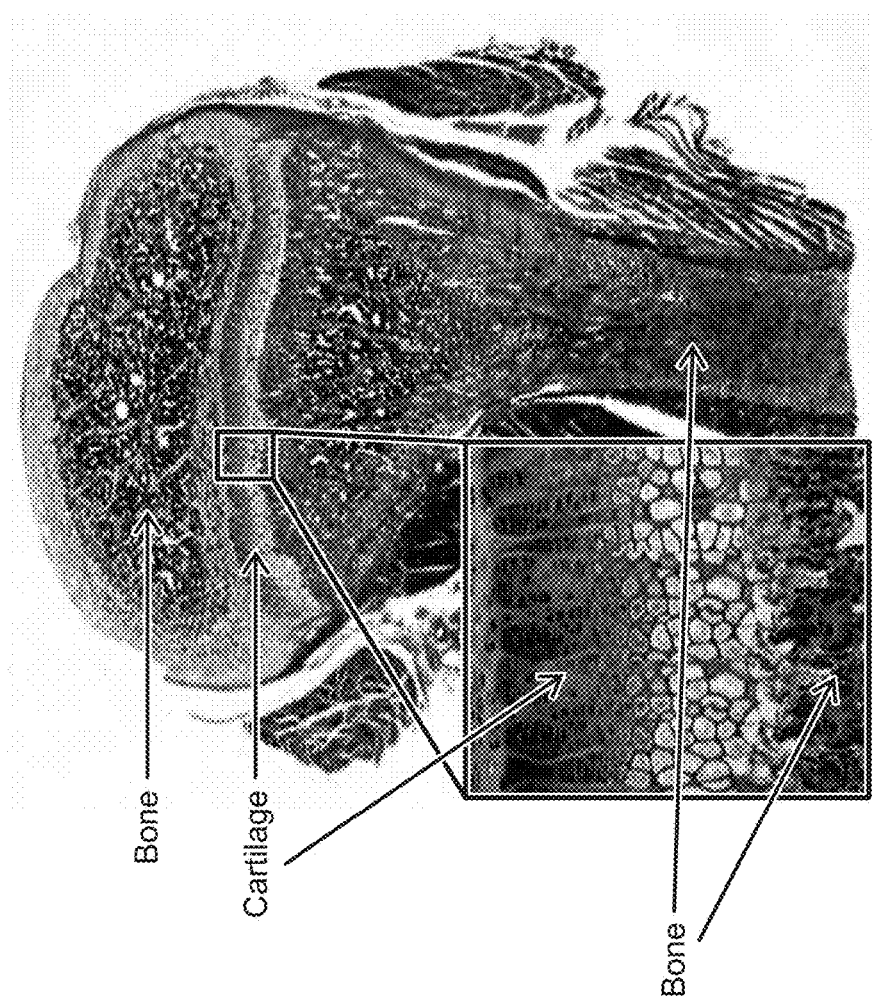
FIG. 19

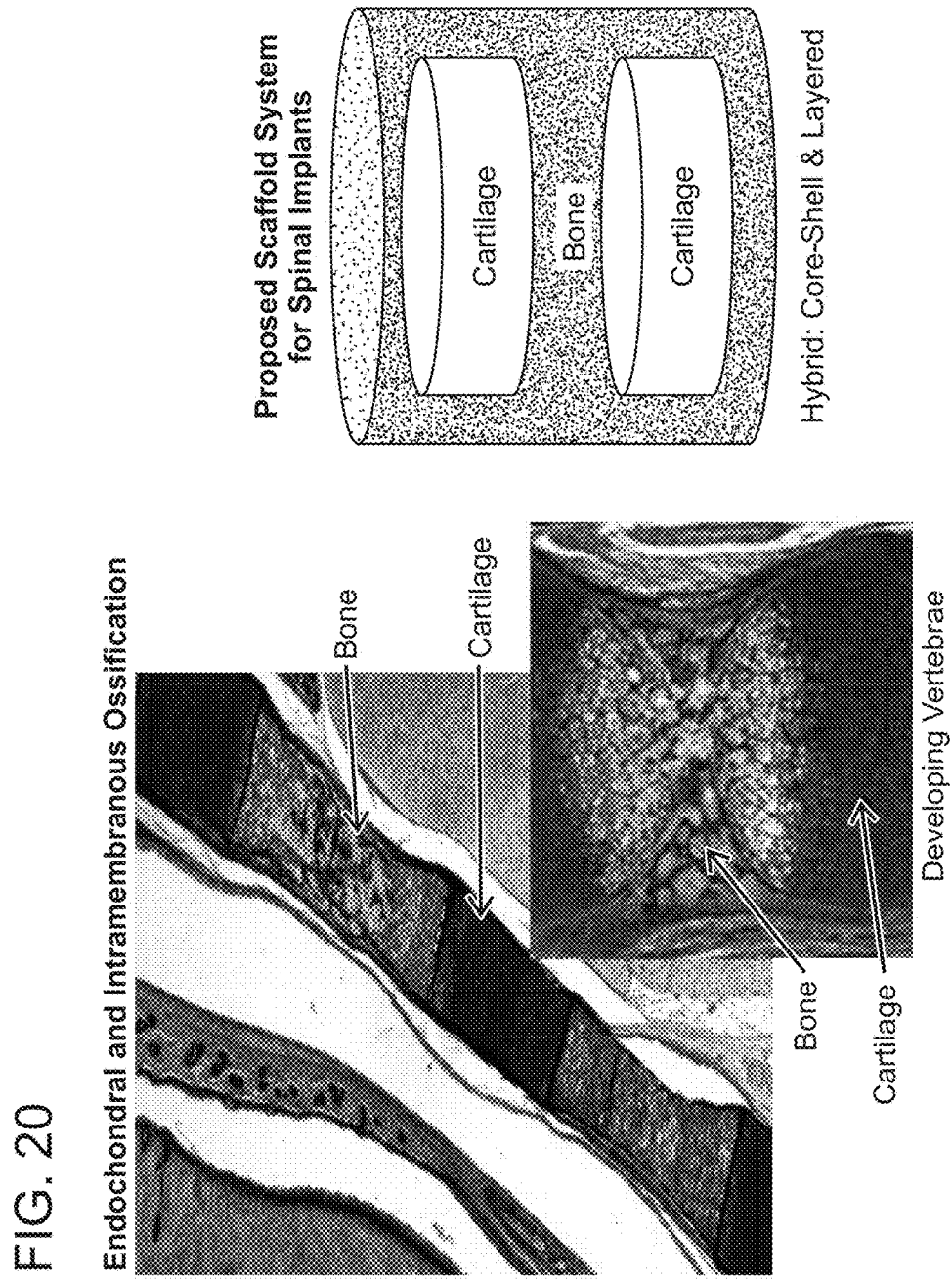

$$\frac{\delta TGF}{\delta t} = D_{TGF}\nabla^2(TGF) - k_{TGF}(TGF) + f_{TGF,release}(t) - k_{on}(TGF)(abTGF) + k_{off}(TGFcomplex)$$

$$\frac{\delta abTGF}{\delta t} = D_{abTGF}\nabla^2(abTGF) - k_{abTGF}(abTGF) + f_{abTGF,release}(t) - k_{on}(TGF)(abTGF) + k_{off}(TGFcomplex)$$

$$\frac{\delta(TGFcomplex)}{\delta t} = D_{abTGFcomplex}\nabla^2(TGFcomplex) - k_{TGFcomplex}(TGFcomplex) + k_{on}(TGF)(abTGF) - k_{off}(TGFcomplex)$$

US 9,693,954 B2

CO-DELIVERY OF STIMULATORY AND INHIBITORY FACTORS TO CREATE TEMPORALLY STABLE AND SPATIALLY RESTRICTED ZONES

RELATED APPLICATIONS

This application is a national stage application, filed under 35 U.S.C. §371, of International Application No. PCT/US2011/042051, filed Jun. 27, 2011, which claims the benefit of U.S. Provisional Patent Application No. 61/358,499, filed on Jun. 25, 2010, the contents of which are incorporated herein by reference in their entireties.

STATEMENT AS TO FEDERALLY SPONSORED RESEARCH

This invention was made with Government support under National Institutes of Health awards R01HL069957 and R37DE013033. The Government has certain rights in the invention

FIELD OF THE INVENTION

This invention relates generally to the field of drug delivery.

BACKGROUND OF THE INVENTION

Nature frequently utilizes opposing factors to create a stable activator gradient to robustly control pattern formation. Specifically, during developmental processes, tight spatial regulation often results from the combined action of stimulatory and inhibitory factors. In such reaction schemes, the reactions of morphogens and their diffusion through a tissue are adequate in describing morphogenesis and creating sharp boundaries in patterns. However, the diffusion/reaction of stimulatory factors alone results in the formation of shallow gradients that make cellular discrimination of spatial cues difficult. Prior to the invention described herein, the art-recognized strategy for delivering stimulatory factors alone to promote regeneration has ignored this fundamental principle of developmental biology. As such, there has been a long-felt need in the art for the discovery of new approaches to locally manipulate regenerative processes via exogenous factor delivery.

SUMMARY OF THE INVENTION

The invention is based on the surprising discovery that biological processes, e.g., the regeneration of muscle tissue or other tissues, cell differentiation, as well as angiogenesis, can be temporally and spatially (directionally) controlled by simultaneously delivering from a single source/location stimulatory and inhibitory agents that are spatially segregated. For example, the source is a polymeric structure or device, and the agents are segregated from one another by different layers or zones of the structure or device. A method for promoting a morphogenic process is carried out by administering to a subject a composition or device comprising at least one purified morphogen and at least one purified inhibitor or antagonist of the morphogen (e.g., small molecule inhibitor, antibody or fragment thereof that binds to the morphogen or its receptor, or a soluble ligand that binds to the morphogen or its receptor or a second morphogen. In the latter situation in which the antagonist is a second morphogen, the second morphogen promotes a morphogenic process that is different from that driven by the first morphogen. For example, the first morphogen is a differentiation factor that promotes differentiation of cells toward a first tissue type, and the second morphogen is a second differentiation factor that promotes differentiation of cells toward a second tissue type.

The morphogen and the inhibitor remain inside the device and interact there, or they are released from the composition or device and interact, e.g., outside of the composition and device, to promote the morphogenic process over a sustained period of time (e.g., 4 hours, 8 hours, 12 hours, 1 day, 3 days, 7 days, 14 days, 21 days, or 1 month) at a spatially restricted zone at or near a site at which the morphogen and the inhibitor interact in the subject. For example, the morphogen and inhibitor interact within the device or near the device, e.g., about 0.1 cm, about 0.5 cm, about 1 cm, about 2 cm, about 3 cm, about 4 cm, about 5 cm, about 6 cm, about 7 cm, about 8 cm, about 9 cm, or about 10 cm from the site of the device. In some embodiments, the morphogen and the inhibitor are both present in the device and interact within the device to direct proliferation, differentiation, regeneration, or other activities of cells that have been seeded in the device prior to implantation or bodily cells that have entered the device after implantation into an animal. Optionally, the factors (morphogen inhibitor) are released from the device and the morphogen is released at a first rate and the inhibitor is released at a second rate. Exemplary morphogenic processes include angiogenesis, tissue regeneration, organ regeneration, cartilage regeneration, bone regeneration, cell differentiation, or neural regeneration. Suitable morphogens include vascular endothelial growth factor (e.g., VEGFA; GenBank Accession Number: (aa) AAA35789.1 (GI:181971), (na) NM_001171630.1 (GI:284172472), incorporated herein by reference), acidic fibroblast growth factor (aFGF, Genbank Accession Number: (aa) AAB29057.2 (GI:13236891), (na) NM_000800.3 (GI:222144219), incorporated herein by reference), basic fibroblast growth factor (bFGF; GenBank Accession Number: (aa) AAB21432.2 (GI:8250666), (na) A32848.1 (GI:23957592), incorporated herein by reference), placenta growth factor (PlGF or PLGF; GenBank Accession Number: (aa) AAH07789.1 (GI:14043631), (na) NM_002632.4 (GI:56676307), incorporated herein by reference), leptin (Genbank Accession Number: (aa) CBI71013.1 (GI:285310289), (na) NM_000230.2 (GI:169790920), incorporated herein by reference), hematopoietic growth factor (e.g., HGF, Genbank Accession Number: (aa) AAA64297.1 (GI:337938), (na) NM_000601.4 (GI:58533168), incorporated herein by reference), VEGF receptor-1 (VEGFR-1, Genbank Accession Number: (aa) NP_002010.2 (GI:156104876), incorporated herein by reference), VEGFR-2 (Genbank Accession Number: (aa) AAC16450.1 (GI:3132833), (na) EU826563.1 (GI:194318421), incorporated herein by reference), transforming growth factor-β (TGF-β, Genbank Accession Number: (aa) AAA36738.1 (GI:339564), (na) NM_000660.4 (GI:260655621), incorporated herein by reference), bone morphogenetic protein (e.g., BMP-4, Genbank Accession Number: (aa) NP_570912.2 (GI:157276597), (na) NM_001202.3 (GI:157276592), incorporated herein by reference), insulin-like growth factor (IGF-1, Genbank Accession Number: (aa) CAA01954.1 (GI:1247519), (na) NM_001111283.1 (GI:163659898), incorporated herein by reference), fibroblast growth factor-2 (FGF-2), platelet-derived growth factor (PDGF; GenBank Accession Number: (aa) AAA60552.1 (GI:338209), (na) NM_033023.4 (GI:197333759), incorporated herein by reference), epidermal growth factor (EGF, Genbank Accession Number: (aa) AAH93731.1 (GI:

62740195), incorporated herein by reference), transforming growth factor-α (TGF-α, Genbank Accession Number: (na) NM_003236.2 (GI:153791671), incorporated herein by reference), nerve growth factor (NGF, Genbank Accession Number: (aa) AAH32517.2 (GI:34192369), (na) NM_002506.2 (GI:70995318), incorporated herein by reference), brain-derived neurotrophic factor (BDNF, Genbank Accession Number: (aa) CAA62632.1 (GI:987872), (na) NM_170731.4 (GI:219842281), incorporated herein by reference), neurotrophin-3 (NT-3, Genbank Accession Number: (aa) NP_001096124.1 (GI:156630995), (na) NM_001102654.1 (GI:156630994), incorporated herein by reference), ciliary neurotrophic factor (CNTF, Genbank Accession Number: (aa) AAB31818.1 (GI:633830), (na) NM_000614.3 (GI:209574322), incorporated herein by reference), and glial cell line-derived neurotrophic factor (GDNF, Genbank Accession Number: (aa) CAG46721.1 (GI:49456801), (na) NM_000514.3 (GI:299473777), incorporated herein by reference). Suitable morphogen inhibitors include anti-VEGF antibody, anti-aFGF antibody, anti-bFGF antibody, anti-PlGF antibody, anti-leptin antibody, anti-HGF antibody, anti-VEGFR-1 antibody, anti-VEGFR-2 antibody, batimastat (BB-94), marimastat (BB-2516), thalidomide, O-(chloroacetylcarbamoyl)-fumagillol (TNP-470), carboxyamidotriazole (CAI), SU5416, anti-TGF-β antibody, anti-BMP antibody, anti-IGF-1 antibody, anti-FGF-2 antibody, anti-PDGF antibody, anti-EGF antibody, anti-TGF-α antibody, and anti-VEGF antibody.

One therapeutic application of the device exemplified herein is angiogenesis (i.e., a physiological process involving the growth and development of new blood vessels from pre-existing vessels) via the administration of vascular endothelial growth factor (VEGF) and anti-VEGF, but the devices are also useful in other drug delivery applications in order to mitigate the negative effects of initial bursts of morphogenic factors (a drawback of some earlier devices). The methods described herein are applicable to any process controlled by morphogen signaling, e.g., regenerative or developmental processes in tissues and organs that require spatial patterning. For example, the methods described herein are applicable to neural regeneration, bone (e.g., tooth) regeneration, and epithelial patterning.

Also provided are methods of temporally and spatially (directionally) controlling regenerative processes by simultaneously delivering from a single source/location agents that act synergistically (e.g., basic fibroblast growth factor (bFGF) and VEGF) rather than antagonistically to create spatial patterns/control.

A method for inducing sustained angiogenesis in a spatially restricted zone is carried out by contacting a tissue with a purified angiogenesis-promoting agent and contacting the tissue with a purified inhibitor of angiogenesis. In one aspect, the inhibitor of angiogenesis is a specific inhibitor of the angiogenesis-promoting agent. In another aspect, the inhibitor of angiogenesis is a general inhibitor of angiogenesis. The agent and the inhibitor interact thereby inducing sustained angiogenesis in a spatially restricted zone at or near a site at which the agent and the inhibitor interact. For example, the interaction is an association and disassociation of an agent and an antibody that specifically binds to that agent. Alternatively, methods for inducing sustained angiogenesis in a spatially restricted zone are carried out by contacting a tissue with angiogenesis-promoting agents that act synergistically, e.g., bFGF and VEGF.

The methods are useful in treating and/or preventing degenerative disorders, diseases or conditions, and for tissue generation, regeneration, or repair. The subject is preferably a mammal in need of such treatment. The mammal can be, e.g., any mammal, e.g., a human, a primate, a mouse, a rat, a dog, a cat, a cow, a horse, or a pig. In a preferred embodiment, the mammal is a human.

Suitable bioactive agents that promote regeneration include growth factors, homing/migration factors, morphogens, differentiation factors, oligonucleotides, hormones, neurotransmitters, neurotransmitter or growth factor receptors, interferons, interleukins, chemokines, cytokines, colony stimulating factors, chemotactic factors, extracellular matrix components, adhesion molecules, and other bioactive compounds. The concentration each agent is manipulated to achieve the desired result.

Therapeutic applications of the methods described herein include tissue generation, regeneration/repair, as well as augmentation of function of a mammalian bodily tissue, and the targeted destruction of undesired tissues (e.g., cancer, undesired adipose depots), as well as the instruction of immune cells. For example, the co-administration of stimulatory and inhibitory agents programs or reprograms resident cells to a desired fate (e.g., immune activation or tissue regeneration). Alternatively, the co-delivery of stimulatory and inhibitory bioactive agents results in muscle regeneration, repair or replacement; liver tissue regeneration, repair or organ transplantation; cartilage replacement, regeneration or repair, bone regeneration, replacement or repair; or neural regeneration. The co-delivery of stimulatory and inhibitory bioactive agents promotes or inhibits differentiation of various stem cell populations (embryonic stem cells differentiated into various cell types) including bone marrow or adipose tissue derived adult stem cells, cardiac stem cells, pancreatic stem cells, endothelial progenitors and outgrowth endothelial cells, mesenchymal stem cells, hematopoietic stem cells, neural stem cells, satellite cells, side population cells. Other cell populations include osteoprogenitors and osteoblasts, chondrocytes, keratinocytes for skin, tenocytes for tendon, intestinal epithelial cells, endothelial cells, smooth muscle cells and fibroblasts for tissue or organ regeneration, repair or replacement and/or for DNA delivery. Preferably, the cells are human; however, the methods described herein are adaptable to other eucaryotic animal cells, e.g., canine, feline, equine, bovine, and porcine as well as prokaryotic cells such as bacterial cells.

In one aspect, the stimulatory and inhibitory agents are delivered with polymeric scaffolds in vivo or in vitro. Exemplary scaffold compositions include polylactic acid, polyglycolic acid, poly(lactic-co-glycolic acid) (PLGA) polymers, alginates and alginate derivatives, gelatin, collagen, fibrin, hyaluronic acid, laminin rich gels, agarose, natural and synthetic polysaccharides, polyamino acids, polypeptides, polyesters, polyanhydrides, polyphosphazines, poly(vinyl alcohols), poly(alkylene oxides), poly(allylamines)(PAM), poly(acrylates), modified styrene polymers, pluronic polyols, polyoxamers, poly(uronic acids), poly (vinylpyrrolidone) and copolymers or graft copolymers of any of the above. One preferred scaffold composition includes an arginine-glycine-aspartate (RGD)-modified alginate. The density and mixture of the bioactive agents and inhibitors is controlled by initial doping levels or concentration gradient of the substance, by embedding the bioactive substances in scaffold material with a known leaching rate, by release as the scaffold material degrades, by diffusion from an area of concentration, by interaction of precursor chemicals diffusing into an area, or by production/ excretion of compositions by resident support cells. The physical or chemical structure of the scaffold also regulates the diffusion of bioactive agents.

Alternatively, the stimulatory and inhibitory bioactive agents are administered in drops, injections, or other implantable devices, depending on the precise nature of the formulation and the desired outcome of the administration. The bioactive agents of the invention are administered in any form suitable for drug administration, e.g., dosage forms suitable for topical administration, a solution or suspension for administration as eye drops or washes, ointment, gel, liposomal dispersion, colloidal microparticle suspension, or the like.

The compositions administered according to the present invention optionally also include various other ingredients, including but not limited to surfactants, tonicity agents, buffers, preservatives, co-solvents and viscosity building agents. In carriers that are at least partially aqueous one may employ thickeners, isotonic agents, buffering agents, and preservatives, providing that any such excipients do not interact in an adverse manner with any of the formulation's other components.

The co-delivery of stimulatory and inhibitory bioactive agents may interfere with signal transduction events. Signal transduction events that participate in the process of cell motility are initiated in response to cell growth and/or cell differentiation factors. Thus, the invention optionally provides a bioactive agent that is a growth factor, morphogen, differentiation factor, or chemoattractant. For example, the device includes vascular endothelial growth factor (VEGF), hepatocyte growth factor (HGF), or fibroblast growth factor 2 (FGF2) or a combination thereof. Other factors include hormones, neurotransmitters, neurotransmitter or growth factor receptors, interferons, interleukins, chemokines, matrix metalloproteinase (MMP)-sensitive substrate, cytokines, and colony stimulating factors. Growth factors used to promote angiogenesis, bone regeneration, neural regeneration, wound healing, and other aspects of tissue regeneration are listed herein and are used alone or in combination to induce colonization or regeneration of bodily tissues.

Immune cells such as T cells, B cells, or dendritic cells (DCs) of an individual are recruited to the site of bioactive agent administration, primed and activated to mount an immune response against an antigen-specific target. Optionally, an antigen corresponding to a target to which an immune response is desired is delivered to the mammal. Cytokines, such as granulocyte macrophage colony stimulating factor (GM-CSF) are suitable to amplify immune activation and/or induce migration of the primed cells to lymph nodes. Other cell specific recruitment compositions are described below. For example, vascular endothelial growth factor (VEGF) is useful to recruit angiogenic cells.

This approach is exemplified herein in the context of angiogenesis via the administration of VEGF and anti-VEGF, but is also useful in other drug delivery applications in order to mitigate the negative effects of initial bursts, as well as regenerative processes in general. The in vivo and in vitro methods described herein promote regeneration of a tissue or organ immediately adjacent to the bioactive agents, or at some distant site. Alternatively, the methods described herein promote destruction of a tissue (locally or at a distant site). The methods are also useful for disease prevention, e.g., to promote cell-based maintenance of tissue structure and function and to stop or retard disease progression or age-related tissue changes.

The invention provides in vivo and in vitro methods for inducing angiogenesis by contacting a tissue with an agent that promotes angiogenesis (i.e., growth and development of new blood vessels from pre-existing vessels), and contacting the tissue with an inhibitor of angiogenesis. In one aspect, the inhibitor of angiogenesis is a specific inhibitor of the agent that promotes angiogenesis. Alternatively, the inhibitor of angiogenesis is a general inhibitor of angiogenesis. In one aspect, the agent and agent inhibitor are administered in a 1:1 ratio. In other aspects, the agent/agent inhibitor are administered in a 1:2; 1:5; 1:10; 1:100; 1:1,000; or 1,000:1, 100:1, 10:1, 5:1, or 2:1 ratio. Preferably, the agent and the inhibitor are administered simultaneously. In one aspect, the agent and the inhibitor are incorporated in or on a device comprising a scaffold composition. The agent and the inhibitor are spatially segregated in or on the scaffold composition. Alternatively, the agent and inhibitor are injected directly into the tissue, e.g., an artery. The simultaneous delivery of agents and agent inhibitors maintains the temporal stability of the active agent concentration profile. Preferably, the angiogenesis methods described herein result in heterogeneous distribution of blood vessels.

Suitable agents for the promotion of angiogenesis include vascular endothelial growth factor (VEGF), acidic fibroblast growth factor (aFGF), basic fibroblast growth factor (bFGF), placenta growth factor (PIGF), leptin, hematopoietic growth factor (HGF), VEGF receptor-1 (VEGFR-1), and VEGFR-2. Suitable inhibitors of angiogenesis include anti-VEGF antibody, anti-aFGF antibody, anti-bFGF antibody, anti-PIGF antibody, anti-leptin antibody, anti-HGF antibody, anti-VEGFR-1 antibody, and anti-VEGFR-2 antibody. Suitable agents for the promotion of angiogenesis include fibroblast growth factor-2 (FGF-2), matrix metalloproteinase-9 (MMP-9), interleukin-8 (IL-8), and IL-6. Suitable angiogenic inhibitors include endostatin, tumstatin, and pigment epithelium-derived factor (PEDF). Small molecule inhibitors of angiogenesis include batimastat (BB-94) and marimastat (BB-2516), metalloproteinase inhibitors; thalidomide, a hypnosedative agent; O-(chloroacetylcarbamoyl)-fumagillol (TNP-470), a fumagillin analog; carboxyamidotriazole (CAI), a calcium channel blocker; and SU5416, a tyrosine kinase inhibitor (TKI). Preferably, the agent for promotion of angiogenesis is VEGF and the inhibitor is anti-VEGF antibody. In one aspect, the agent and the inhibitor are encapsulated.

Angiogenesis is induced in a subject in need thereof at a site in need of angiogenesis, e.g., ischemic tissue, a narrowed or occluded vascular conduit, or an injured vascular tissue. The narrowed or occluded vascular conduit is a narrowed or occluded artery, narrowed or occluded vein, or a narrowed or occluded synthetic graft. Angiogenesis is induced in a mammalian subject. Preferably, the subject is a human.

Regeneration can be temporally and spatially (directionally) controlled by simultaneously delivering from a single source/location stimulatory and inhibitory agents that are spatially segregated. Specifically, the invention also provides a method of inducing regeneration in a spatially restricted zone by contacting a target site with an agent that promotes regeneration and contacting a target site with an inhibitor of regeneration. In one aspect, the inhibitor of regeneration is a specific inhibitor of the agent that promotes regeneration. In another aspect, the inhibitor of regeneration is a general inhibitor of regeneration. Preferably, the agent and the inhibitor are administered simultaneously. Optionally, the agent and the inhibitor are incorporated in or on a device comprising a scaffold composition. The agent and the inhibitor are spatially segregated in or on the scaffold composition. Alternatively, the agent and inhibitor are injected directly into the tissue, e.g., an artery. The simultaneous delivery of agents and agent inhibitors maintains the temporal stability of the active agent concentration profile.

Also provided are methods of temporally and spatially (directionally) controlling regenerative processes by simultaneously delivering from a single source/location agents that act synergistically rather than antagonistically to create spatial patterns/control.

As described herein, the invention provides for in vivo and in vitro temporal and spatial control of regenerative processes, e.g., tissue regeneration, organ regeneration, cartilage regeneration, bone regeneration, or neural regeneration. The inhibitor of regeneration is a specific inhibitor of the agent that promotes regeneration. Alternatively, the inhibitor of regeneration is a general inhibitor of regeneration. In one aspect, the regeneration is bone regeneration, and the agent that promotes bone regeneration is transforming growth factor-β (TGF-β), bone morphogenetic protein (BMP), insulin-like growth factor (IGF-1), fibroblast growth factor-2 (FGF-2), or platelet-derived growth factor (PDGF). Suitable inhibitors of bone regeneration include anti-TGF-β antibody, anti-BMP antibody, anti-IGF-1 antibody, anti-FGF-2 antibody, and anti-PDGF antibody. Other suitable inhibitors of bone regeneration include noggin, follistatin, chordin, sclerostin, differential screening-selected gene aberrative in neuroblastoma (DAN), protein related to DAN and cerberus (PRDC), follistatin-related protein (FSRP), and Dante. In another aspect, the regeneration is tissue regeneration, and the agent that promotes tissue regeneration is epidermal growth factor (EGF), platelet-derived growth factor (PDGF), transforming growth factor-α (TGF-α) or VEGF, and the inhibitor of tissue regeneration is anti-EGF antibody, anti-PDGF antibody, anti-TGF-α antibody, or anti-VEGF antibody, respectively. In yet another aspect, the regeneration is neural regeneration of the peripheral or central nervous system, and the agent that promotes neural regeneration is nerve growth factor (NGF), brain-derived neurotrophic factor (BDNF), neurotrophin-3 (NT-3), ciliary neurotrophic factor (CNTF), or glial cell line-derived neurotrophic factor (GDNF). Optionally, the regeneration is induced in a mammal. Preferably, the mammal is a human.

The invention provides for methods for inducing cell differentiation/specialization in a spatially restricted zone by contacting a cell with a promoter of differentiation and an inhibitor of differentiation. The agent and the inhibitor interact, thereby inducing cell differentiation in a spatially restricted zone at or near a site at which the agent and the inhibitor interact. Optionally, the agent and the inhibitor are administered simultaneously. In one aspect, the agent and the inhibitor are incorporated in or on a device comprising a scaffold composition. The agent and the inhibitor are spatially segregated in or on said scaffold composition. The simultaneous delivery of agents and agent inhibitors maintains the temporal stability of the active agent concentration profile. Suitable combinations of agents to promote differentiation of stem cells into bone cells or tooth cells include BMP4 and anti-BMP4. Suitable combinations of agents to promote differentiation of stem cells into dentin include TGF-β1 and latency associated peptide (LAP).

Also provided are methods for selectively destroying tissue in a spatially restricted zone comprising contacting a target site with an agent that promotes tissue destruction and an inhibitor of tissue destruction. The agent and the inhibitor interact thereby selectively destroying tissue in a spatially restricted zone at or near a site at which the agent and the inhibitor interact. For example, a device that contains a small molecule, e.g., like SC68896 (small molecule proteosome inhibitor) that up regulates expression of cell death receptors such as tumor necrosis factor-related apoptosis-inducing ligand (TRAIL) receptor such as cell death receptors 4 (DR4) and 5 (DR5) and the ligand, TNFα, sensitizes local tumor cells to apoptotic signals (Clin Cancer Res 2009; 15(21):6609-18, hereby incorporated by reference). In this example, the scaffold device contains a primary molecule (SC68896) that leads to up regulation of cell death receptors of infiltrating tumor cells, and a tissue destruction molecule (TNFα) which subsequently induces tumor cell death of those primed tumor cells. Thus, method for selectively destroying tissue in a spatially restricted zone is carried out by contacting a target site a device containing an agent that promotes tissue destruction and an inhibitor of the tissue destruction agent or a tissue destruction primer (e.g., SC68896, described above). The agent and the inhibitor or primer contact a cell inside the device at or near target site (e.g., a tumor) leading to selective destruction of cell, e.g., a tumor cell) in a spatially restricted zone at or near a site at which the agent and the inhibitor interact. Such a device is also useful to treat cancers of the circulatory system such as leukemias. Circulating cells enter the device and are primed and subsequently encounter an apoptosis signal (TNFα) leading to destruction of the cancer cell.

Also within the invention is a polymeric device that comprises at least 2 spatially distinct zones. The first zone comprises a purified morphogen, and a second zone comprises an antagonist of the morphogen and/or a second morphogen. The device optionally contains 3, 4, 5 or more morphogens in spatially divided or distinct areas or zones, e.g., the device includes, 2, 3, 4, 5, or more layers. Optionally, one or more of the layers is a buffer zone/layer. A buffer layer contains an a non-morphogenic compound or is empty, i.e., is defined by the area or zone of the polymeric device but has not been loaded with an morphogen or inhibitor/antagonist. The zones are stacked or in a core/shell configuration. The distinct zones are contiguous in the geometry of the scaffold device.

In some examples, the composition or device comprises at least two purified morphogens and at least two purified morphogen inhibitors, e.g., TGF-β1 and BMP4, and their respective inhibitors anti-TGF-β1 antibody and an anti-BMP4 antibody. In another example, the purified morphogen comprises Latent TGF-B1 and the purified inhibitor of said morphogen comprises a small molecule inhibitor SB431542.

The device optionally further comprises purified cells or purified populations of cells. For example, the device is administered to the patient pre-seeded with cells or empty, i.e., cell-free. In the latter case, cells of the patient populate the device after implantation into or onto the body of the subject. For cell differentiation devices, exemplary cells include mesenchymal stem cells, embryonic stem cells, or induced pluripotent stem cells. The devices are particularly useful to promote a morphogenic process that comprises differentiation of cells into at least two different tissue types, e.g., to generate or regenerate a site of two juxtaposed tissues. Examples include tooth regeneration, lung regeneration, liver regeneration, kidney regeneration, cardiac valve regeneration, joint regeneration, or pancreas regeneration.

The a variation of the above-described strategy of delivering stimulatory agents and antagonist or inhibitor agents includes a method for promoting a morphogenic process that includes the steps of administering to a subject a first device comprising a purified morphogen at a first anatomical site and a second device comprising an antagonist of the morphogen at a second anatomical site. In this example, the first device and second (or additional) device(s) are non-contiguous. The factor-loaded devices are implanted or injected (e.g., in the case of a gel) at different physical locations in the body. The area between the first and second implantation or injection sites defines a zone of interaction between the morphogen and antagonist and the morphogenic process occurs in the zone of interaction.

As described herein, the term "controlled release" refers to an agent-containing formulation or fraction thereof in which release of the agent is not immediate, i.e., with a "controlled release" formulation, administration does not result in immediate release of the agent into an absorption pool. The term is used interchangeably with "nonimmediate release" as defined in Remington: The Science and Practice of Pharmacy, Nineteenth Ed. (Easton, Pa.: Mack Publishing Company, 1995). In general, the term "controlled release" as used herein refers to "sustained release" rather than to "delayed release" formulations. The term "sustained release" (synonymous with "extended release") is used in its conventional sense to refer to a formulation that provides for gradual release of an agent over an extended period of time.

All polynucleotides and polypeptides of the invention are purified and/or isolated. Purified defines a degree of sterility that is safe for administration to a human subject, e.g., lacking infectious or toxic agents. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

By the terms "effective amount" and "therapeutically effective amount" of a formulation or formulation component is meant a nontoxic but sufficient amount of the formulation or component to provide the desired effect.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIG. 1 is a series of photomicrographs showing in vitro endothelial cell sprouting in response to anti-vascular endothelial growth factor (VEGF) and VEGF.

FIG. 3 is a series of schematic diagrams and graphs that illustrate results from computational simulation of an AVA implanted scaffold, i.e., tri-layered scaffolds with a VEGF-containing layer sandwiched by two anti-VEGF-containing layers. FIG. 3 also shows the simulation results of the concentration profiles of (b) total VEGF, (c) free VEGF, and (d) free anti-VEGF over time at y=0 and z=−0.5 mm. FIG. 3g demonstrates the peaks of total VEGF and free VEGF over time, while

Finally.

FIG. 4 is a series of photomicrographs and a bar graph illustrating blood vessel densities within layered scaffolds 4 weeks post-implantation (n=5). FIG. 4b demonstrates the quantification of vessel densities within each layer of implanted scaffolds (*p≤0.05, p≤0.01, *p≤0.001). Values represent mean and error bars represent standard deviations (n=5).

FIG. 5 is a series of photomicrographs and a bar graph illustrating blood vessel densities within muscle tissue sections (n=5) directly underneath the corresponding scaffold layer.

FIG. 19 is a series of diagrams showing normal joint histology and a scaffold system for joint implants.

FIG. 20 is a series of schematics demonstrating endochondral and intramembranous ossification and a scaffold system for spinal implants.

Subsequently, for given amounts of time, the inhibitor is washed off, the growth factor (either TGF-β1 or BMP4) is added for specified time, and washed off followed by re-addition of the inhibitor. At 24 hours, cells are lysed and assayed for luciferase activity.

Figure 22A:
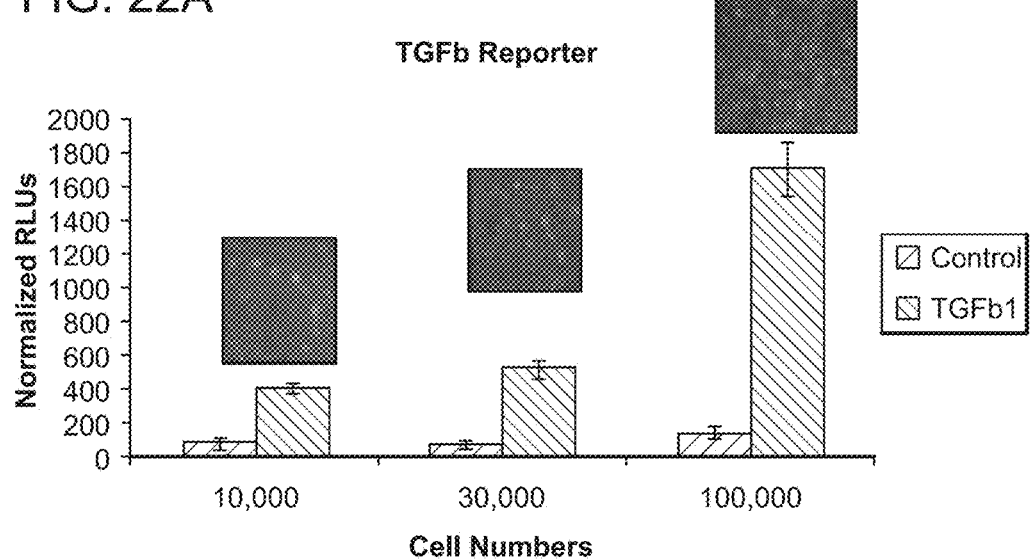
FIG. 22A is a bar chart showing the effect of cell density of the TGF-β reporter line (MLEC p3TP Luc) luciferase activity and demonstrates the ability to be induced in a dose dependent manner.
Figure 22B:
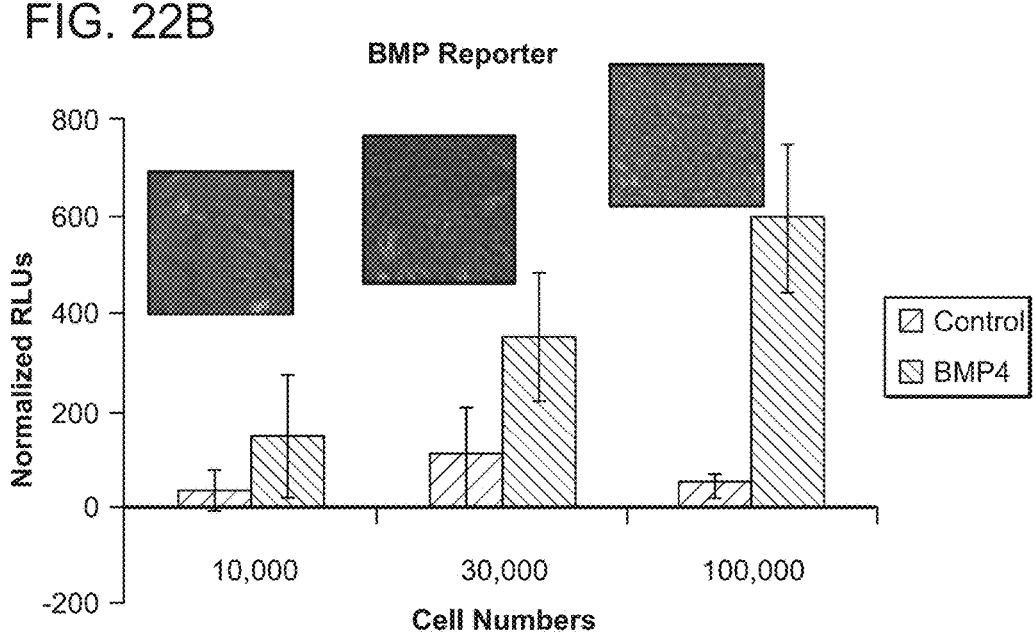
FIG. 22B is a bar chart showing the effect of cell density of BMP4 reporter (C2C12 BRE Luc) luciferase activity and demonstrates the ability to be induced in a dose dependent manner.
Figure 22C:
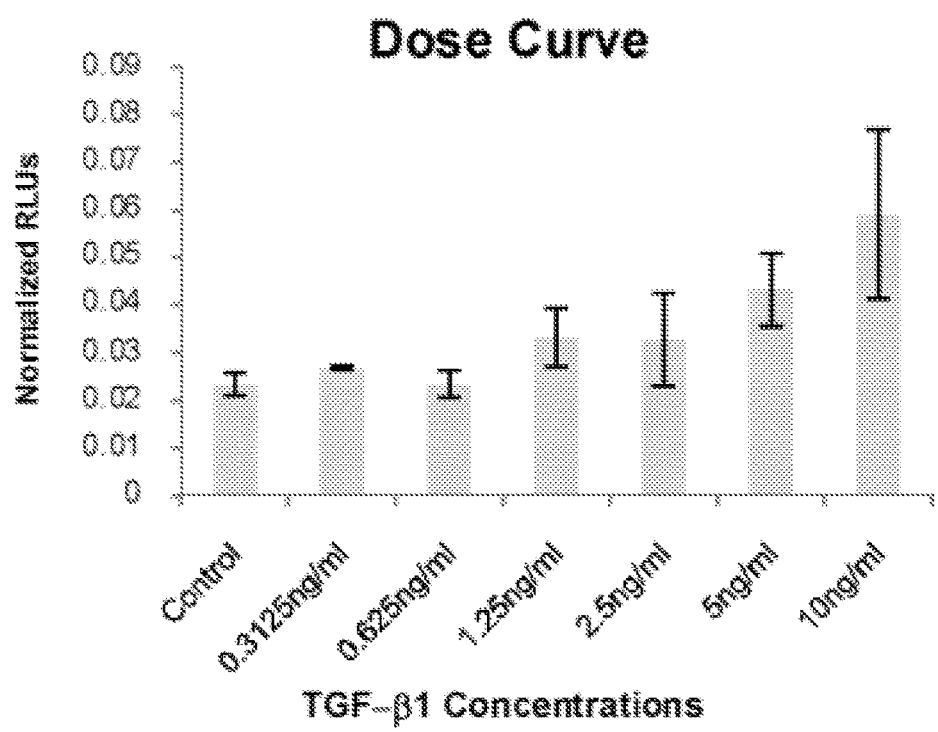
FIG. 22C is a bar chart showing the effect of varying TGF-β1 concentration on the TGF-β reporter line (MLEC p3TP Luc) luciferase activity and demonstrates a linear dose dependence.
Figure 22D:
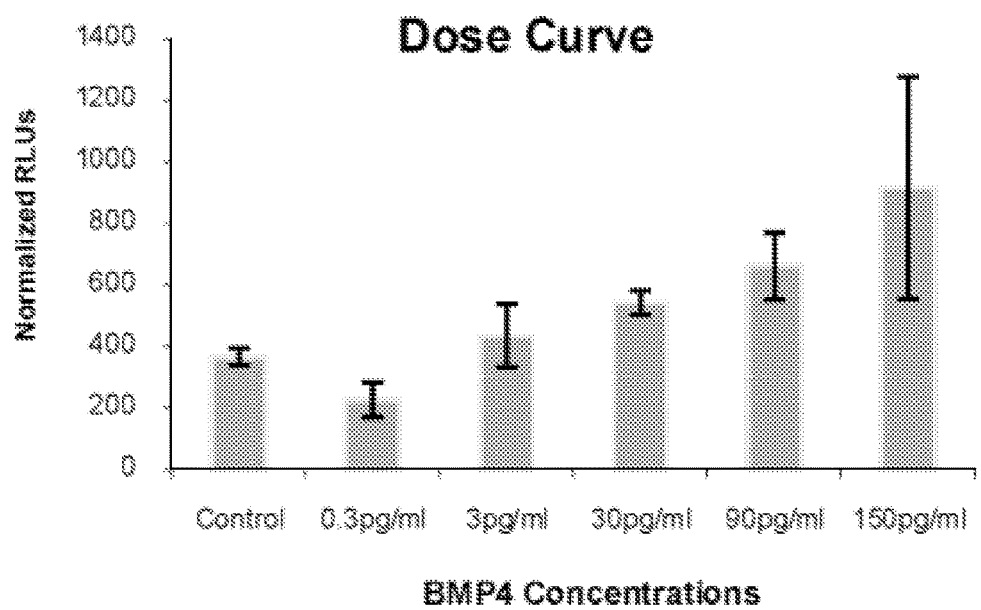
FIG. 22D is a bar chart showing the effect of varying BMP4 concentration on the BMP4 reporter (C2C12 BRE Luc) luciferase activity and demonstrates a linear dose dependence.
Figure 22E:
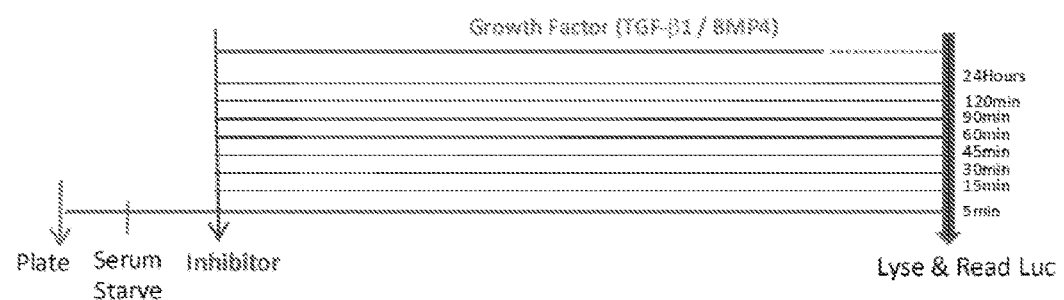
FIG. 22E is a schematic showing an experimental scheme to show the precise kinetics of growth factor exposure on luciferase activity in the reporter lines. Following seeding and serum starvation (reduces background), a specific inhibitor is added to create a uniform inhibitory field.
Figure 22F:
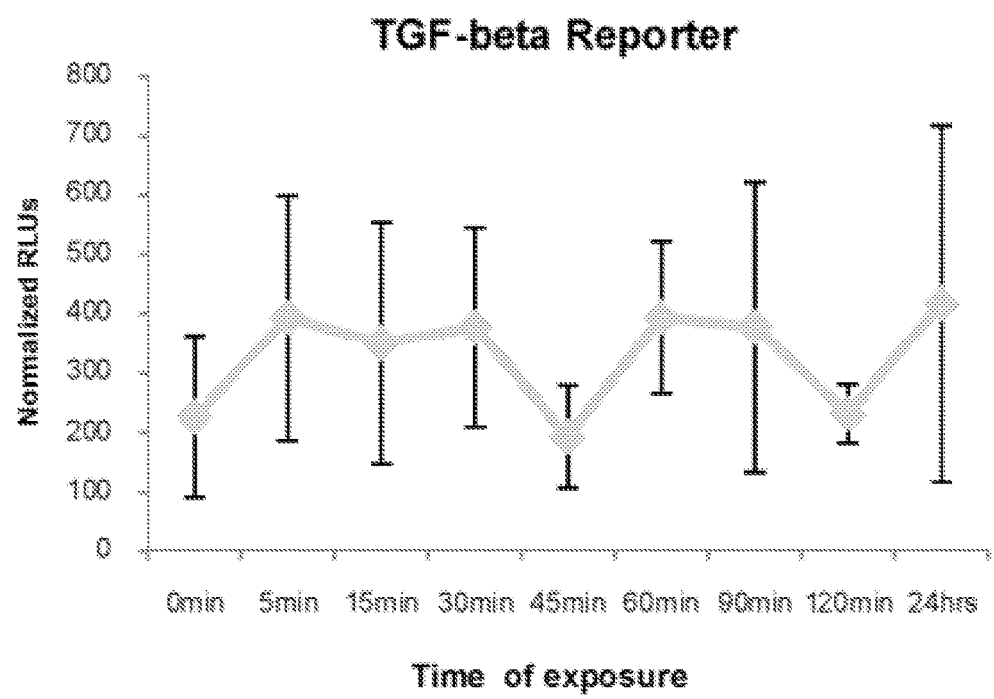

FIG. 22F is a line graph showing luciferase activity and demonstrates the sufficiency of 5-15 min TGF-β1 exposure for maximal induction.

Figure 22G:
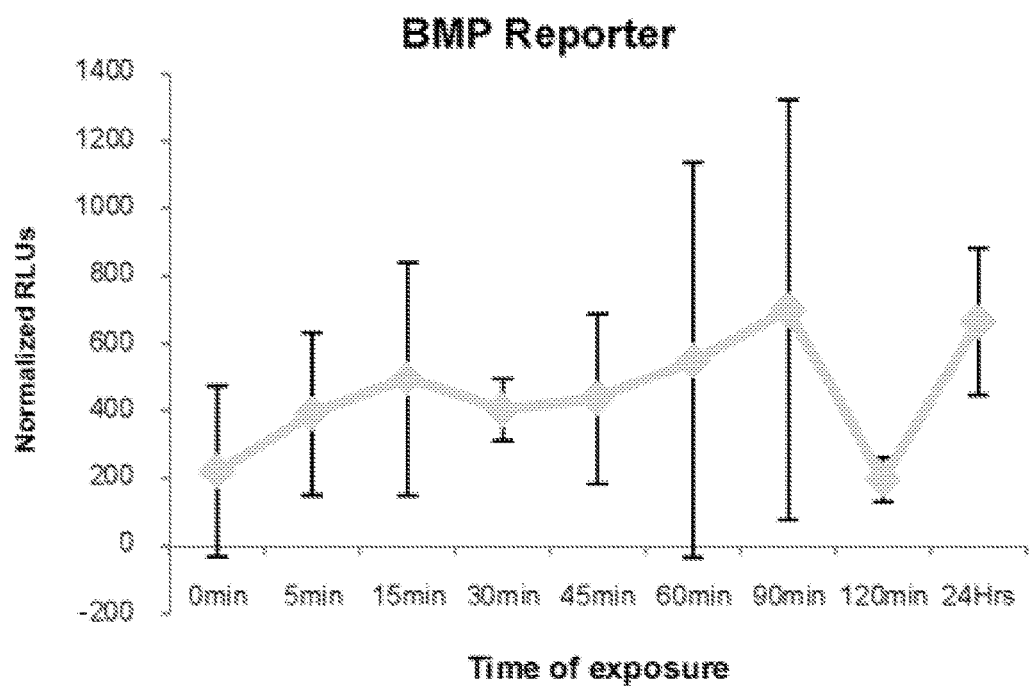

FIG. 22G is a line graph showing luciferase activity demonstrating the sufficiency of 5-15 min BMP4 exposure for maximal induction.

Figure 23A:
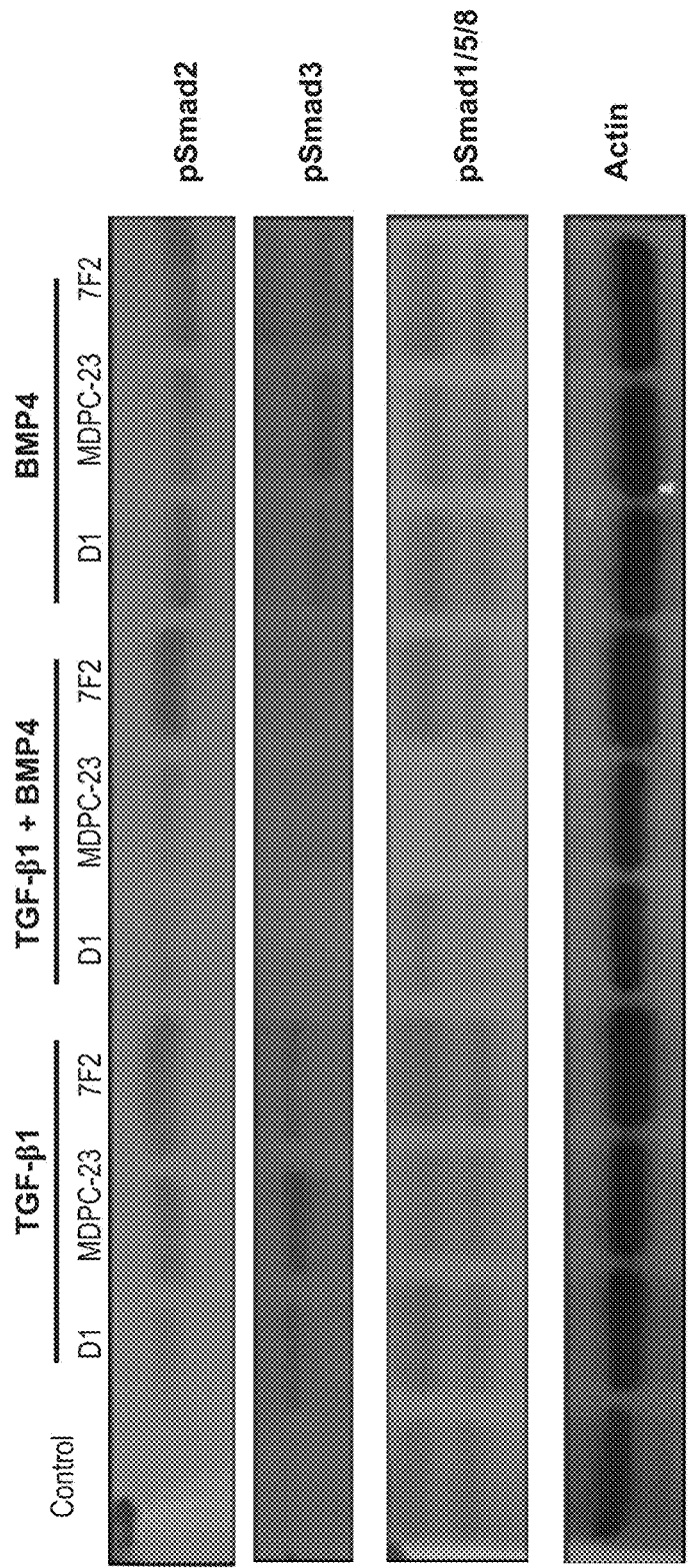
Figure 23B:
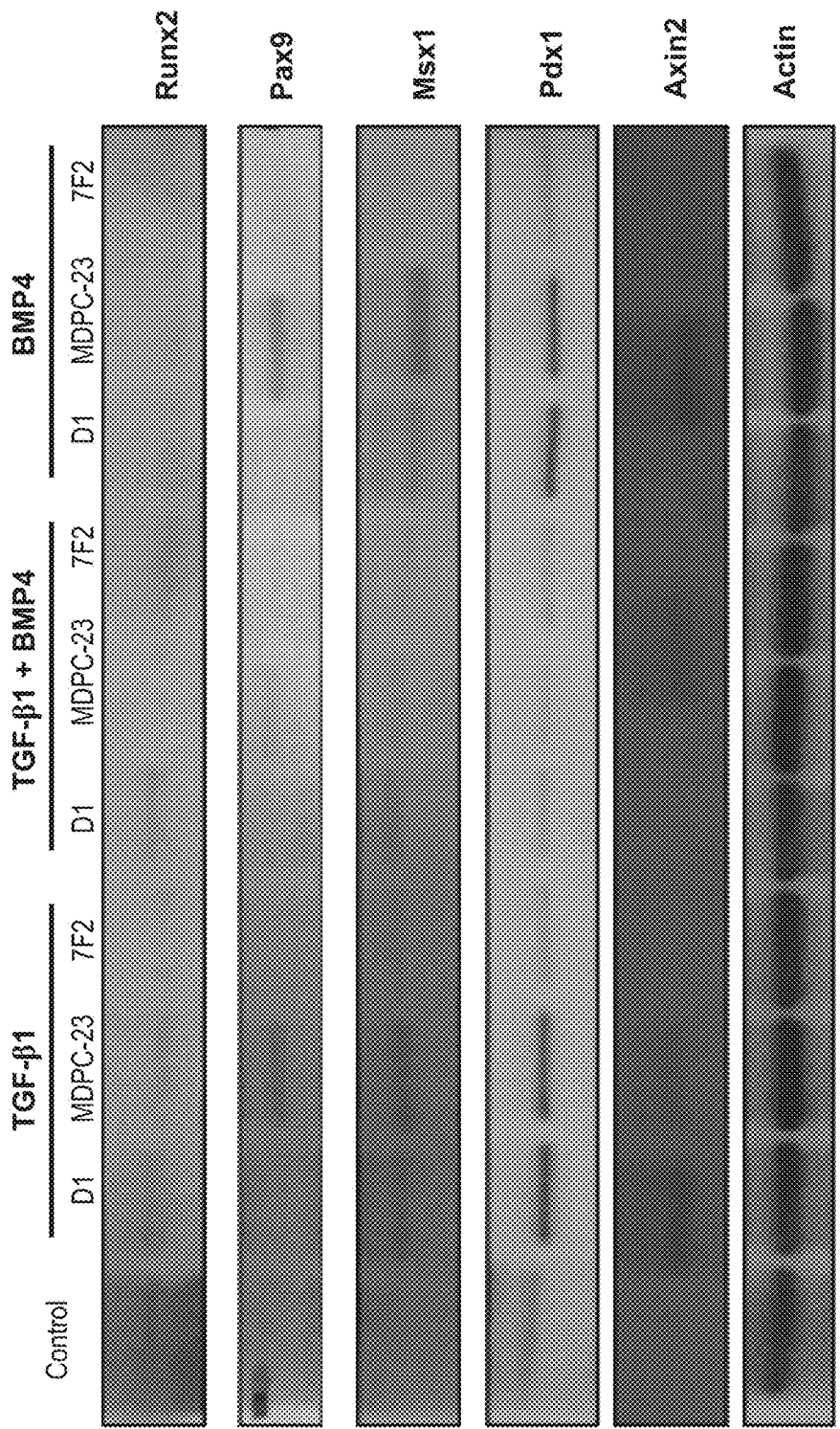
Figure 23C:
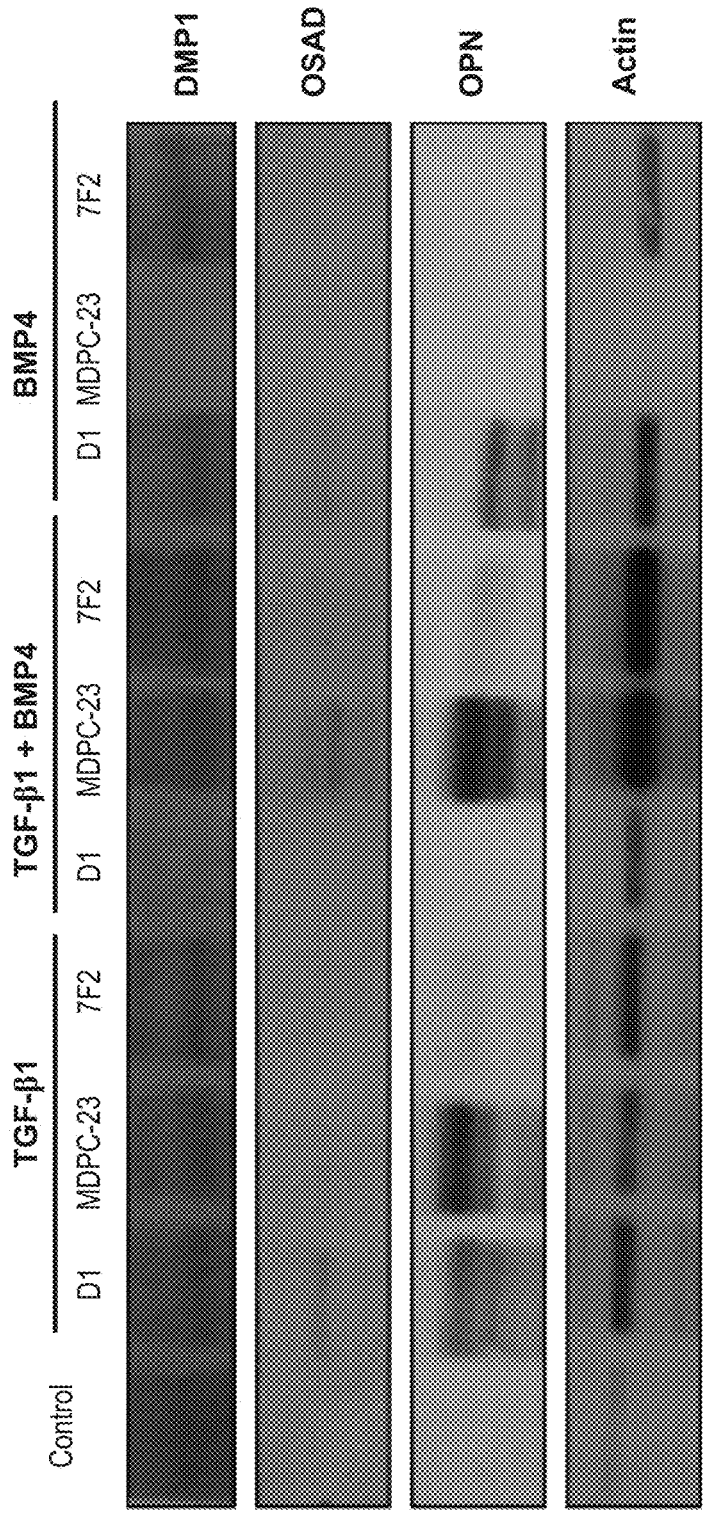

FIG. 23 is a series of photograph demonstrating immunoblotting on MSC (D1), pre-odontoblasts (MDPC-23) and osteoblasts (7F2) with TGF-β1, BMP4 and both together to evaluate their influence on canonical signaling pathways (A) for TGF-β (Phospho Smad2 & 3) and BMP (Phospho Smad1/5/8) as well as bone and teeth transcription factors (B) and extracellular matrix deposition (C).

DETAILED DESCRIPTION

Regenerative medical technologies are devices and methods that repair or replace diseased or defective tissues or organs. Tissue engineering is the application of the principles and methods of engineering and the life sciences to the development of biological substitutes to restore, maintain or improve function of bodily structures and tissues, or to selectively promote the destruction of undesired tissues. It involves the development of methods to build biological substitutes as supplements or alternatives to whole organ or tissue transplantation, or the development of strategies to manipulate tissues in vivo. The methods of the invention are useful to generate functional biological structure de novo or to regenerate organs in situ, as well as to restore or supplement tissue function.

Nature frequently utilizes opposing factors to create a stable activator gradient to robustly control pattern formation. Specifically, during developmental processes, tight spatial regulation often results from the combined action of stimulatory and inhibitory factors (Barrio et al., 1999 Bull Math Biol 61, 483-505; Faissner, A., and Steindler, D. 1995 Glia 13, 233-254; Maini, P. K. 1989 J Math Biol 27, 507-522). Diffusion/reaction of stimulatory factors alone results in formation of shallow gradients that make cellular discrimination of spatial cues difficult. By contrast, it has long been appreciated that sharp cut-offs can result from Turing's reaction diffusion mechanism, where an inhibitor and activator act together to form distinct patterns (Turing, A. M. 1952 Philosophical Transactions of the Royal Society of London Series B-Biological Sciences 237, 37-72; Turing, A. M. 1990 The chemical basis of morphogenesis. 1953, Bull Math Biol 52, 153-197; discussion 119-152; Harrison, L. G. 1987 J Theor Biol 125, 369-384). In such reaction schemes, the reactions of morphogens and their diffusion through a tissue are adequate in describing morphogenesis and creating sharp boundaries in patterns. Prior to the invention described herein, the art-recognized strategy for delivering stimulatory factors alone to promote regeneration has ignored this fundamental principle of developmental biology.

Angiogenesis is a physiological process involving the growth and development of new blood vessels from pre-existing vessels. Prior to the invention described herein, much of the effort in therapeutic angiogenesis has been focused on the delivery of growth factors to restore blood perfusion; however, current delivery techniques often lead to supraphysiologic growth factor concentrations and undirected vessel growth. Such over-stimulation can result in improperly organized vascular networks and other pathological effects which reduce perfusion. As such, there has been a long-felt need in the art for the discovery of new approaches to achieve temporally stable and spatially restricted angiogenesis to allow for the creation of heterogeneous and functional vasculature. Described herein are studies that employ a biomimicry approach, by delivery of both angiogenic and anti-angiogenic factors from spatially restricted zones of a synthetic polymer to achieve temporally stable and spatially restricted angiogenic zones in vivo. However, the invention is not limited to angiogenesis and can also be applied to other drug delivery applications in order to mitigate the negative effects of initial bursts.

The invention is based on the discovery that the simultaneous release of two spatially separated agents leads to a spatially sharp angiogenic region that is sustained over 4 weeks. Further, the contradictory action of the two agents leads to a stable level of pro-angiogenic stimulation in this region, in spite of significant variations in the individual release rates over time. The resulting spatially restrictive and temporally sustained profiles of active signaling allow the creation of a spatially heterogeneous and functional vasculature.

Bioactive Agents

Bioactive compositions are purified naturally-occurring, synthetically produced, or recombinant compounds, e.g., polypeptides, nucleic acids, small molecules, or other agents. The compositions described herein are purified. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

The bioactive composition alters a function, e.g., level of differentiation, state of activation, motility, or gene expression, of a cell. Optionally, bioactive agents that influence growth, development, movement, and other cellular functions are introduced into or onto scaffold structures. Such substances include BMP, bone morphogenetic protein; ECM, extracellular matrix proteins or fragments thereof; EGF, epidermal growth factor; FGF-2, fibroblast growth factor 2; NGF, nerve growth factor; PDGF, platelet-derived growth factor; PlGF, placental growth factor; TGF, transforming growth factor, and VEGF, vascular endothelial growth factor. Cell-cell adhesion molecules (cadherins, integrins, ALCAM, NCAM, proteases) are optionally added to the scaffold composition.

Exemplary growth factors and ligands are provided in the tables below.

Growth Factors Used for Angiogenesis

| Growth factor | Abbreviation | Relevant activities |
|---|---|---|
| Vascular endothelial growth factor | VEGF | Migration, proliferation and survival of ECs |
| Basic fibroblast growth factor | bFGF-2 | Migration, proliferation and survival of ECs and many other cell types |
| Platelet-derived growth factor | PDGF | Promotes the maturation of blood vessels by the recruitment of smooth muscle cells |
| Angiopoietin-1 | Ang-1 | Strengthens EC-smooth muscle cell interaction |

-continued

| Growth factor | Abbreviation | Relevant activities |
|---|---|---|
| Angiopoietin-2 | Ang-2 | Weakens EC-smooth muscle cell interaction |
| Placental growth factor | PlGF | Stimulates angiogenesis |
| Transforming growth factor | TGF | Stabilizes new blood vessels by promoting matrix deposition |

For example, VEGF and PDGF is a suitable combination of agents to promote sustained angiogenesis in a spatially restricted zone (Chen et al., 2006 Pharmaceutical Research, 24(2): 258-264; incorporated herein by reference).

Anti-Angiogenic and Anti-Vascular Agents

Drugs Currently in Clinical Trials and their Effects on Vascular Endothelial Cells

| Type of Agent | Target Cells | Molecular Targets | Description |
|---|---|---|---|
| Antiangiogenic Agents | | | |
| RhuMabVEGEF (bevacizumab)* | ECs | VEGF-A | Monoclonal antibody to VEGF |
| VEGF-Trap | ECs | VEGFps | Composite fusion protein of VEGFR-1 and -2 with Fc fragment of IgG |
| BAY 43-9006 | ECs, tumor cells | VEGFR Rafkinase c-kit | Small molecule receptor TKI |
| SU11248 (sunitinib)* | ECs, pericytes | VEGFRs, PDGFR-β, CSF-1R | Small-molecule receptor TKI |
| ZO6474 (vandetanb) | ECs, tumor cells | VEGFR-2, EGFR | Small-molecule receptor TKI |
| PTK787/ZK 222584 (vatalarib) | ECs | VEGFRs, PDFGR | Small-molecule receptor TKI |
| AZD2171 (codiranib) | ECs, tumor cells | VEGFR-2, PDGFRs | Small-molecule multikinase inhibitor |
| GW786034 (pezopanib) | ECs pericytes | VEGFR, PDGFRs, c-kit | Small-molecule multikinase inhibitor |
| AG013736 | ECs, pericytes | VEGFR, EGFR, Erb82, c-src, c-abi, c-tnos, Flt-1 | Small-molecule multikinase inhibitor |
| AMG706 | ECs | VEGFRs, PDGFR, c-kit | Small-molecule multikinase inhibitor |
| BMS-582664 (brivanti) | ECs | VEGFRs, bFGFRs | Small-molecule multikinase inhibitor |
| PI-88 | ECs Inflammatory cells | VEGF, bFGFs | Small molecule inhibiting haparanase activity and herperin-binding growth factors |
| M200 (volociximab) | ECs, ECM | Integrins αvβ1 | Monoclonal antibody to α5β1 integrin |
| CNTO 95 | ECs, ECM | Integins αv | Monoclonal antibody to αv integrin |
| EMD 121974 (cilengitide) | ECs, ECM | Integrins αvβ3, αvβ5 | Synthetic peptide RGDMV |
| ATN-161 | ECs, ECM | Integrin αvβ1 | Synthetic peptide/Ac—PHSCN—NH(2) |
| ADH-1 (extherin) | ECs, tumor cells | N-cadherin | Synthetic peptide sequence recognizing cadherin (affects cell adhesion) |
| ABT-510 | ECs | CD36 receptor | Synthetic peptidr/thrombospondin-1 nanlog |
| Antivasular Agents Ligand-Directed Agents | | | |
| Fusion proteins of the antibody, L19, with IL 2 (L19-IL2) | ECs, ECM | Extra domain B of fibronectin | Antibody fragment-directed IL-2 |
| Radiolabeled antibody fragments from the L19 (1311-L19) | ECs, ECM | Extra-domain B of fibronectin | Antibody fragment-directed radioiscope |
| Radiolabeled monoclonal antibody, J591 (111In-J591) | ECs | Prostate-specific membrane antigen | Antibody-directed radioiscope |
| CNGRC peptide-TNFα conjugate (NGR-TNF) | ECs | CD13, Integrin | Peptide-directed TNF |
| Vascular-Disrupting Agents | | | |
| Combretastatin A4 phosphate | ECs | Unknown | Small-molecule microtubule-depolymerization agent |
| dimethylxanthenone acetic acid | ECs | Unknown | Small-molecule cytokine-inducing agent |

*Approved by the US Food and drug Administration.

Growth Factors Used for Bone Regeneration

| Growth factor | Abbreviation | Relevant activities |
|---|---|---|
| Transforming growth factor-β | TGF-β | Proliferation and differentiation of bone-forming cells |
| Bone morphogenetic protein | BMP | Differentiation of bone-forming cells |
| Insulin-like growth factor | IGF-1 | Stimulates proliferation of osteoblasts and the synthesis of bone matrix |
| Fibroblast growth factor-2 | FGF-2 | Proliferation of osteoblasts |
| Platelet-derived growth factor | PDGF | Proliferation of osteoblasts |

Growth Factors Used for Wound Healing

| Growth Factor | Abbreviation | Relevant activities |
|---|---|---|
| Platelet-derived growth factor | PDGF | Active in all stages of healing process |
| Epidermal growth factor | EGF | Mitogenic for keratinocytes |
| Transforming growth factor-β | TGF-β | Promotes keratinocyte migration, ECM synthesis and remodeling, and differentiation of epithelial cells |
| Fibroblast growth factor | FGF | General stimulant for wound healing |

Growth Factors Used for Tissue-Engineering

| Growth factor | Abbreviation | Molecular weight (kDa) | Relevant activities | Representative supplier of rH growth factor |
|---|---|---|---|---|
| Epidermal growth factor | EGF | 6.2 | Proliferation of epithelial, mesenchymal, and fibroblast cells | PeproTech Inc. (Rocky Hill, NJ, USA) |
| Platelet-derived growth factor | PDGF-AA | 28.5 | Proliferation and chemoattractant agent for smooth muscle cells; extracellular matrix synthesis and deposition | PeproTech Inc. |
| | PDGF-AB | 25.5 | | |
| | PDGF-BB | 24.3 | | |
| Transforming growth factor-α | TFG-α | 5.5 | Migration and proliferation of keratinocytes; extracellular matrix synthesis and deposition | PeproTech Inc. |
| Transforming growth factor-β | TGF-β | 25.0 | Proliferation and differentiation of bone forming cells; chemoattractant for fibroblasts | PeproTech Inc. |
| Bone morphogenetic protein | BMP-2 | 26.0 | Differentiation and migration of bone forming cells | Cell Sciences Inc. (Norwood, MA, USA) |
| | BMP-7 | 31.5 | | |
| Basic fibroblast growth factor | bFGF/FGF-2 | 17.2 | Proliferation of fibroblasts and initiation of angiogenesis | PeproTech Inc. |
| Vascular endothelial growth factor | VEGF$_{165}$ | 38.2 | Migration, proliferation, and survival of endothelial cells | PeproTech Inc. | rH, recombinant human

Factors Used in Epithelial Patterning

TABLE 1

Regulation of epithelial growth, differentiation and apoptosis

| Soluble factors | Cells expressed | Responding cells | Possible role |
|---|---|---|---|
| HGF and MSP | Fibroblasts | Epithelia | + Proliferation<br>+ Transformation<br>+ Morphogenic |
| IGF-1, IGF-2 | Fibroblast | Epithelia (breast) | − Apoptosis<br>+ Proliferation |
| EGF and TGF-α | Epithelia and fibroblasts | Epithelia | + Proliferation<br>+ Morphogenic |
| TGF-β1, TGF-β2, TGF-β3 | Epithelia and fibroblasts | Epithelia and fibroblasts | − Proliferation<br>+/− Apoptosis<br>+ Morphogenic |
| FGF7/KGF | Fibroblast | Epithelia | + Proliferation<br>+ Morphogenic |
| IL6, LIF, and oncostatin M | Fibroblast | Epithelia (colonic) | + Proliferation<br>+ Transformation |
| FGF2 | Fibroblast | Epithelia | + Proliferation<br>+ Transformation |
| FGF10 | Fibroblast | Epithelia | + Proliferation |
| NGF | Fibroblast | Epithelia | + Transformation |
| Stromal cell-derived factor 1α (CXCL12) | Fibroblast | Epithelia (glioblastoma) | + Proliferation<br>+ Transformation |
| Wnt1, Wnt3 | Fibroblast | Epithelia | + Proliferation<br>+ Transformation |
| MMP-1, MMP-7 | Fibroblast | ECM and growth-factor activation in the stroma affect epithelia | +/− Proliferation<br>+/− Apoptosis<br>+ Morphogenic |

IL6, interleukin 6; LIF, leukaemia inhibitory factor; NGF, nerve growth factor.

Neurotrophic factors are a family of proteins that are responsible for the growth and survival of developing neurons and the maintenance of mature neurons. Neurotrophic factors promote the initial growth and development of neurons in the central nervous system (CNS) and peripheral nervous system (PNS). Most neurotrophic factors belong to one of three families: (1) neurotrophins, (2) glial cell-line derived neurotrophic factor family ligands (GFLs), and (3) neuropoietic cytokines. Exemplary neurotrophic factors are provided in the table below.

Neurotrophic Factors

| Neural response promoted | Neurotrophic factors |
|---|---|
| Motor neuron survival | BDNF, NT-3, NT-4/5, CNTF, GDNF |
| Motor neuron outgrowth | BDNF, NT-3, NT-4/5, CNTF, GDNF |
| Sensory neuron survival | NGF, NT-4/5, GDNF |
| Sensory neuron outgrowth | NGF, BDNF, NT-3 |
| Spinal card regeneration | NGF, NT-3, CNTF, FGFs |
| Peripheral nerve regeneration | NGF, NT-3, NT-4/5, CNTF, GDNF, FGFs |
| Sensory nerve growth across the PNS-CNS transition zone | NGF, NT-3, GDNF, FGFs |

Abbreviations: Brain-derived neurotrophic factor (BDNF), neurotrophin-3 (NT-3), neurotrophin-4/5 (NT-4/5), ciliary neurotrophic factor (CNTF), glial cell line-derived growth factor (GDNF), nerve growth factor (NGF), acidic and basic fibroblast growth factors (FGFs).

The invention also provides factors that are involved in the patterning of the peripheral and central nervous system, e.g., sonic hedgehog and anti-sonic hedgehog antibody. Other suitable factors involved in the patterning of the peripheral and central nervous system are provided in the table below.

Major Neurotrophic Factors Derived from Glial Cells

| | ASTROCYTE | MICROGLIA |
|---|---|---|
| Neurotrophin | | |
| NGF | + | + |
| BDNF | + | + |
| NT-3 | + | + |
| NT-4/5 | + | + |
| Cytokine | | |
| IL-1 | + | + |
| IL-2 | + | (?) |
| IL-3 | | + |
| IL-6 | + | + |
| CNTF | + | |
| TGF-β | + | + |
| GDNF | + | + |
| Neurturin | + | |
| Persephin | + | |
| TNF-α | + | + |
| Growth factor | | |
| bFGF | + | + |
| IGF-I, -II | + | + |
| HGF | | + |
| Protease, Protease inhibitor | | |
| Plasminogen (plasmin) | | + |
| GDN | + | |
| α-2M | + | |
| Calcium binding protein | | |
| S-100 β | + | |
| Annexin V | + | + |

Abbreviations: NGF, nerve growth factor; BDNF, brain-derived neurotrophic factor; NT-3, neurotrophin-3; IL, interleukin; CNTF, ciliary neurotrophic factor; TGF, transforming growth factor; GDNF, glial cell line-derived neurotrophic factor; TNF, tumor necrosis factor; bFGF, basic fibroblast growth factor; IGF, insulin-like growth factor; HGF, hepatocyte growth factor; GDN, glia-derived neurite promoting factor; α-2M, α 2-macroglobulin.

Molecules that can modulate the signaling pathways of growth factors, such as Notch activators (e.g., jagged, DH, and serrate) and Notch inhibitors (e.g., anti-jagged, anti-DII, and N-[(3,5-Difluorophenyl)acetyl]-L-alanyl-2-phenyl]glycine-1,1-dimethylethyl ester (DAPT)) can also be used to augment or diminish the angiogenesis process. Notch is a cell-surface receptor that regulates cell fate decisions throughout development and under selected conditions in adult tissues. Notch signaling results in widely variable outcomes depending on the cells and signaling molecules involved. However, it is generally known that binding of Notch ligands of the Delta and Jagged families results in the proteolytic cleavage of Notch. The Notch protein is first cleaved in the extracellular domain and then subsequently cleaved in the transmembrane domain. The second cleavage event is mediated by γ-secretase. Notch cleavage allows the intracellular domain of the receptor (the Notch IntraCellular Domain, NICD) to translocate to the nucleus where it regulates transcription. Thus, γ-secretase is a Notch activator.

Notch signaling is involved in angiogenesis and vascular remodeling. Moreover, Notch signaling regulates endothelial cell proliferation and migration events necessary to form new blood vessels during angiogenesis in normal tissues as well as malignant tumors. Methods of the present invention are drawn towards inducing angiogenesis in normal tissues, not malignant tissues. Furthermore, it is of great importance to avoid inducing a malignant-state within a stable or benign tumor by introducing pro-angiogenic factors in the absence of factors to limit Notch activation. In one embodiment of the present invention, pro-angiogenic factors are released from compositions, scaffolds, or devices, either simultaneously or sequentially, with notch-inhibitors, e.g., inhibitors of gamma-secretase (γ-secretase), to prevent stimulation of angiogenesis within neoplastic tissue.

Compositions, scaffolds, and devices of the present invention comprise all inhibitors of Notch activation to be released simultaneously or sequentially with pro-angiogenic factors. Inhibitors of Notch activity encompassed by the present invention block binding of one or more ligands to the Notch receptor. Alternatively, or in addition, inhibitors of Notch activity present intracellular signal transduction from the Notch receptor or cleavage of the Notch receptor polypeptide. Notch inhibitors of the present invention comprise endogenous or exogenous small molecules, compounds, single- or double-stranded RNA polynucleotides, single- or double-stranded DNA polynucleotides, polypeptides, antibodies, intrabodies, natural or synthetic ligands, genetically-engineered ligands, and genetically-manipulated γ-secretase proteins or fragments thereof. Exemplary inhibitors of Notch activation include, but are not limited to, monoclonal antibodies to Notch ligands and receptors, RNA interference, antisense Notch, receptor and mastermind-like 1

(MAML1) decoys, beta and gamma-secretase inhibitors (GSI). Exemplary regulators of Notch activity are shown in the table below.

Regulators of Notch/LIN-12/GLP-1 Activity

| Regulator | Protein type | Direct interaction with Notch/LIN-12/GLP-1 |
|---|---|---|
| Positive regulators | | |
| DSL Ligands | Cell-surface protein | Yes |
| Su(H): LAG-1: XSu(H)1: GBF1/RBP-Jκ/KBF2 | DNA-binding protein, transcription factor | Yes |
| E(spl): ESR1: HES1: HES5 | bHLH transcription factors | No |
| Groucho | WD40 motif transcription factor | No |
| Deltex | SH3-binding domain, zinc finger, cytoplasmic protein | Yes |
| SEL-12: PS1: PS2 | Multiple-spanning transmembrane proteins | ? |
| EMB-5 | Large acidic nuclear protein | Yes |
| Negative regulators | | |
| Hairless | Acidic nuclear protein | No |
| Dishevelled | PDZ domain-containing cytoplasmic protein | Yes |
| Numb | PTB domain-containing membrane-associated protein | Yes |
| SEL-1 | Intracellular vesicle protein | ? |

The release profiles of bioactive agents and agent inhibitors is controlled by both factor diffusion and polymer degradation, the dose of the factor loaded in the system, and the composition of the polymer. Similarly, the range of action (tissue distribution) and duration of action, or spatiotemporal gradients of the released factors are regulated by these variables. The diffusion and degradation of the factors in the tissue of interest is optionally regulated by chemically modifying the factors (e.g., PEGylating growth factors).

Carrier systems for tissue regeneration are described in the table below.

Polymeric Carriers Used to Deliver Various Growth Factors and the Type of Tissues Regenerated

| Growth factor | Carrier | Tissue regenerated |
|---|---|---|
| EGF | Gelatin | Dermis |
| | PET suture | Tendon |
| | PVA sponge | Dermis |
| PDGF | Chitosan-PLLA scaffold | Craniofacial bone |
| | CMC gel | Dermis |
| | Fibrin | Ligament |
| | Porous HA | Long Bone |
| TGF-β | Alginate | Cartilage |
| | PLA | Long Bone |
| | CaP-titanium mesh | Craniofacial bone |
| | Polyoxamer; PEO gel | Dermis |
| rhBMP-2 | Collagen sponge | Long bone |
| | | Craniofacial bone |
| | HA-TCP granules | Spinal bone |
| | HA-collagen | Long bone |
| | PLA-DX-PEG | Ectopic and hip bone |
| rHBMP-7 | HA | Spinal bone |
| | Collagen-CMC | Spinal bone |
| | Porous HA | Craniofacial bone |
| bFGF | Chitosan | Dermis |
| | Heparin-alginate | Blood vessels |
| | EVAc microspheres | Blood vessels |
| | Fibrin matrices | Blood vessels |
| VEGF | PLG scaffold | Blood vessels |
| | PLG scaffold | Blood vessels |
| | PLG microspheres | Blood vessels |
| | Fibrin mesh | Blood vessels |

Abbreviations: PET, poly (ethylene terepthalate); PVA, polyvinyl alcohol; PLLA, poly (L-lactic acid); CMC, carboxymethylcellulose; HA, hydroxyapatite; PLA, poly(D,L-lactic acid); CaP, calcium phosphate; PEO, poly (ethylene oxide); TCP, tricalcium phosphate; PEG, poly(ethylene glycol); -DX-, -p-dioxanone-; EVAc, ethylene vinyl acetate; PLG, poly (lactide-co-glycolide).

The bioactive agents and agent inhibitors are added to the scaffold compositions using known methods including surface absorption, physical immobilization, e.g., using a phase change to entrap the substance in the scaffold material. For example, a growth factor is mixed with the scaffold composition while it is in an aqueous or liquid phage, and after a change in environmental conditions (e.g., pH, temperature, ion concentration), the liquid gels or solidifies thereby entrapping the bioactive substance. Alternatively, covalent coupling, e.g., using alkylating or acylating agents, is used to provide a stable, longterm presentation of a bioactive substance on the scaffold in a defined conformation. Exemplary reagents for covalent coupling of such substances are provided in the table below.

Methods to Covalently Couple Peptides/Proteins to Polymers

| Functional Group of Polymer | Coupling reagents and cross-linker | Reacting groups on proteins/peptides |
|---|---|---|
| —OH | Cyanogen bromide (CNBr) Cyanuric chloride 4-(4,6-Dimethoxy-1,3,5-triazin-2-yl)-4-methyl-morpholinium chloride (DMT-MM) | —NH$_2$ |
| —NH$_2$ | Diisocyanate compounds | —NH$_2$ |
| | Diisothoncyanate compounds | —OH |
| | Glutaraldehyde | |
| | Succinic anhydride | |
| —NH$_2$ | Nitrous Acid | —NH$_2$ |
| | Hydrazine + nitrous acid | —SH |
| | | —Ph—OH |
| —NH$_2$ | Carbodiimide compounds (e.g., EDC, DCC)[a] DMT-MM | —COOH |
| —COOH | Thionyl chloride N-hydroxysuccinimide N-hydroxysulfosuccinimide + EDC | —NH$_2$ |
| —SH | Disulfide compound | —SH |

[a]EDC: 1-ethyl-3-(3-dimethylaminopropyl) carbodiimide hydrochloride; DCC: dicyclohexylcarbodiimide Bioactive agents and agent inhibitors are capable of inducing migration of the transplanted cells and their progeny out of the polymer matrix. Other preferred bioactive substances are capable of maintaining cell viability, promoting cell proliferation or preventing premature terminal differentiation of transplanted cells. Such bioactive substances are used alone or in combination to achieve the desired result.

Bioactive substances suitable for use in the present invention include, but are not limited to: growth factors, hormones, neurotransmitters, neurotransmitter or growth factor receptors, interferons, interleukins, chemokines, cytokines, colony stimulating factors, chemotactic factors, MMP-sensitive substrate, extracellular matrix components; such as growth hormone, parathyroid hormone (PTH), bone morphogenetic protein (BMP), transforming growth factor-β (TGF-β), TGF-β1, TGF-β2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF). Splice variants of any of the above mentioned proteins, and small molecule agonists or antagonists thereof that may be used advantageously to alter the local balance of pro and anti-migration and differentiation signals are also contemplated herein.

Examples of small molecule inhibitors of angiogenesis include batimastat (BB-94) and marimastat (BB-2516), metalloproteinase inhibitors; thalidomide, a hypnosedative agent; O-(chloroacetylcarbamoyl)-fumagillol (TNP-470), a fumagillin analog; carboxyamidotriazole (CAI), a calcium channel blocker; and SU5416, a tyrosine kinase inhibitor (TKI) (Hamby and Showalter 1999, Pharmacol Ther, 82 (2-3): 169-193, incorporated herein by reference). Other suitable receptor tyrosine kinase inhibitors include 4-anilinoquinazolines and related analogs and pyrido[2,3-d]pyrimidines.

Examples of cytokines as mentioned above include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-γ (γ-IFN), IFN-γ, tumor necrosis factor (TNF), TGF-β, FLT-3 ligand, and CD40 ligand.

Suitable bioactive agents useful in accordance with the invention also include but are not limited to DNA molecules, RNA molecules, antisense nucleic acids, ribozymes, plasmids, expression vectors, marker proteins, transcription or elongation factors, cell cycle control proteins, kinases, phosphatases, DNA repair proteins, oncogenes, tumor suppressors, angiogenic proteins, anti-angiogenic proteins, cell surface receptors, accessory signaling molecules, transport proteins, enzymes, anti-bacterial agents, anti-viral agents, antigens, immunogens, apoptosis-inducing agents, anti-apoptosis agents, and cytotoxins.

Clinical Applications

The bioactive agents and agent inhibitors are useful for generation or regeneration of a number of different organs and tissue types such as musculoskeletal tissue. In the latter case, environmental cues work in concert with transcription factors to activate satellite cells, induce them to proliferate and eventually differentiate into mature muscle fibers. Numerous trophic factors play a role as initiators of satellite cell activation. Of these candidate trophic factors, both hepatocyte growth factor (HGF) and members of the fibroblast growth factor (FGF) family have been demonstrated to have a physiological role in skeletal muscle regeneration. Both types of factors initiate satellite cell activation, stimulate satellite cells to enter the cell cycle in vivo and are potent mitogens for satellite cells. In addition, the receptor for HGF, c-met, is expressed in both quiescent and activated satellite cells, and FGF-2 is present in the basement membrane surrounding developing myotubes. Both HGF and FGF2 are heparin binding proteins which depend on heparin sulfate proteoglycans (HSPG) to facilitate receptor activation. While HSPG's are ubiquitous on the surface of the cells of mammals, a specific family of HSPG's called Syndecans are involved in FGF2 signaling. In addition, Syndecan 3 and 4 are expressed on both quiescent and activated satellite cells indicating that HGF and FGF2 play important physiological roles in regulating satellite cell activation.

For cell differentiation device, cells such as stem cells are seeded into the factor-loaded polymer scaffold ex vivo and then implanted or injected into the body. Such devices are implanted at or near a target site for tissue generation or regeneration such as regenerating a tooth or a joint, e.g., an articulating joint such as a knee, elbow, shoulder, or vertebra. The zone of interaction or zone of influence in this case is in the scaffold device itself.

In a second scenario, a device that is pre-loaded with factors (e.g., morphogens, differentiation factors, and/or antagonists) but not seeded with cells (i.e., empty or cell-free) is administered to the patient. In this case, host cells of the patient enter the scaffold device after administration and differentiate in the device (in the zone of interaction or zone of influence). In each case, the device is characterized by a promoting zone and an inhibiting zone (initially), i.e., at least 2 zones. In the case of a device with multiple different factors, additional zones are present. For example, the device includes 2-5 different layers or zones. As the factors diffuse or move within the device, zones of interaction develop.

In a third scenario, the zone of influence or interaction occurs not only in the device but also outside of the device, thereby defining a sphere of influence outside of the device in surrounding tissue. An example of such a scenario is an angiogenesis-promoting device.

Clinical devices range in size from approximately microliter range volumes, e.g., 10, 25, 50 µl, to cubic millimeters to cubic centimeters (1, 2, 3, 5, 10 $cm^3$). The devices are implanted or injected directly into a site to be treated or bracketing or surrounding a treatment site.

Multi-factor polymer devices are constructed or fabricated in layers. Each device contains a plurality of factors, each of which is located in a contiguous but spatially distinct layer of the device. For example, a first layer of polymer device is made and loaded with a first active agent (e.g., morphogen), then a second layer of polymer device is made and loaded with a second active agent (e.g., second morphogen or inhibitor or antagonist thereof) and so on until the multi-layered device is completed. As described above, the process is stacked or the layers are built concentrically, e.g., starting with a first layer of polymer device loaded with a first active agent (e.g., morphogen) as the core, followed by a second layer of polymer device loaded with a second active agent (e.g., second morphogen or inhibitor or antagonist thereof) as the shell and so on adding shells until the multi-layered core-shell device is completed. Cell-seeding takes place after scaffold device fabrication (which includes factor-loading). Cells are added to the device dropwise (i.e., adding drops of a cell suspension onto a device) or by bathing the device in a cell suspension. For example, the cell suspension comprises $10^5$-$10^7$ cells/ml.

In the case of noncontiguous factor delivery, a first device is fabricated to contain a first active agent (e.g., a morphogen) and a second device is fabricated to contain a second active agent (e.g., a second morphogen or antagonist/inhibitor). The first and second devices are not physically contiguous, i.e., they are injected or implanted at different anatomical locations in the body and the zone of influence is located between them. The distance between the 2 sites is about 0.1 cm, about 0.5 cm, about 1 cm, about 2 cm, about 3 cm, about 4 cm, about 5 cm, about 6 cm, about 7 cm, about 8 cm, about 9 cm, or about 10 cm.

Angiogenesis and VEGF

Prior to the invention described herein, current approaches to therapeutically intervene in the various regenerative process have been limited by significant drawbacks, as described in detail below. Described herein are strategies leading to the creation of organized and functional networks of blood vessels that have a significant utility in the treatment of ischemic diseases and the engineering of high dimensional tissues (Richardson et al., 2001 Nat Biotechnol 19, 1029-1034; Melero-Martin et al., 2008 Circulation Research 103, 194-202; Bonauer et al., 2009 Science 324, 1710-1713; Jain, R. K. 2003 Nature Medicine 9, 685-693). Numerous molecular players are involved in different mechanisms of vascular growth (Carmeliet, P. 2000 Nat Med 6, 389-395; Folkman, J. 2006 Annu Rev Med 57, 1-18). In particular, vascular endothelial growth factor (VEGF) plays a prominent role in activating endothelial cells to form new vessels (Yancopoulos et al., 2000 Nature 407, 242-248). To date, much of the effort in therapeutic angiogenesis has been focused on the delivery of VEGF to restore blood perfusion (Takeshita et al., 1994 J Clin Invest 93, 662-670; Henry et al., 2003 Circulation 107, 1359-1365; Rajagopalan et al., 2003 Circulation 108, 1933-1938). However, formation of truly functional vasculature will likely require control over the location and magnitude of the angiogenic region, as undirected vessel growth can result in pathological effects (Dor et al., 2003 Trends in Cell Biology 13, 131-136). Moreover, improperly organized vascular networks resulting from this over-stimulation can reduce perfusion (Noguera-Troise et al., 2006 Nature 444, 1032-1037; Thurston et al., 2007 Nature Reviews Cancer 7, 327-331). This may be particularly problematic with angiogenic delivery approaches currently utilized, as systemic delivery leads to supraphysiologic concentrations, while polymeric sustained delivery systems frequently demonstrate an early burst release that leads to over-saturated local VEGF concentration in situ (Silva, E. A., and Mooney, D. J. 2007 Journal of Thrombosis and Haemostasis 5, 590-598). Importantly, while clearly documented with VEGF delivery, this issue permeates all current approaches to locally manipulate regenerative processes via exogenous factor delivery.

Described herein are results that demonstrate that clear demarcation of stimulatory zones for regeneration is achieved via appropriate co-delivery of stimulatory and inhibitory factors. Specifically, the results are presented in the context of VEGF-driven angiogenesis, using delivery of both recombinant human VEGF and an angiogenic inhibitor, anti-VEGF antibody (anti-VEGF) (Ferrara, N., and Kerbel, R. S. 2005 Nature 438, 967-974; Ferrara et al., Nat Rev Drug Discov 3, 391-400). A biodegradable polymer scaffold system is utilized to allow local and sustained release of the two factors. As described herein, the ability of this approach to spatially regulate angiogenesis was examined in a model of hindlimb ischemia (Sun et al., 2005 Pharm Res 22, 1110-1116), due to its relevance to clinical situations requiring revascularization interventions. The results from the studies presented herein demonstrate spatial control of regenerative processes by simultaneously delivering spatially segregated promoting and inhibitory agents with polymeric scaffolds. More specifically, the simultaneous, but spatially distinct, delivery of anti-VEGF and VEGF reduced the initial burst concentration of active VEGF and maintained the temporal stability of the active VEGF concentration profile. Furthermore, the spatial separation of the encapsulated pro- and anti-angiogenic agents resulted in a spatially sharp and restricted angiogenic region, leading to a heterogeneous distribution of vessels in the scaffolds and in underlying muscles.

The in vitro sprouting assay described herein confirmed that the anti-VEGF was functional and inhibited angiogenesis in a dose-dependent manner. These findings were consistent with a previously reported ND50 of four to fifteen times the mass of VEGF (Wang et al., 2004 Angiogenesis 7, 335-345; Ishihara, K. et al., 2002 International Immunopharmacology 2, 499-509; Conn et al., 1990 Proc Natl Acad Sci USA 87, 1323-1327; Cullen, V. C. 2000 General Pharmacology—the Vascular System 35, 149-157). The release profiles of VEGF and its antibody showed that the two agents were released in a sustained manner, albeit with initial bursts as observed in other studies utilizing poly (lactic-co-glycolic acid) (PLGA) (Cohen et al., 1991 Pharm Res 8, 713-720; Sheridan, et al., 2000 J Control Release 64, 91-102; Kawashima et al., 1999 J Control Release 62, 279-287; Jain, R. A. 2000 Biomaterials 21, 2475-2490).

As described in detail below, by simultaneously delivering anti-VEGF with VEGF in AVA scaffolds, the overly high concentration of VEGF that typically results from the initial burst release was mitigated. Computational simulations accounting for release, diffusion, degradation, and binding dynamics of VEGF and anti-VEGF showed that excessive VEGF was bound by anti-VEGF in this situation. The remaining free VEGF is the only active angiogenic agent delivered. Since release profiles of VEGF and anti-VEGF both exhibit initial bursts, the resulting concentration profile peak of free VEGF in the beginning was drastically reduced. Thus, the results presented herein describe that a temporally stable concentration profile of an active angiogenic agent is achieved with a delivery device that has an inherent initial burst release. This methodology is applicable to other drug delivery applications in order to mitigate the negative effects of initial bursts.

Aside from a reduction in the concentration of the free activator, VEGF, the initial spatial separation of the inhibitor and activator lead to a spatially sharp and restricted angiogenic region. This methodology mimics developmental processes in nature that use opposing factors as a method of control. Reaction-diffusion mechanisms involving an inhibitor and an activator manifest in murine interfollicular patterns, angelfish skin patterns, and avian feather size and spacing (Sick et al., 2006 Science 314, 1447-1450; Kondo, S., and Asai, R. 1995 Nature 376, 765-768; Jiang et al., 1999 Development 126, 4997-5009).

The polymer system described in the present application is also robust against fluctuations in angiogenic VEGF threshold and initial encapsulated mass. Similarly, natural processes employ mechanisms to enhance the robustness of morphogen gradients against fluctuations in gene dosage or environmental conditions (Eldar et al., 2004 Current Opinion in Genetics & Development 14, 435-439). These mechanisms include self-enhanced degradation (Eldar et al., 2003 Developmental Cell 5, 635-646), complexes with restricted diffusion (Eldar et al., 2002 Nature 419, 304-308, feedback (von Dassow et al., 2000 Nature 406, 188-192), or their combination.

Many researchers have proposed the delivery of multiple agents with different release methodologies in order to address complex biological events (Richardson et al., 2001 Nat Biotechnol 19, 1029-1034; Carmeliet et al., 2000 Nature 407, 249-257; Kisak et al., 2004 Curr Med Chem 11, 199-219; Almarza et al., 2006 Arch Oral Biol 51, 215-221; Moioli et al., 2007 Adv Drug Deliv Rev 59, 308-324; Richards Grayson et al., 2003) Nat Mater 2, 767-772; Burdick, J. A. et al., 2006 Biomaterials 27, 452-459). However, described herein is a study to achieve spatial restriction and temporal stability of an active concentration profile of a drug by simultaneously delivering a direct inhibitor.

Example 1: Effect of VEGF and Anti-VEGF on Angiogenesis

The relation between VEGF and anti-VEGF concentrations on angiogenesis was first evaluated using a common in vitro sprouting assay, in order to quantitatively determine the appropriate doses of the two factors for subsequent in vivo studies.

Cell Culture and In Vitro Sprouting Assay

Briefly, dermal human vascular endothelial cells (HMVECs) were purchased from Lonza (CC-2543) and cultured to confluence at 37° C. and 5% $CO_2$ in microvascular endothelial cell growth medium-2 (EGM-2MV) (Lonza) containing all supplements. Angiogenic activity of endothelial cells was assessed using a modification of a widely used in vitro sprouting assay (Nehls, V., and Drenckhahn, D. 1995 Microvasc Res 50, 311-322). Briefly, dextran beads microcarriers (Cytodex 3) with a dry weight of 50 mg were swollen in PBS and autoclaved. The microcarriers were washed in EGM-2MV medium and seeded with $3\times10^6$ HMVECs in a spinner flask. The microcarriers were stirred for 2 minutes out of 30 minutes for 3 hours at 37° C. incubation. After 4 hours, the beads and cells mixture were continuously stirred and incubated for an additional 20 hours. The cell-coated beads were then seeded in fibrin gel in a 24-well-plate. The composition of the fibrin gel in each well was 0.682 mg fibrinogen (Sigma, T3879), 11.4 µg aprotinin (Sigma, A4529), 0.455 U thrombin (Sigma, T6884) in 393 µL of phosphate buffered saline (PBS) and 57 µL of EGM2-MV. Gels were incubated at 37° C. for 30 minutes and media of experimental conditions were placed on top of the gel. Experimental media were prepared by adding appropriate concentrations of VEGF and anti-VEGF to EGM-2MV without the growth factor supplements, but with the addition of 10 ng/mL hepatocyte growth factor (HGF) for all conditions. Media were changed every 24 hours and the cells were allowed to sprout from beads into surrounding gel over 4 days. After 4 days, the gels were rinsed with PBS and fixed with 4% paraformaldehyde prior to imaging. Subsequent to fixing, samples were stained with 4',6-diamidino-2-phenylindole (DAPI) and visualized at 10× objective magnification with an Olympus IX2 microscope. Sprouts were identified as continuous multi-cellular structures extended from the microcarrier beads with a minimum of two cells in the structure.

Figure 1A:
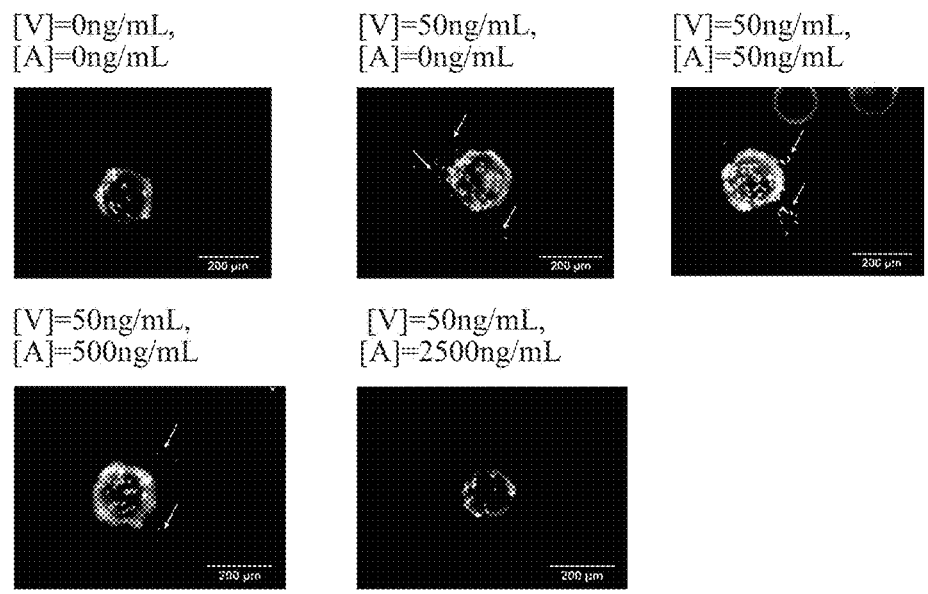
FIG. 1a shows representative images of cell-seeded dextran beads embedded in fibrin gel under different media conditions. Cells were stained with DAPI. A sprout was defined as a multi-cellular extension with >1 connected ECs that were attached to the micro-carrier (see arrows).
Figure 1B:
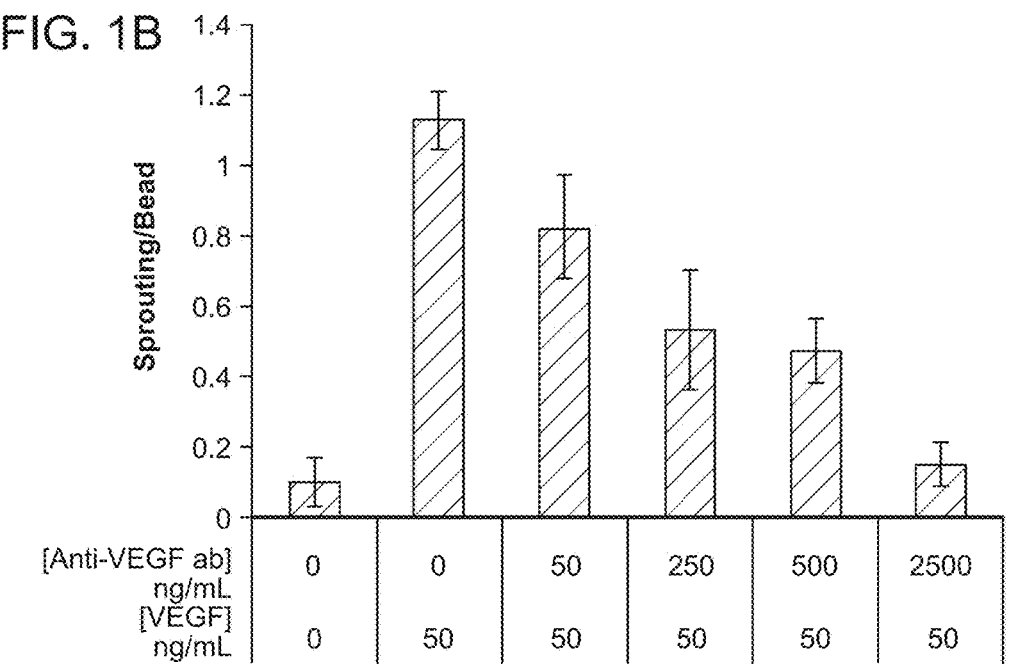
FIG. 1b shows the results of quantification of the number of sprouts per bead at different conditions. Values represent means and error bars represent standard deviations (n=4).

VEGF induced angiogenic sprouting, an analog to the initial stage of angiogenesis, whereas anti-VEGF reduced the angiogenic effects of VEGF (FIG. 1), as expected. The dose-dependent effects of anti-VEGF at a constant VEGF of 50 ng/mL were analyzed, and an anti-VEGF concentration 50-fold greater than that of VEGF effectively eliminated the angiogenic effects of VEGF (FIG. 1b).

Scaffold Fabrication and Quantification of Protein Release Kinetics

To allow local and sustained delivery of VEGF and anti-VEGF, the proteins were incorporated into poly(lactide-co-glycolide) scaffolds that have been commonly utilized in the past for delivery of single stimulatory factors (Sun et al., 2005 Pharm Res 22, 1110-1116; Peters et al., 2002 J Biomed Mater Res 60, 668-678; Chen, R. R., and Mooney, D. J. 2003 Pharm Res 20, 1103-1112). However, in this situation, three-layer PLG scaffolds were fabricated, and the different proteins were localized into the distinct layers.

An exemplary scaffold device is produced as follows. A 85:15, 120 kD copolymer of D,L-lactide and glycolide (PLG) (Alkermes, Cambridge, Mass.) was used in a gas-foaming process to form macroporous PLG matrix scaffolds (Harris et al., 1998 Journal of Biomedical Materials Research 42, 396-402). All scaffolds were cylinders 4.2 mm in diameter and 3 mm in thickness. PLG microspheres (diameter=5-100 µm), prepared by standard double emulsion (Cohen et al., Pharm Res 8, 713-720), were mixed with lyophilized proteins, sodium chloride, and 5% alginate by mass. The mixture was compressed into discs and equilibrated with high-pressure carbon dioxide. When the pressure was released, PLG particles expanded into spaces between salt particles and fused, entrapping the lyophilized proteins and salt. Salt particles were removed by leaching with a 100 mM $CaCl_2$ solution to generate porous scaffolds. The VEGF-A isoform VEGF (165) (Biological Resources Branch of the National Cancer Institute, Bethesda, Md., USA) was used throughout these studies. Four types of scaffolds were fabricated: i) blank scaffolds without protein incorporation (B), ii) scaffolds with 4 µg of VEGF (V), iii) 3-layered scaffolds with a 1 mm central layer containing 4 µg of VEGF and two surrounding 1-mm layers without protein incorporation (BVB for Blank-VEGF-Blank), and iv) 3-layered scaffolds with a 1 mm central layer containing 4 µg of VEGF and two surrounding 1-mm layers each incorporating 20 µg of anti-VEGF (R&D Systems AB-293-NA).

The release kinetics of anti-VEGF antibody (anti-VEGF) and VEGF from each layer of the scaffold were determined using 0.11 µCi $^{125}$I-labeled anti-mouse IgG (Perkin Elmer, DEX159100UC) and 0.11 µCi $^{125}$I-labeled human VEGF (Perkin Elmer, NEX328005UC), respectively, as tracers. The tracers were entrapped in scaffolds using an identical process with the remaining bulk quantities consisting of unlabeled anti-VEGF and unlabeled VEGF, respectively. The total radioactivity of each scaffold layer (n=5) was measured with a WIZARD Automatic Gamma Counter (Perkin Elmer) prior to incubation at 37° C. in 2 mL of PBS. At specific measurement time points, release solutions were measured using the Gamma counter and the scaffolds were placed in fresh release solutions. The cumulative protein release from the scaffolds at each time point was normalized as a percentage of total protein incorporated.

Figure 2:
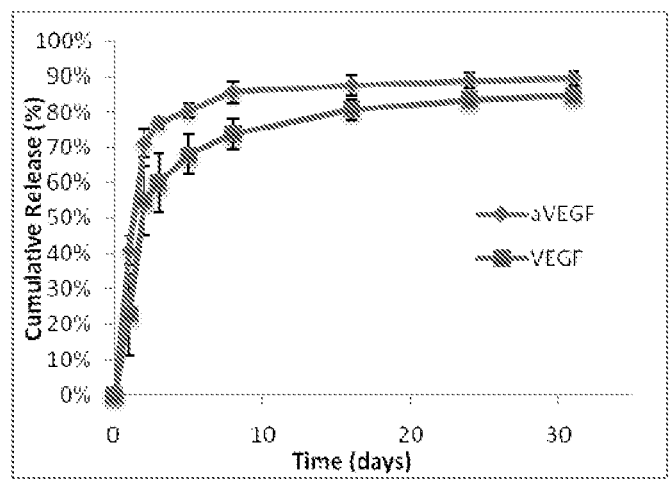
FIG. 2 is a line graph demonstrating the in vitro cumulative release kinetics of anti-VEGF antibody and VEGF from scaffolds. Initial mass of proteins incorporated were 4 µg of VEGF and 20 µg of anti-VEGF. Values represent mean and error bars represent standard deviations (n=5).

Protein which was incorporated into each layer of the scaffold remained confined to that layer, as demonstrated previously (Chen et al., 2007 Pharm Res 24, 258-264). Radiolabeled tracers were used to model the release of the two proteins from the scaffolds and there was a sustained release of the proteins over several weeks (FIG. 2). Approximately 60% and 75%, respectively, of VEGF and anti-VEGF were released in the first 3 days. Notice that the initial burst release for anti-VEGF was greater than that of VEGF. Over the next 11 days, the release rates varied between 0.5% to 3% per day, and from day 14 to 31, only 1-2% of the proteins were released.

Example 2: Mathematical Model of Protein Distribution

In order to design appropriate encapsulated doses of VEGF and anti-VEGF to create spatially defined angiogenic regions, mass transport PDEs of the proteins in the scaffolds and the underlying tissues were simulated.

Briefly, a computational model was generated to depict the concentration profiles of free VEGF anti-VEGF, and VEGF complexed with anti-VEGF. This model accounted for diffusion, release from scaffolds, binding kinetics, and protein degradation. The governing equations of the VEGF and anti-VEGF concentrations inside the scaffold and underlying muscle were:

$$\frac{\partial c_1}{\partial t} = D_1 \nabla^2 c_1 - k_1 c_1 + f_1 - k_{on} c_1 c_2 + k_{off} c_3$$

$$\frac{\partial c_2}{\partial t} = D_2 \nabla^2 c_2 - k_2 c_2 + f_2 - k_{on} c_1 c_2 + k_{off} c_3$$

$$\frac{\partial c_3}{\partial t} = D_3 \nabla^2 c_3 + k_{on} c_1 c_2 - k_{off} c_3$$

where $c_i$ = concentration $c_i(x, y, z, t = 0) = 0; \forall\, i, x, y, z$ $$f_i = \begin{cases} \text{release function, inside scaffold} \\ 0, \quad \text{inside muscle} \end{cases}$$

$$i = \begin{cases} 1 \quad \text{free } VEGF \\ 2 \quad \text{free } antiVEGF \\ 3 \quad VEGF\text{-}antiVEGF \text{ complex} \end{cases}$$

$D_1 = 7 \times \frac{10^{-7} \text{ cm}^2}{s} = $ Effective interstitial diffusion coefficient of $VEGF_{165}$ $D_2 = 3.2 \times \frac{10^{-9} \text{ cm}^2}{s} = $ Effective interstitial diffusion coefficient of $IgG\ Ab$ $D_3 = 2.9 \times \frac{10^{-9} \text{ cm}^2}{s} = $ Effective interstitial diffusion coefficient of complex $k_1 = 2.31 \times 10^{-4} s^{-1} = $ Degradation rate of $VEGF$ $k_2 = k_3 = 1.34 \times 10^{-6} s^{-1} = $ Degradation rate of free anti-$VEGF$ and $VEGF$-anti-$VEGF$ complex $k_{on} = 5.5 \times 10^4 M^{-1} s^{-1}$ (36)

$k_{off} = 11 \times 10^{-4} s^{-1}$ (36)

See, Chen et al., 2007 Pharm Res 24, 258-264; Helm et al., 2005 Proceedings of the National Academy of Sciences of the United States of America 102, 15779-15784; Brouwers et al., 2006 J Biomech 39, 2774-2782; Clauss, M. A., and Jain, R. K. 1990 Cancer Res 50, 3487-3492; Pluen 2001 Proceedings of the National Academy of Sciences of the United States of America 98, 4628-4633; Crank, J. 1975 *The mathematics of diffusion*, 2d ed., Clarendon Press, Oxford, Eng; Vieira, P., and Rajewsky, K. 1988 Eur J Immunol 18, 313-316; Vieira, P., and Rajewsky, K. 1986 Eur J Immunol 16, 871-874; and Bakri, et al., 2007 Ophthalmology 114, 855-859.

In the model, the VEGF-anti-VEGF-body complex is assumed to have no degradation. VEGF and anti-VEGF are modeled to only degrade when not bound together. This should have a negligent impact on the overall dynamics of the system due to the small magnitude of degradation rates compared to $k_{off}$. The release function inside each layer of the scaffolds was determined by the initially incorporated amount of protein multiplied by the instantaneous release curve, which was a piecewise cubic interpolation from the empirically measured radio-labeled protein release kinetics. Effective diffusion coefficients and degradation rates were assumed to be time-invariant and spatially uniform. Since the effective diffusion coefficients were experimentally measured, they were assumed to incorporate binding kinetics to the extracellular matrix (ECM) proteins as well as uptake by cells. The system geometry, equation system, and initial conditions were constructed in COMSOL Multiphysics using the 3D coefficient form PDE model. The time dependent system was solved with the GMRES linear system solver and the output was exported and analyzed in Matlab.

Figure 3A:
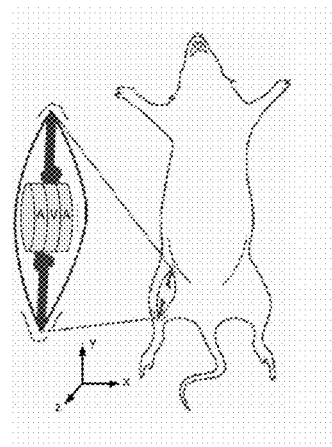
FIG. 3a shows orientation of implanted scaffold in a mouse that underwent ischemic hindlimb surgery. The axes definitions are such that x is perpendicular to the severed femoral artery and vein, y is parallel to the femoral artery and vein, and positive z points away from the underlying muscle. Note that the x-y plane lies tangential to the interface between the scaffold and the underlying muscle, and that the coordinate (0,0,2.1 mm) is located at the center of the scaffold.
Figure 3B:
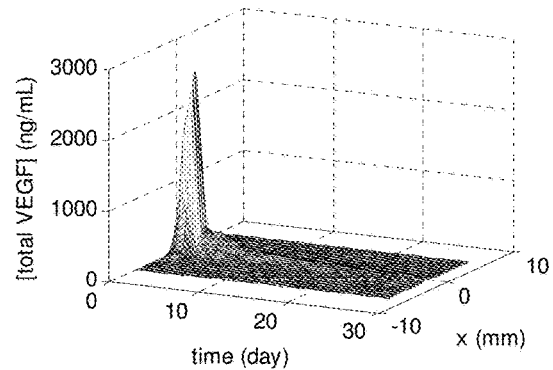
Figure 3C:
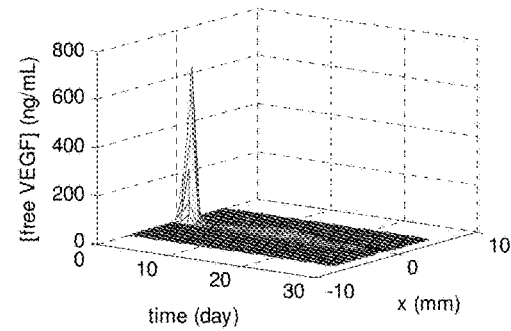
Figure 3D:
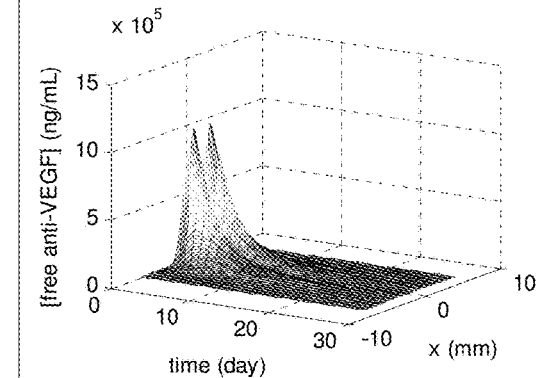
Figure 3E:
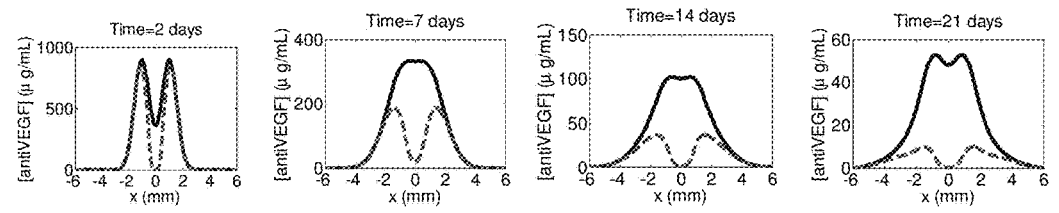
FIG. 3e shows cross-sectional plots of concentration profiles of total anti-VEGF (blue solid) and free anti-VEGF (green dashed) at 3, 7, 14, and 21 days.
Figure 3F:
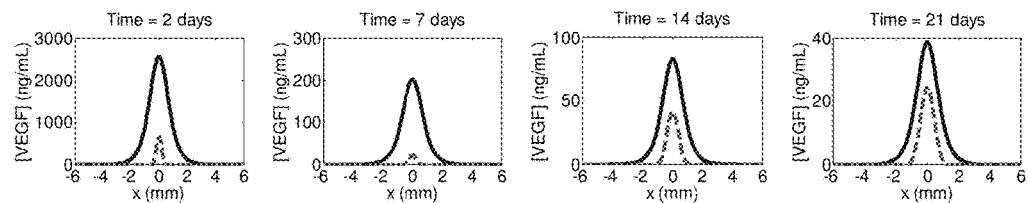
FIG. 3f illustrates cross-sectional plots of concentration profiles of total VEGF (blue solid) and free VEGF (green dashed) at 3, 7, 14, and 21 days.
Figure 3G:
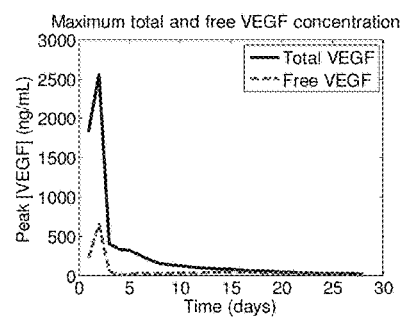
Figure 3H:
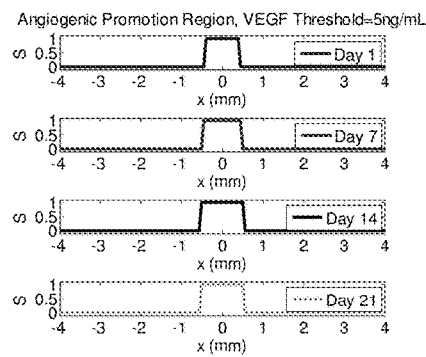
FIG. 3h shows angiogenic promotion region (APR) at 1, 7, and 14 days, where the angiogenic promotion signal is defined as $$S(x, y, z) = \begin{cases} 1 & \text{for } [VEGF_f] > 5 \text{ ng/mL} \\ 0 & \text{for } [VEGF_f] \leq 5 \text{ ng/mL}. \end{cases}$$
Figure 3I:
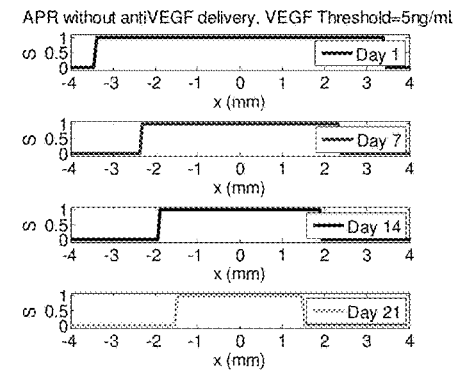
FIG. 3i shows angiogenic promotion region without the delivery of anti-VEGF.
Figure 8:
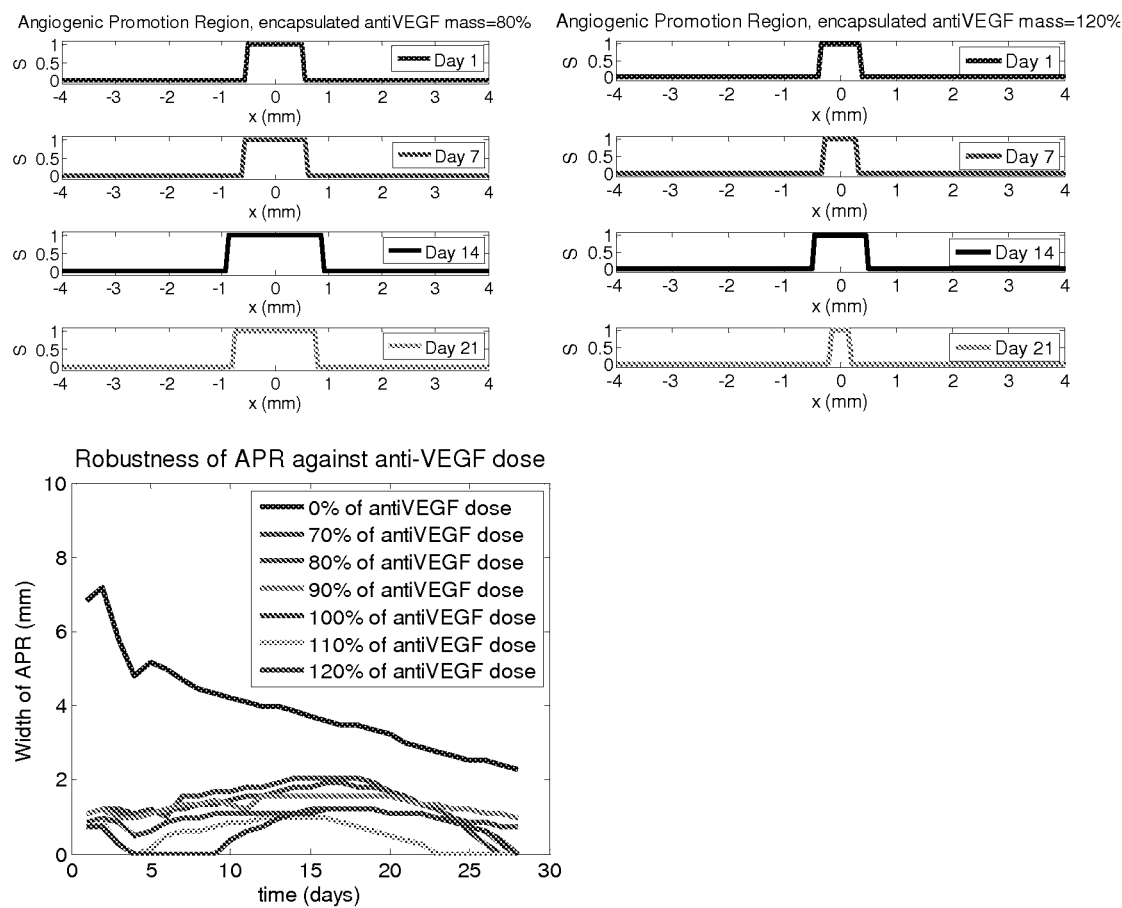
FIG. 8 is a series of line graphs showing the robustness of angiogenic promotion signal against initial anti-VEGF dosage. APR is shown at 1, 7, 14, and 21 days and the widths of the APR are plotted over time.
Figure 9:
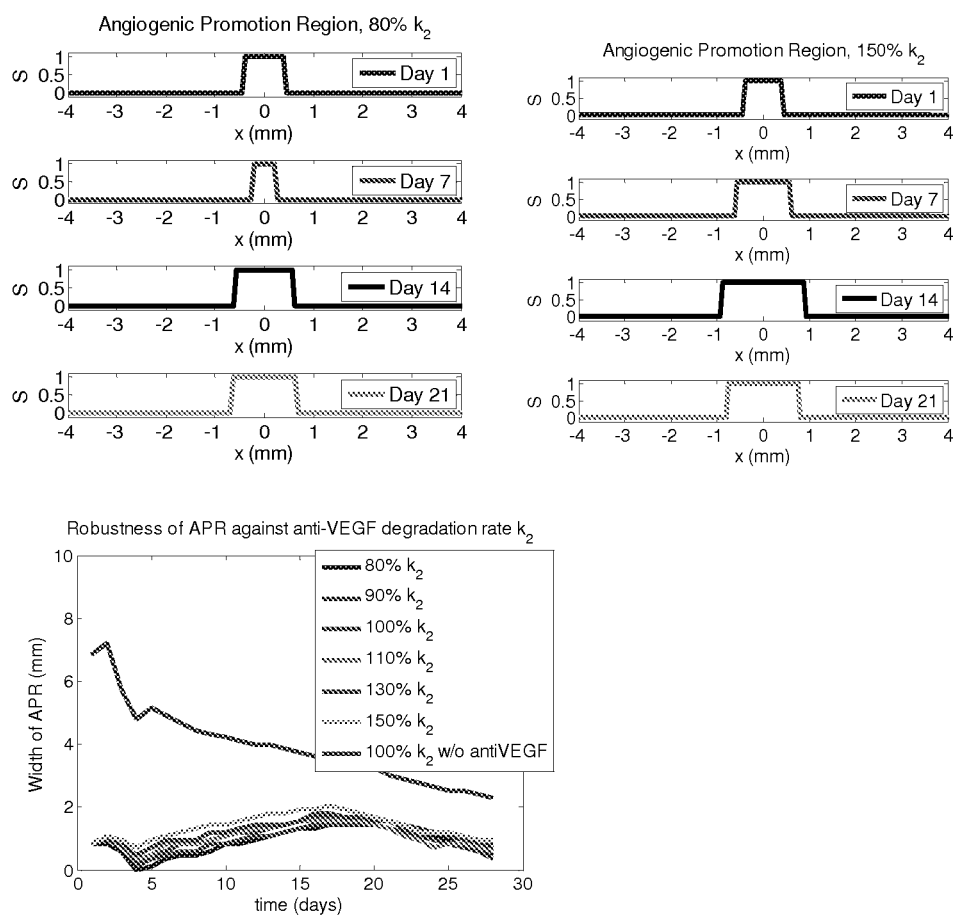
FIG. 9 is a series of line graphs demonstrating the robustness of angiogenic promotion signal against degradation rate of anti-VEGF. APR is shown at 1, 7, 14, and 21 days and the widths of the APR are plotted over time.

Parameters for the models were obtained from empirical release kinetics and diffusion and degradation coefficients from literature. For example, by setting an initial amount of 4 μg VEGF in the central layer of the scaffold and 20 μg anti-VEGF in each of the surrounding layers (FIG. 3a), the concentration profiles of total VEGF free VEGF (not bound to anti-VEGF), and free anti-VEGF over time at a tissue cross section 0.5 mm into the underlying muscle were simulated (FIGS. 3b-d). These simulations showed a sharp peak for the total VEGF concentration (free VEGF+VEGF bound to antibody) centered at the central layer and two anti-VEGF peaks on the two sides. However, the diffusion of anti-VEGF into the central layer caused most of the total VEGF to become antibody bound in the central layer, creating significantly reduced peaks of free VEGF compared to total VEGF (FIG. 3e). Strikingly, the binding of free VEGF by antibody had a dramatic smoothing effect on the concentration of free VEGF as a function of time. By contrast, the total VEGF concentration started extremely high and then rapidly dropped, due to the changing release rate over time and its simultaneous degradation. These effects were largely dose-independent (FIGS. 8-9), although the absolute value of the quasi-steady-state free VEGF concentration was strongly influenced by the VEGF and anti-VEGF doses. From previous in vitro VEGF dosage studies of endothelial sprouting (Chen et al., 2007 FASEB J 21, 3896-3903) and in vivo measurement of tissue VEGF concentrations (Silva, E. A., and Mooney, D. J. 2007 Journal of Thrombosis and Haemostasis 5, 590-598), the minimum effective VEGF concentration in vivo to induce angiogenesis is ~5 ng/mL. Utilization of the 4 μg doses led to free VEGF concentrations that were still above this threshold for a 4 week timeframe. As a comparison of the profile stability, the standard deviations of the daily peak for total VEGF and free VEGF over 28 days were computed: 558 ng/mL for total VEGF and 132 ng/mL for free VEGF. Most of the fluctuations came from the spike in concentrations on day 2 (FIG. 3g). The concentration peak of active VEGF on day 2 was reduced by 72% by the binding activity of anti-VEGF.

To determine the spatial control over angiogenesis with this approach, the level of angiogenic promotion was expressed as a binary event, defined as angiogenic promotion $$\text{signal } (S),\ S(x, y, z) = \begin{cases} 1 \text{ for } [VEGF_f] > 5 \text{ ng/mL} \\ 0 \text{ for } [VEGF_f] \leq 5 \text{ ng/mL} \end{cases}$$

Figure 7:
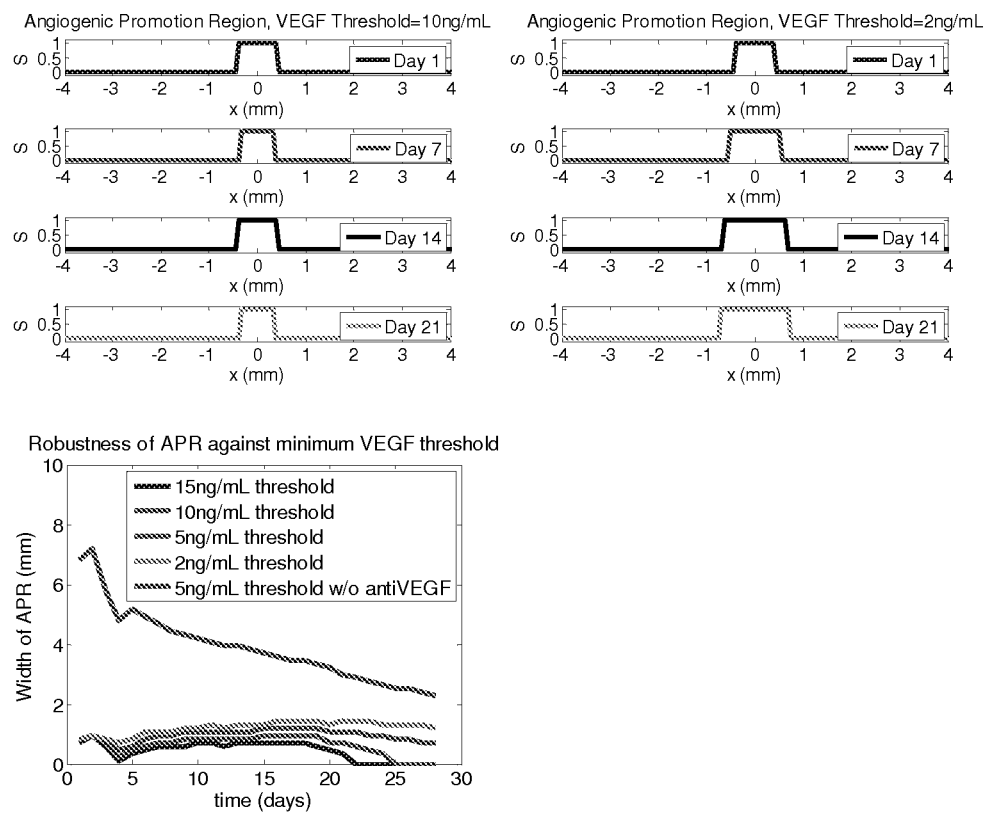
FIG. 7 is a series of line graphs illustrating the robustness of angiogenic promotion signal against minimum free VEGF threshold for angiogenic promotion. APR is shown at 1, 7, 14, and 21 days and the widths of the APR are plotted over time.

S(x,y,z)=1 indicated that angiogenesis was promoted at said coordinate and local S=0 indicated that angiogenesis was inhibited. Plots of S vs. x (FIG. 3f) demonstrated that angiogenic promotion was restricted with this system in the approximate 1 mm central region, which was defined as the angiogenesis-promoting region (APR). This spatial restriction was maintained for 3 weeks, demonstrating a highly stable environment, although the APR first broadened then contracted slowly. In the first 19 days, the APR width expanded gradually from 0.84 mm to 1.2 mm, although there is a brief drop to 0.48 mm on day 4. From day 20 to day 28, the APR contracted from 1.2 mm to 0.72 mm. In this computational model, 5 ng/mL was chosen as the minimum threshold for angiogenic promotion, consistent with other groups (Wang et al., 2004 Angiogenesis 7, 335-345; Ozawa et al., 2004 J Clin Invest 113, 516-527). The choice of this parameter did not affect the temporal stability of the free-VEGF concentration profiles, though the width of the APR deviated by ±25% with the minimum threshold ranging from 2 ng/mL to 10 ng/mL (FIG. 7). Thus, both temporal stability and spatial restriction of active VEGF were robust to the minimum biologically active threshold. The results of this modeling suggest that highly stable, in terms of both time and space, regions of pro-angiogenic activity could be readily created by appropriate dosing of VEGF and anti-VEGF. The maintenance of the APR is also robust against changes in the amount of anti-VEGF and VEGF encapsulated initially. When the initial encapsulated mass of anti-VEGF was varied from 80% to 110% of the base level, the width of the APR deviates for less than 25% (FIG. 7b). Similarly, the width of the APR deviated for less than 25% when the degradation rate of anti-VEGF was varied from 80% to 130% (FIG. 7c).

Example 3: Spatially Regulated Angiogenesis In Vivo

To test the ability of this system to provide spatial control over angiogenesis, scaffolds were subsequently implanted into the ischemic hindlimbs of SCID mice.

Mouse Model of Hindlimb Ischemia

Scaffolds were implanted in 6-week-old SCID mice (Taconic, Hudson, N.Y.) that had undergone unilateral ligation of hindlimb blood vessels to create a severe model of hindlimb ischemia (Sun et al., 2005 Pharm Res 22, 1110-1116). The SCID model was chosen because it offered a stable loss of perfusion over weeks and the angiogenic effects from inflammation were reduced. Briefly, animals were anesthetized by IP injection of a 7:1 mixture of ketamine and xylazine. The targeted hindlimb was shaved and sterilized with ethanol prior to making an incision through the dermis. Ligation sites were made on the external iliac artery and vein, and on the femoral artery and vein using 5-0 Ethilon (Ethicon, Somerville, N.J.). The vessels were severed between the ligation sites. A scaffold was implanted such that its rotational axis was perpendicular to the direction of the severed vessels, with the round edge sitting on top of the muscle. This orientation effectively made each layer parallel to the original femoral artery and vein.

Analysis of Vascularization

Scaffolds and the surrounding muscles from the ischemic hindlimbs were retrieved after 4 weeks, fixed in Z-fix (Anatech, Battle Creek, Mich.) overnight and changed into 70% ethanol (EtOH) for storage prior to histologic processing. Samples were embedded in paraffin and sectioned onto slides. Sections were immunostained with a monoclonal antibody raised against mouse CD31 (diluted 1:250) (Pharmingen, San Diego, Calif.) with the Tyramide Signal Amplification (TSA) Biotin System (Perkin Elmer Life Sciences, Boston, Mass.). Briefly, deparaffinized sections were rehydrated, blocked for endogenous peroxidase activity and non-specific interactions, and incubated overnight at 4° C. with the primary CD31 antibody. Sections were then incubated with a biotinylated anti-rat IgG (Vector Laboratories, Burlingame, Calif.), followed by application of a tertiary TSA strepavidin antibody and a TSA biotinyl tyramide amplification. This was followed by reapplication of the tertiary antibody. The samples were stained using DAB+ substrate chromogen (DAKO, Carpinteria, Calif.) and counterstained with hematoxylin.

Sections from each sample were visualized at 10× and 20× objective magnifications with a Nikon light microscope (Indianapolis, Ind.) connected to a SPOT digital image capture system (Diagnostic Instruments, Sterling Heights, Mich.). Images were taken of entire sections at 10× objective magnification and merged into a complete image of the section using Photoshop Elements (Adobe Systems, San Jose, Calif.). Blood vessel densities (BVD), marked by CD31, were manually determined in the entire scaffold and underlying muscle tissues as previously described (Richardson et al., 2001 Nat Biotechnol 19, 1029-1034; Sun et al., 2005 Pharm Res 22, 1110-1116).

Measurements of the blood perfusion in the ischemic and normal limb of the anesthetized animals (n=5) were performed using Laser Doppler Perfusion Imaging (LDPI; Perimed, AB, Stockholm, Sweden). To minimize variability due to ambient light, temperature, and individual heart rate, perfusion in the ischemic hindlimb was normalized by the perfusion in the normal hindlimb of the same animal.

Figure 4A:
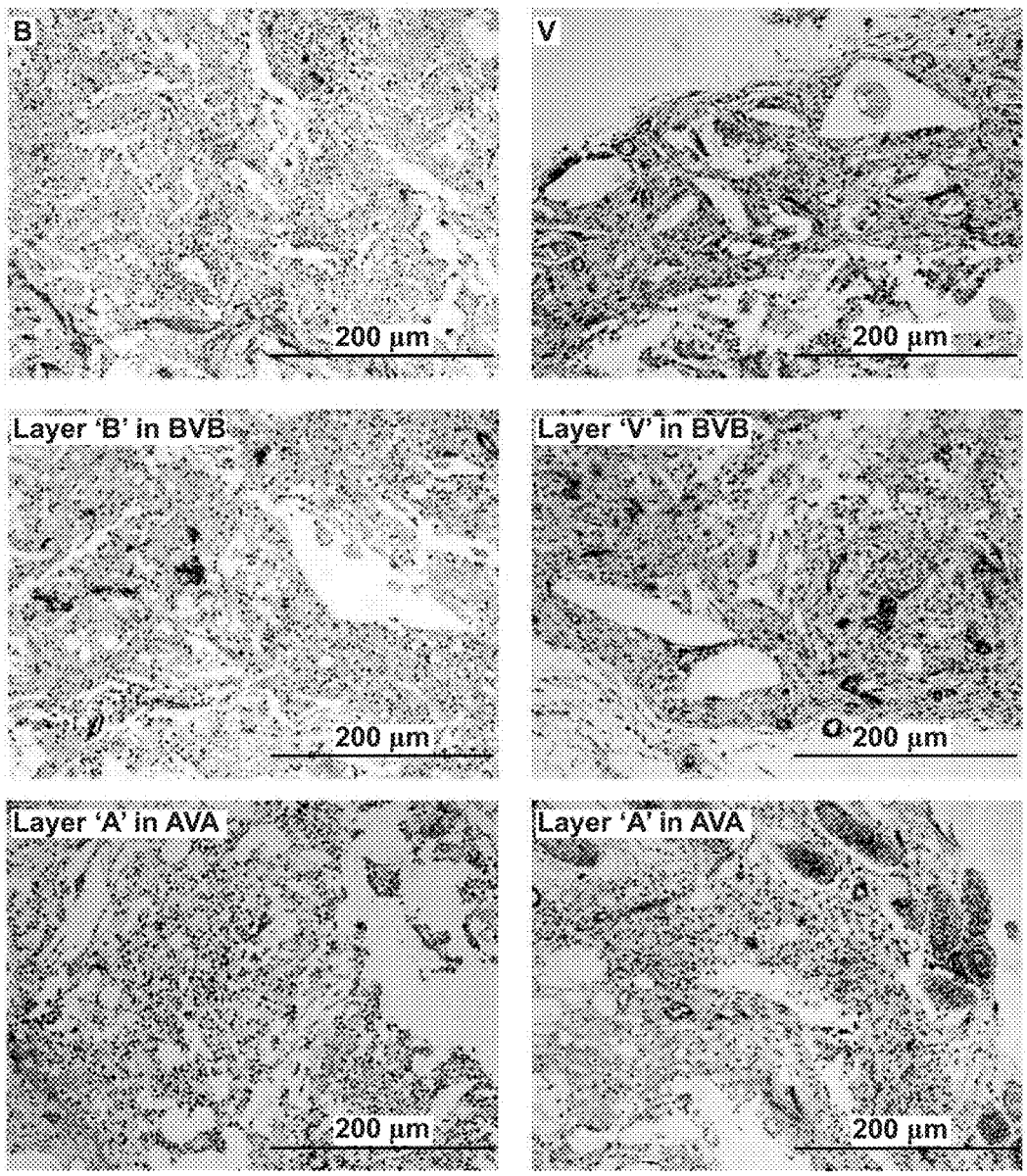
FIG. 4a shows representative images of CD31 stained sections of various types of scaffolds implanted in ischemic hindlimbs. 'B only'=blank scaffolds; 'V only'=scaffolds delivering only VEGF. 'BVB'=tri-layered scaffolds with a VEGF-containing layer sandwiched by two blank layers; 'AVA'=tri-layered scaffolds with a VEGF-containing layer sandwiched by two anti-VEGF-containing layers. Scale bar represents 200 µm.
Figure 5A:
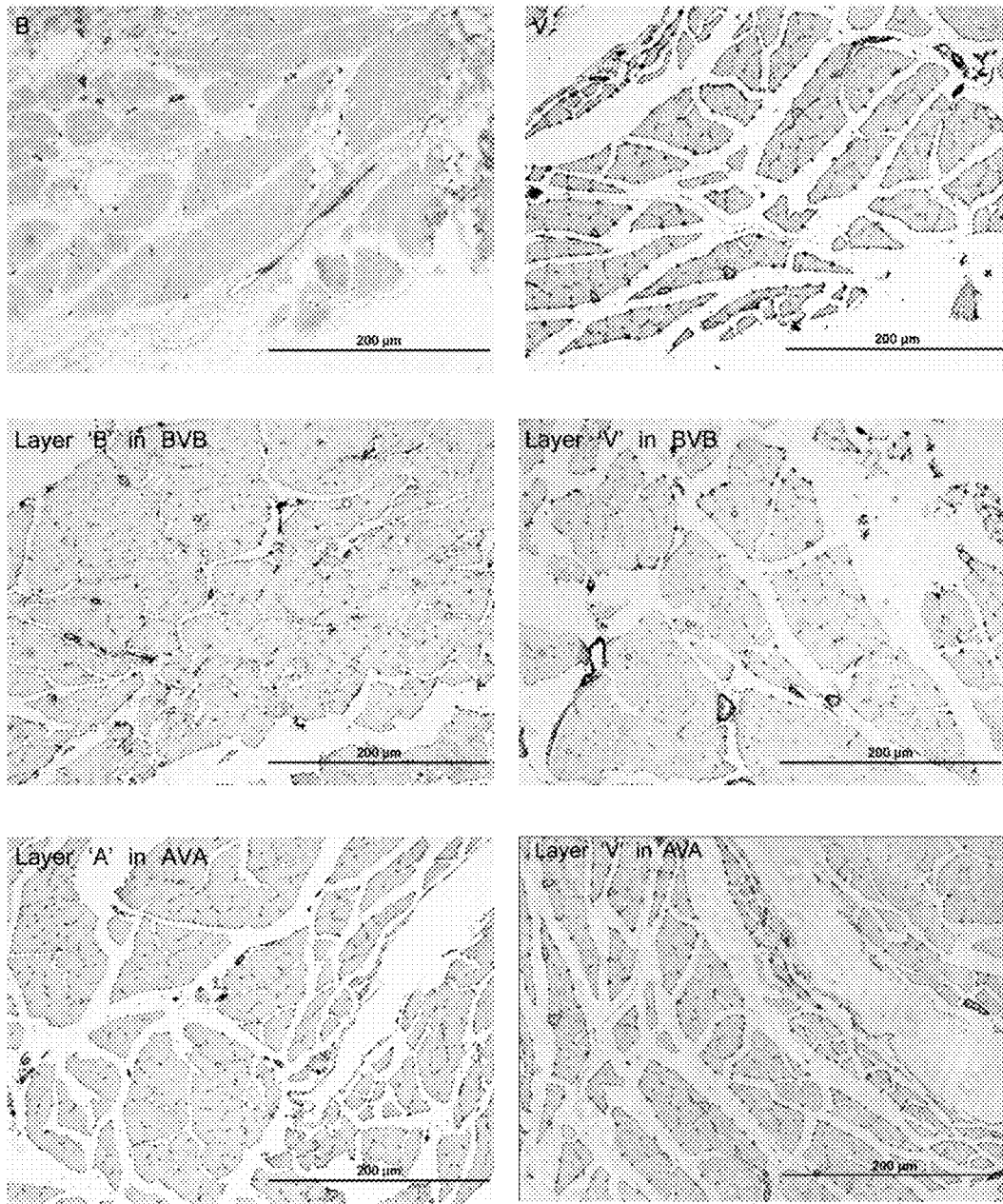
FIG. 5a demonstrates representative images of CD31 stained muscle sections directly underneath the layers of various types of implanted scaffolds. Scale bar represents 200 µm.
Figure 5B:
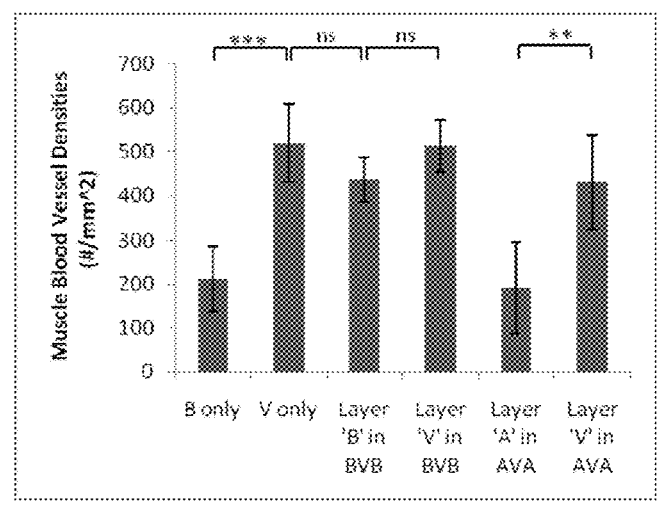
FIG. 5b shows the quantification of vessel densities within the underlying muscles (*p≤0.05, p≤0.01, *p≤0.001). Values represent mean and error bars represent standard deviations (n=5).
Figure 6:
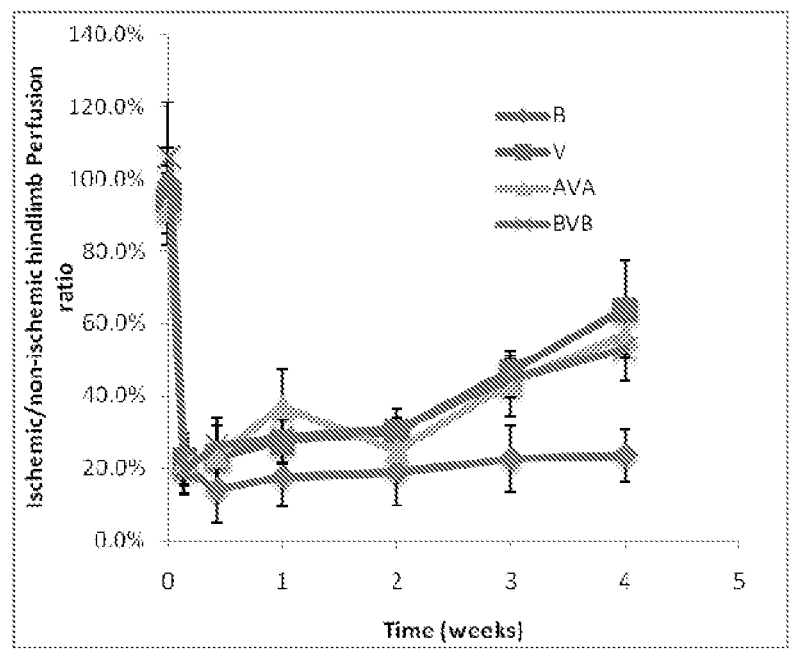
FIG. 6 is a line graph demonstrating the quantitative analyses of hindlimb perfusion using laser Doppler perfusion image (LDPI) in mice (n=5). Blood flow was expressed as ischemic limb/untreated limb perfusion in mice. 'B'=blank scaffolds; 'V'=scaffolds delivering only VEGF. 'BVB'=tri-layered scaffolds with a VEGF-containing layer sandwiched by two blank layers; 'AVA'=tri-layered scaffolds. Implantations of scaffolds containing VEGF (V, AVA, BVB) all resulted in enhanced perfusion in the ischemic limb compared to the implantation of blank scaffolds (B).

Both the new vasculature that formed within the infiltrated scaffold and the vasculature in the muscle underneath the scaffold were analyzed, four types of scaffolds were examined: 1) blank scaffolds containing no proteins (B), 2) scaffolds containing 4 µg of VEGF in total distributed homogenously (V), 3) three-layered scaffolds with 4 µg VEGF contained in the central layer and 20 µg anti-VEGF contained in each of the side layers (AVA), and 4) three-layered scaffolds with 4 µg VEGF in the central layer and side layers containing no proteins (BVB). The aforementioned computational model suggested that implanted AVA scaffolds would result in a distinct region that promoted angiogenesis and that this region would be maintained in the first two weeks. This spatially restricted signal was expected to lead to spatially heterogeneous blood vessel densities. At the experimental end point (4 weeks), mice were sacrificed and blood vessel densities of the cell-infiltrated scaffolds and underlying muscles were quantified. Delivery of VEGF in all scaffold types (V, BVB, and AVA) resulted in an approximate twofold increase in blood vessel density in the scaffolds (FIGS. 4a and b). Furthermore, layers 'B' in BVB showed a similar level of increase (FIG. 4b), indicating that the region of angiogenesis-promotion was not restricted to the central layer. In contrast, layers 'A' in the AVA scaffolds showed a reduction of blood vessel density, to a similar value as the blank condition (FIG. 4b). Similarly, analysis of the underlying muscle showed that increased blood vessel densities were generated in the muscles underneath a polymer initially encapsulated VEGF, and AVA scaffolds effectively restricted this increase to the muscle directly underneath the central layer (FIG. 5). Finally, laser Doppler perfusion imaging (LDPI) was performed in order to assess the effects on functional perfusion by local restriction of angiogenesis (FIG. 6). In all groups, perfusion decreased immediately subsequent to induction of ischemia. However, implantation of all three types of scaffolds containing VEGF led to significant recovery of perfusion, well above the control (no VEGF delivery), and spatially restricting angiogenesis did not compromise the ability of VEGF delivery to improve regional perfusion.

The capillary densities achieved in VEGF-containing layers were comparable to previous studies with protracted release of VEGF (Sun et al., 2005 Pharm Res 22, 1110-1116; Chen Pharm Res 24, 258-264). Despite the reduction in total active VEGF delivered in the AVA scaffolds, the resulting vessel densities and perfusion in the scaffold and in the underlying muscles were not statistically different than those of the scaffolds delivering VEGF only. The free VEGF concentration in the V and BVB scaffolds likely is an over-saturating dose, or the excessive VEGF created non-productive vasculature in these conditions (Noguera-Troise et al., 2006 Nature 444, 1032-1037; Thurston et al., 2007 Nature Reviews Cancer 7, 327-331; Ridgway et al., 2006 Nature 444, 1083-1087). Another possibility is that the lowered microenvironmental VEGF concentration in the AVA condition resulted in more structurally effective blood vessels in the central layer that compensated for the reduced blood vessel densities in the two side layers.

Example 4: Multi-Modal Scaffold Design to Create Spatiotemporal Morphogens Fields for Precision Tissue Engineering The methods and compositions are also useful to release distinct factors from various compartments (with a complementary inhibitory factor released from another compartment) to promote stem cell differentiation down different pathways in distinct spatial locations. These methods mimic naturally-occurring tissue development such as embryonic development.

Embryonic development involves a concerted, precise interplay of morphogens and inhibitors that provide spatial and temporal cues to drive tissue differentiation and organismal patterning. A major premise of such development is that all the cells within the given developmental field are homogenous and pluripotent in terms of their lineage and are capable of being programmed into multiple distinct lineages that represents stable, functional tissue fates.

Control release methodology utilizes polymer based systems that are capable of precisely controlling temporal kinetics and spatial regulation of biomolecules ranging from peptides, proteins, nucleic acids and small molecules. One can spatially segregate a single induction signal, or even multiple factors by placing them in distinct compartments in a delivery system (Chen R R, Silva E A, Yuen W W, Mooney D J. Spatio-temporal VEGF and PDGF delivery patterns blood vessel formation and maturation. Pharmaceutical Research. 2007 February; 24(2):258-64). Spatially segregating the release of an inductive and an inhibitory molecule (VEGF and an a neutralizing antibody to VEGF) can lead to sharp boundaries defining the region in which a process is promoted (Yuen W W, Du N R, Chan C H, Silva E A, Mooney D J. Mimicking nature by codelivery of stimulant and inhibitor to create temporally stable and spatially restricted angiogenic zones. Proc Natl Acad Sci USA. 2010 Oct. 19; 107(42):17933-8).

Improvements over existing systems described herein include: (1) use of macroporous polymer systems that mediate spatial reorganization and morpho-differentiation; (2) use of multiple morphogens and inhibitory molecules to precisely define induction fields; and (3) use of latent complexes that allow precise temporal onset of actions by photoactivation.

Spatially Distinct Morphogens Fields (Multilayered Design)

Using the PLGA microsphere system release of morphogens cues was demonstrated. For example, two growth factors, TGFB-β1 and BMP4, are in two layered zones while their neutralizing antibodies are released from opposite compartments a well as within the middle neutral zone to restrict their field of action.

Figure 10:
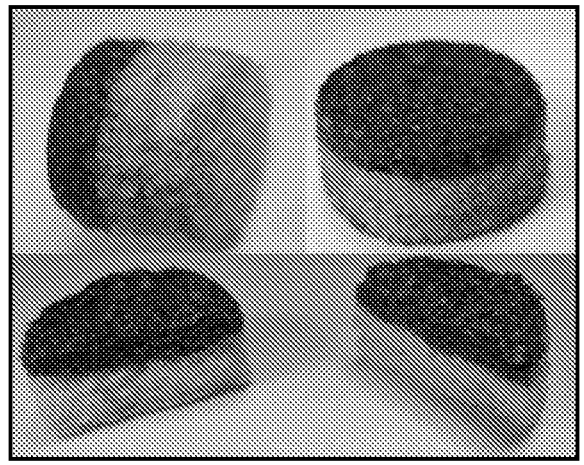
FIG. 10 is a series of photographs depicting various views of dual dye-incorporated layered polylactic acid and polyglycolic acid (PLGA) scaffolds demonstrating the distinct spatial compartments.
Figure 11:
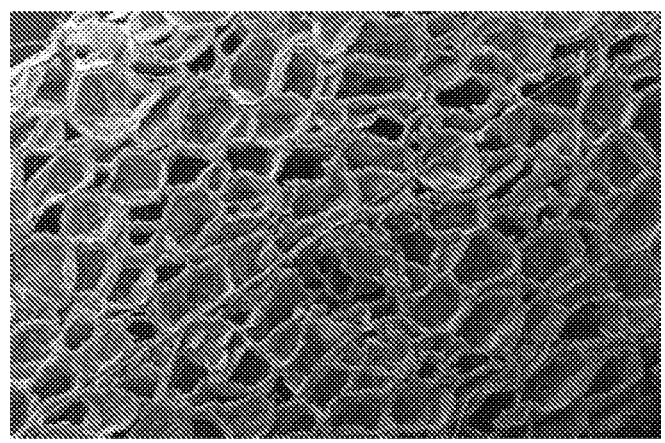
FIG. 11 is a scanning electron micrograph (SEM) image of a layered PLGA scaffold demonstrating the macroporous architecture.
Figure 12:
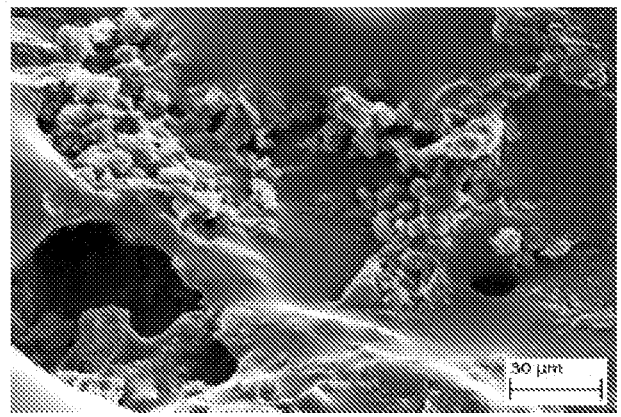
FIG. 12 is an SEM image demonstrating cell seeding in a PGA scaffold.
Figure 13:
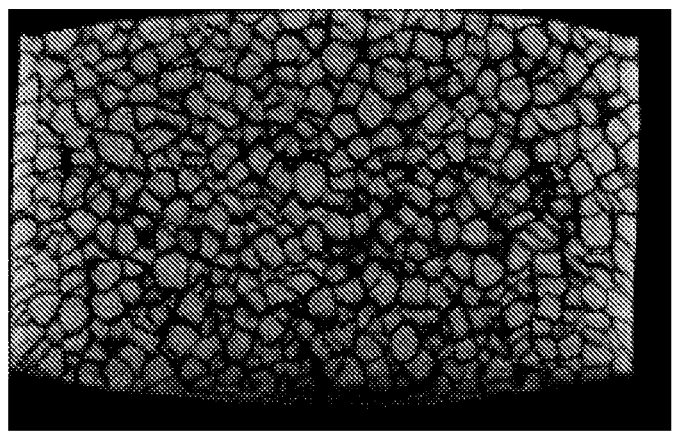
FIG. 13 is a photograph illustrating microcomputed tomography showing pore distribution in a PLGA scaffold.

A mixture of two distinct colored dyes, red and blue, were mixed with PLGA microspheres which were processed into layers thus, demonstrating distinct spatial compartments (FIG. 10). The shape and dimensions of the scaffolds described herein are useful for various applications including joint replacement, spinal defects, etc. The dimensions of each scaffold is defined by individual applications and configured (total size, ratio of tissue induction zones and interfaces and respective ratios) using material synthesis processes including 3D printing (Tables 2 and 3 of Arany P R & Mooney D J Oral Diseases (2011) 17, 241-251, incorporated herein by reference). Inter-pore continuity was assessed using Scanning Electron Microscopy (FIG. 11) and microcomputed tomography to validate a contiguous cell environment to allow cells to uniformly distribute throughout the system (FIG. 12). Validation of this system was performed using two separate biological approaches namely, reporter cells lines to visualize and confirm morphogen fields and stem cells for differentiation.

Representative Polymeric Systems

Most cells in the body require adhesion to the extracellular matrix for survival and function. As host cells are recruited in the programming approaches, the materials provide specific adhesion cues analogous to ECM to direct cell organization and regulate gene expression. Scaffolding materials are modeled on connective tissue and basement membrane components that support epithelial stratification, maturation and function. A wide range of natural polymers (e.g., collagens, fibrin, matrigel, alginate, chitosan, hyaluronate, silk, and polyhydroxyalkanoates) are used to mimic the ECM niche. These materials provide requisite physical support and allow natural tissue patterning and morpho-differentiation and this has been specifically demonstrated in regenerating pulp tissue (Bohl et al., 1998 J Biomater Sci, 9: 749-764; El-Backly et al., 2008 Aust Endod J, 34: 52-67). However, there are concerns of mechanical integrity, immune rejection and batch-to-batch variations. Another major limitation with these naturally derived polymeric systems is that complex cell-matrix interactions are not easily definable, making some of the biological responses unpredictable.

A variety of synthetic polymeric systems address the limitations of naturally derived materials, including controlled manufacturing at large scales and providing a precisely tailored cellular niche. Suitable synthetic polymer systems include poly(lactic) acid (PLA), poly(glycolic) acid (PGA), poly(lactic-co-glycolic) acid (PLGA), poly(ethylene glycol)-diacrylates (PEG-DA), poly(ε-caprolactone) (PCL), poly(ethylene glycol) terephtalate (PEGT), poly (butylene) terepthalate (PBT), polyphospho-esters (PPEs), polyphosphazenes (PPAs), polyanhydrides (PAs), polyortho-esters (POEs), and poly(propylene fumarate)-diacrylates (PPF-DA; Arany P R & Mooney D J Oral Diseases (2011) 17, 241-251).

Design Principles for Programmable Material Design

Polymeric materials with suitably designed chemistry not only define the cell-matrix interaction, but also aid in directing cellular responses by acting as depots to develop spatially restricted morphogen fields. Suitable design principles for programmable material design include the following. Biocompatible materials allow for minimal inflammatory and immune rejection, while controlled pore architecture allows for control over cell trafficking, morpho-differentiation, spatial organization, and host integration. Materials that encapsulate or bind soluble signaling molecules offer the advantage of spatiotemporal controlled delivery, while cell adhesive materials allow for cell attachment and promotion of interface-dependent cellular behavior. Materials with controlled biodegradation allow replacement by host tissue and avoid chronic host responses, while dynamic materials are responsive to local environment and/or external stimuli. Finally, gelable, injectable, or micro/nanoparticle materials allow for ease of delivery and minimal trauma.

Material Processing Techniques

Many techniques are routinely used to fabricate polymeric systems in a variety of geometries and architecture with precise control over pore size, shape and connectivity (Sohier et al., 2008 Expert Opin Drug Deliv, 5: 543-566). Spatially precise fabrication techniques have more recently been developed to provide better control of pore scaffold architecture, internal and external pore connectivity (Sohier et al., 2008 Expert Opin Drug Deliv, 5: 543-566). The conventional and newer techniques often involve the use of heat and solvents that can result in denaturation and loss of incorporated protein activity. One approach to overcome this limitation is by the use of two phase systems in which the polymeric fabrication step is decoupled from the biological incorporation step. Two common techniques used are addition of microspheres encapsulating proteins to a preformed scaffold or adsorption of the protein onto the polymer scaffold post-fabrication. In addition, processing techniques that utilize non-harmful solvents (such as $CO_2$, $H_2O$) allow biologically active molecules to be incorporated without diminishing their activity. Material processing techniques that allow for conventional architectures/geometry include fiber extrusion and electrospinning, heat bonding, gas foaming, phase separation, freeze drying, and particulate leaching. Material processing techniques that allow for more precise architectural control include fused diffusion molding, 3D fiber deposition, solid free form techniques, 3D printing, selective laser sintering, surface selective laser sintering, laser abalation, and stereolithiography.

Growth Factor Specific Reporter Cell Lines

Figure 14:
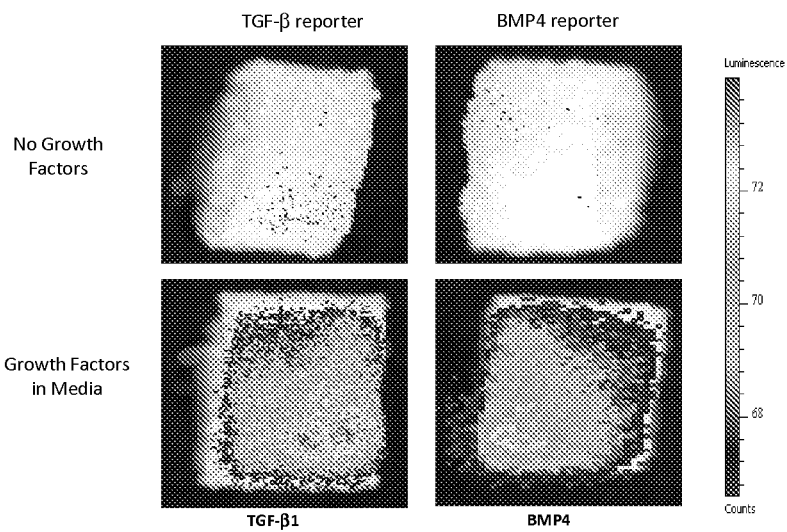
FIG. 14 is a series of photomicrographs showing multi-layered scaffolds seeded with either TGF-β reporter or BMP4 reporter in the absence of growth factors (upper panels) or in the presence of growth factors in media (lower panels). Luciferase activity was measured after 24 hours, and demonstrated a generalized induction of cell reporters.

Reporter cell lines demonstrate increased luciferase activity when exposed to specified growth factors. These cells were uniformly seeded within a regular PLGA scaffold (no layer, no incorporated growth factors) that demonstrates minimal luciferase activity when no growth factors are present (FIG. 14, top rows) or uniform activation throughout the scaffold when growth factor was added to the media allowing it to diffuse freely (FIG. 14, bottom rows).

Figure 15:
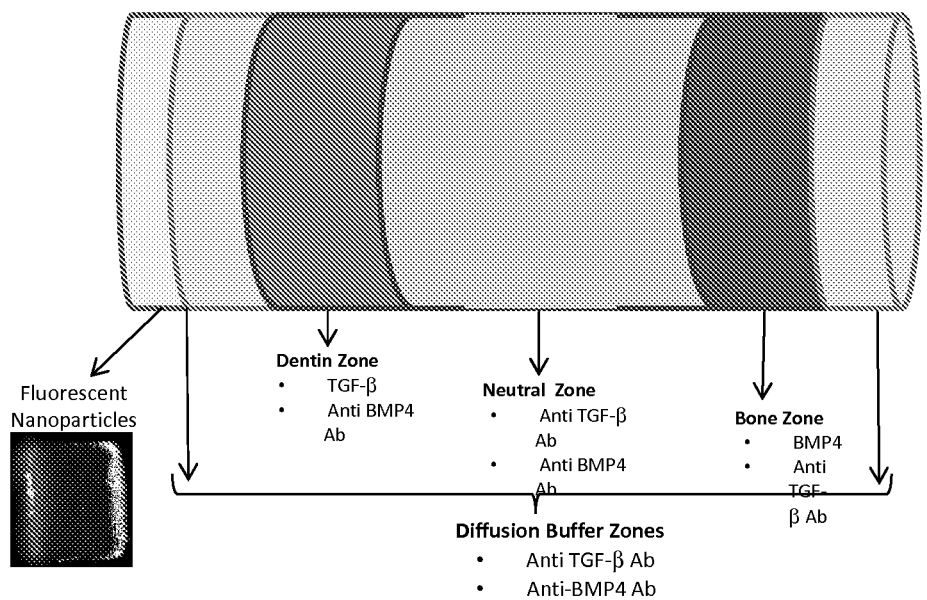
FIG. 15 is a schematic diagram of the Bone-Dentin layered scaffold design with distinct compartments containing growth factors and neutralizing antibodies.

Following testing with a 3 layered system that demonstrated a few design deficiencies, we developed a five layered scaffold system (FIG. 15) that had additional outer buffer zones that neutralize media diffused growth factors as well as fluorescent nanoparticles incorporated zone that enabled scaffold orientation due to the free floating nature of scaffolds in media during cell culture.

Figure 16:
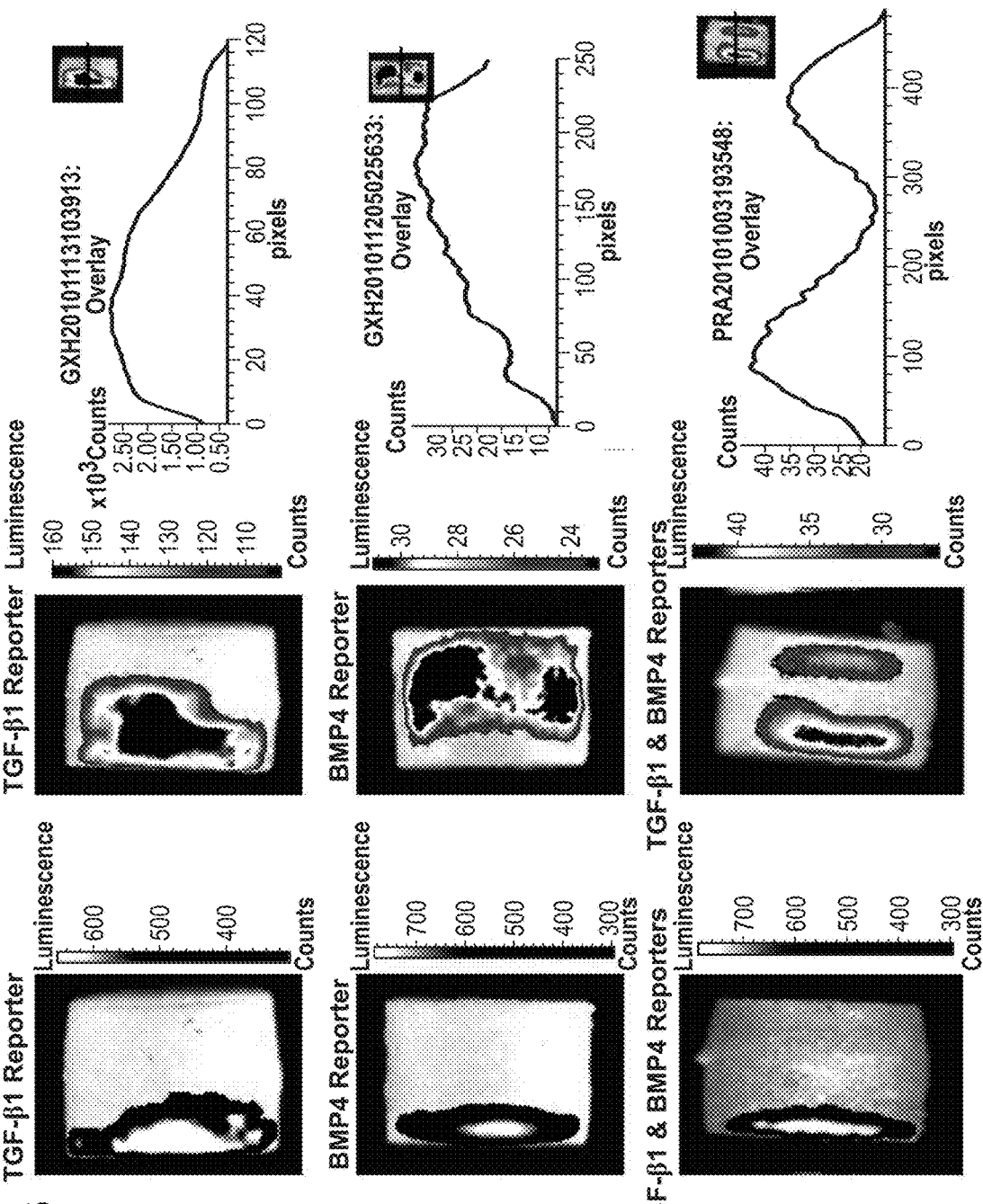
FIG. 16 is a series of photomicrographs and line graphs. The top row shows a multilayered scaffold seeded with the TGF-β reporter cell line. (MLEC p3TP Luc) illustrating spatially localized luciferase activity. The quantification of luciferase activity demonstrates a left spatial bias of luciferase activity representing the localized TGF-β inducing the reporter locally (top row). The middle row shows a multilayered scaffold seeded with the BMP4 reporter cell line (C2C12 BRE Luc) illustrating spatially localized luciferase activity. The quantification of luciferase activity demonstrates right spatial bias of luciferase activity representing the localized BMP-4 inducing the reporter locally (middle row). The bottom row shows a multilayered scaffold seeded with both the TGF-β reporter line (MLEC p3TP Luc) and the BMP4 reporter (C2C12 BRE Luc) illustrating two distinct zones of localized luciferase activity. The quantification of luciferase activity demonstrates the dual spatial zones of luciferase activity representing the localized TGF-B and BMP4 induction of the reporter cell lines locally (bottom row).

The reporter cell lines were seeded in these 5 layered systems and imaged for luciferase activity after 24 hours to confirm development of spatially distinct morphogens fields. The TGF-β reporter demonstrated activation of luciferase only in the defined left zone while BMP reporter line demonstrated the opposite orientation (FIG. 16). Seeding both cell lines in this system effectively demonstrated the ability to activate distinct growth factor signaling pathways in a spatially regulated manner.

The data demonstrated peak luciferase expression reflecting the spatially distinct morphogens fields that are developed by the 5 layered system and induced specific reporter activity in cell lines.

Directed Differentiation of Mesenchymal Stem Cells into Distinct Tissue Lineages To test the ability of the created morphogens fields with the scaffold system, the scaffolds were seeded with D1s, a Mesenchymal Stem Cell (MSC) cell line, which has been shown to be multipotent and can give rise to various differentiated tissue such as bone, fat, cartilage when provided with the appropriate cues. (Harnessing traction-mediated manipulation of the cell-matrix interface to control stem-cell fate. Huebsch N, Arany P R, Mao A S, Shvartsman D, Ali O A, Bencherif S A, Rivera-Feliciano J, Mooney D J. Nat. Mater. 2010 June; 9 (6):518-26.). Differentiation to dentin and bone was evaluated.

Figure 17A:
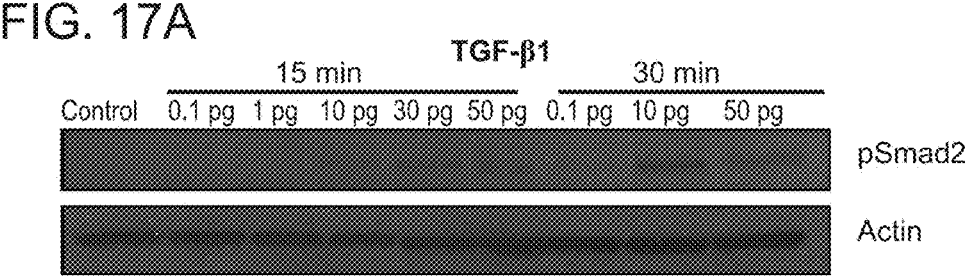
FIG. 17A is a photograph of an immunoblot for phospho-Smad2 to evaluate TGF-β responsiveness of D1 (MSCs) demonstrating a dose-dependent activation.
Figure 17B:
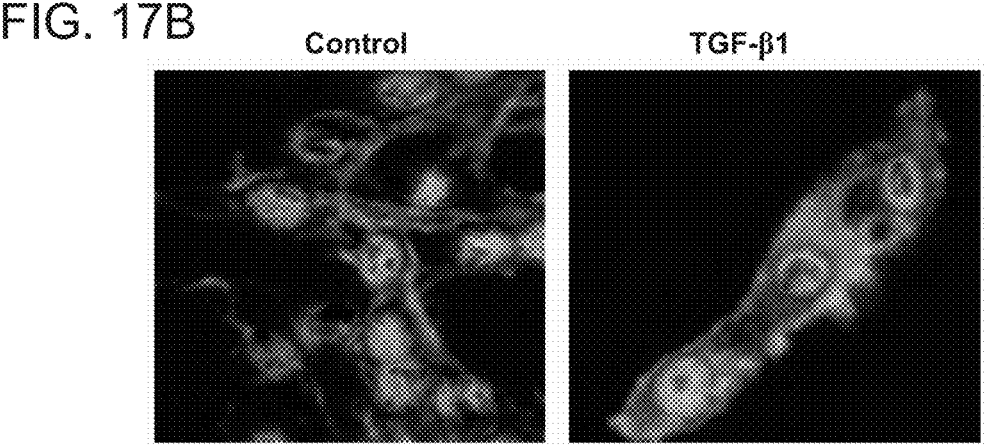
FIG. 17B is a photomicrograph showing immunostaining for phosphor-Smad2/3 to evaluate TGF-B responsiveness of D1 (MSCs) demonstrating nuclear localization of activated Smads following stimulation.

Experiments were carried out with the following morphogens: TGF-β1 to drive dentin differentiation and BMP4 to drive bone differentiation. The scaffold devices were fabricated, loaded with morphogens (in this case, differentiation factors), and then seeded with stem cells, e.g., mesendymal stem cells, embryonic stem cells or induced pluripotent stem cells (iPS)). The loaded, seeded devices were cultured for 21 days with no additional factors present in the media. All factors came from within the scaffold from the point of seeding. Immunoblots were carried out to assess activation of the downstream Smad signaling pathways following treatment of D1s with these morphogens. Robust activation was demonstrated, e.g., by phosphorylation of cytoplasmic intermediates in a dose dependent manner (FIGS. 17A and B).

Figure 17C:
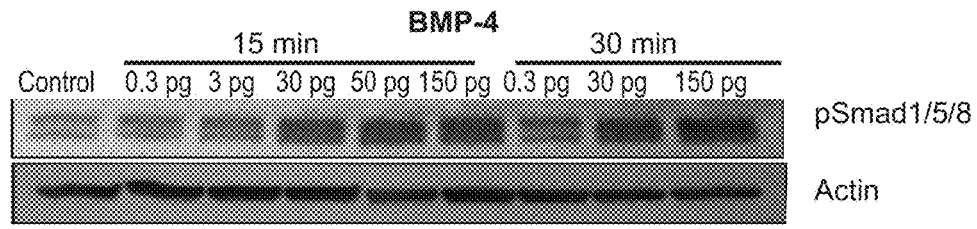
FIG. 17C is a photograph of an immunoblot for phospho-Smad1/5/8 to evaluate BMP4 responsiveness of D1 (MSCs) demonstrating a dose-dependent activation.
Figure 17D:
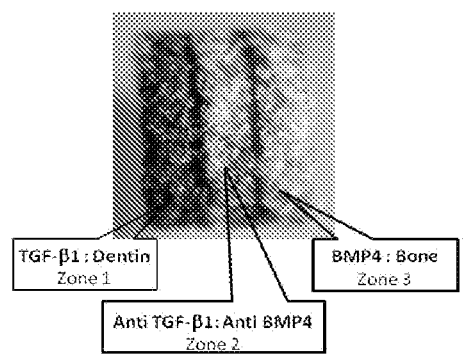
FIG. 17D is a photograph of a scaffold seeded with D1s for 21 days with twice weekly media changes. The scaffold was subsequently divided into three distinct zones for spatial analyses and lysed in RIPA, sonicated for 45 sec thrice and spun at 14000 rpm at 4° C. for 20 min to collect total protein.
Figure 17E:
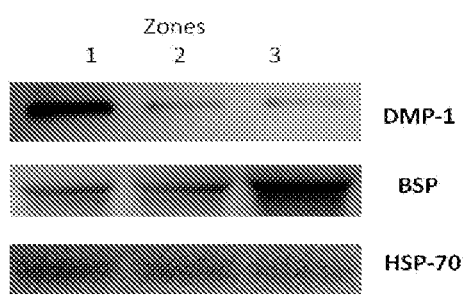
FIG. 17E is a photograph of an immunoblot of the protein extracted from the scaffold. Total protein was extracted and immunoassayzed for Dentin and Bone matrix markers illustrating spatially distinct differentiation into dentin and bone differentiation D1s.

To test the ability of the created morphogens field to direct mesendymal stem cell (MSC) differentiation, D1s were seeded into the scaffold systems. The cells were housed in the scaffolds for 21 days, changing the media twice weekly. Then the scaffold was divided into distinct zones as shown in FIG. 17C. Total protein was extracted and assessed by immunoblotting (FIG. 17D).

The results demonstrated the ability of the scaffold system to differentiate MSCs into specific lineages expressing matrix markers for bone (Bone Sialoprotein BSP) and Dentin (Dentin Matrix Protein-1) in a tightly regulated manner.

Spatial and Temporal Control System (Core-Shell Design)

Figure 18:
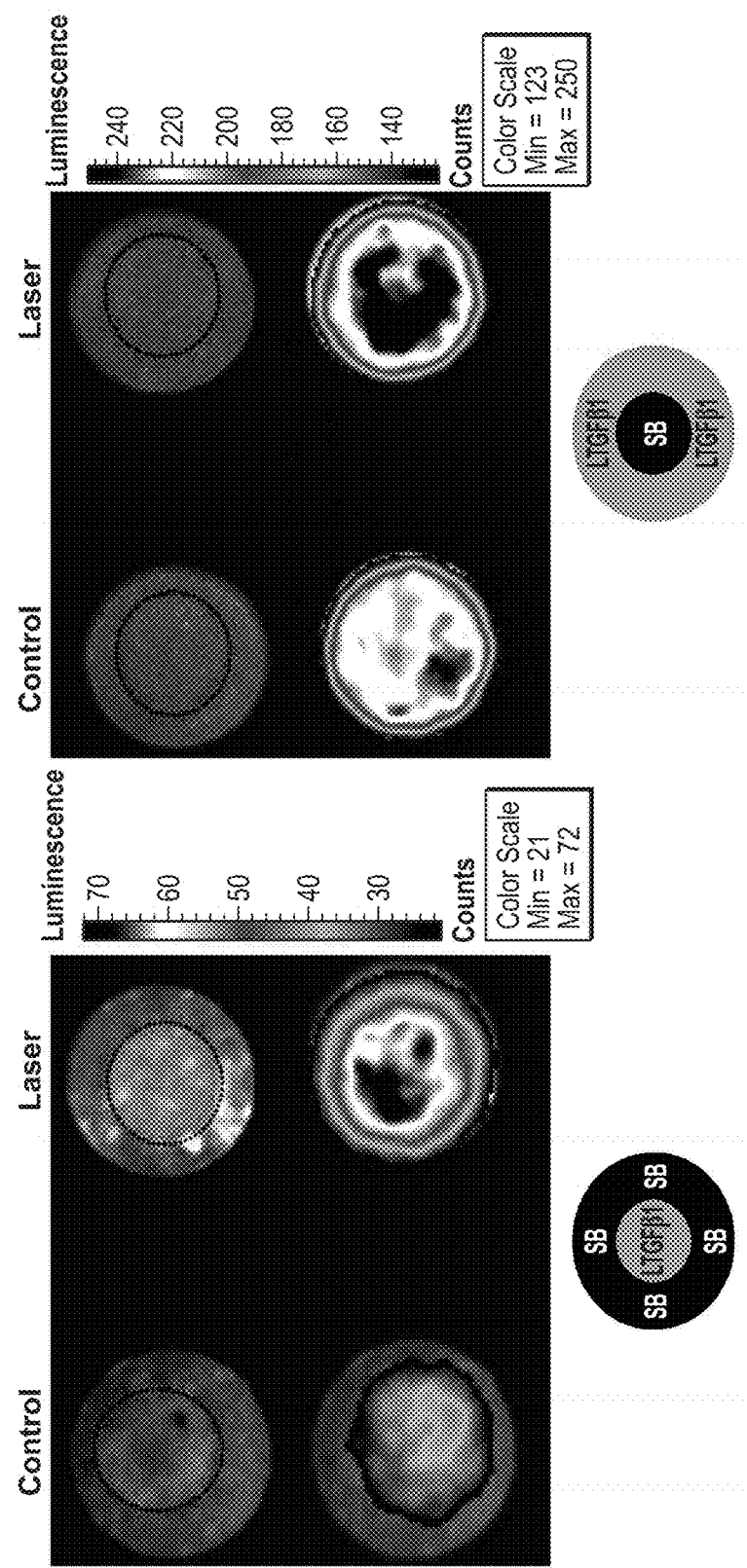
FIG. 18 is a photograph showing spatially restricted luciferase activity of TGF-β reporter cell line in another iteration of the scaffold design where a latent growth factor (TGF-β1) is encapsulated in either the core (left) or outer shell (right) and the small molecule inhibitor against TGF-β1 Receptor (SB431542) in the corresponding zone.
Figure 21A:
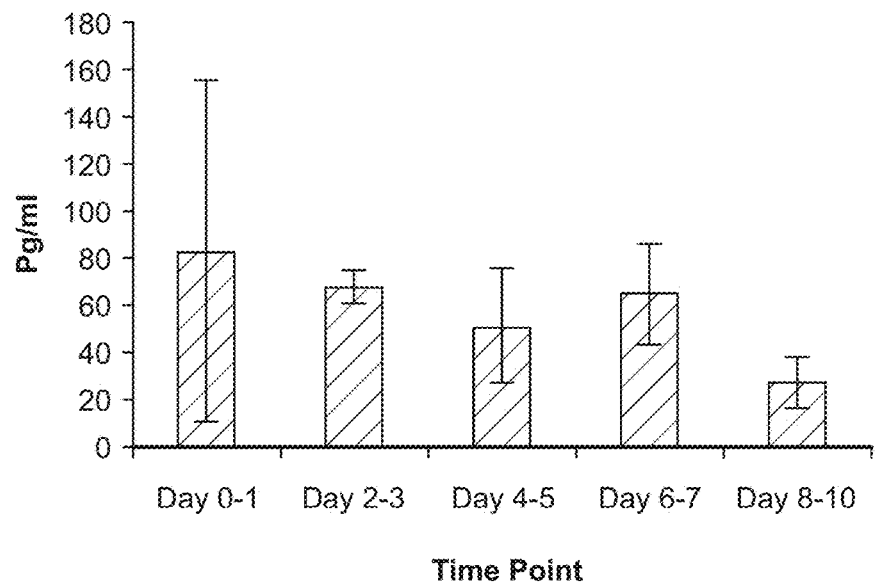
FIG. 21A is a bar graph showing the release of rhTGF-β1 measured with an ELISA over time in PBS at 37° C. from PLGA microspheres that were foamed into macro-porous scaffolds.
Figure 21B:
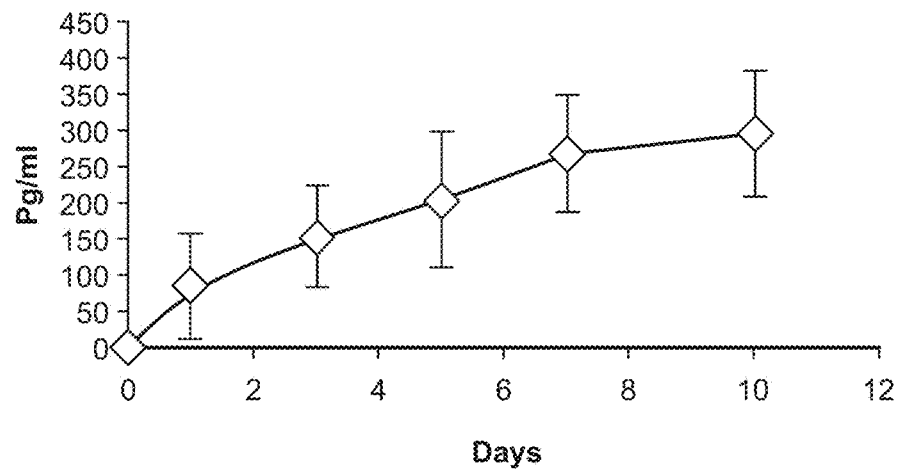
FIG. 21B is a line graph showing the calculated cumulative release of rhTGF-β1 from PLGA macro-porous scaffolds.
Figure 21C:
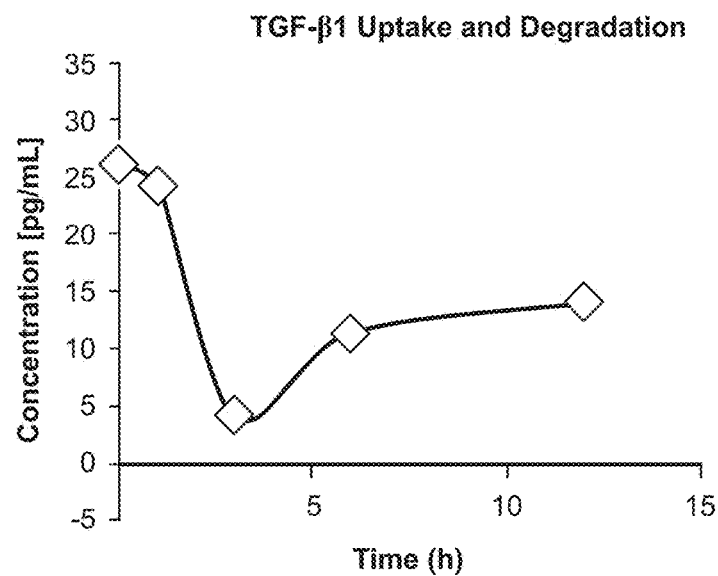
FIG. 21C is a line graph showing the half life estimation of rhTGF-β1 in culture dishes due to uptake and degradation determined by ELISA.
Figure 21D:
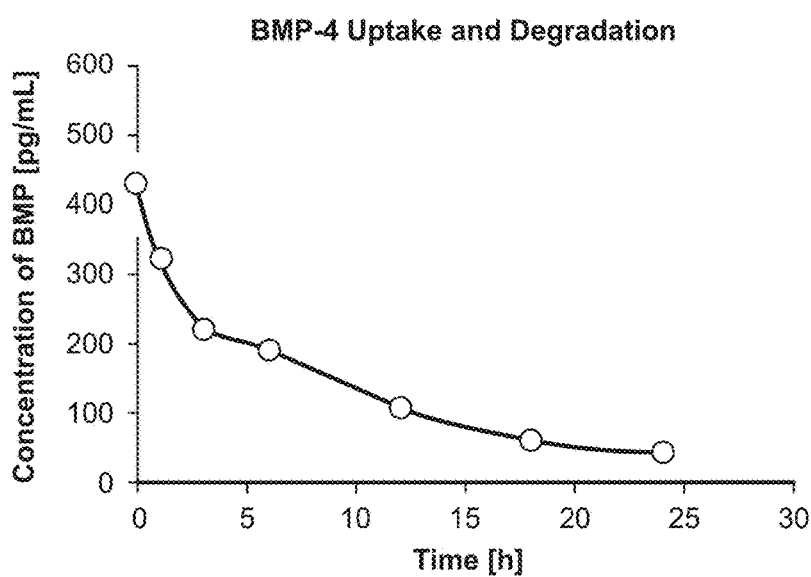
FIG. 21D is a line graph showing the half life estimation of rhBMP4 in culture dishes due to uptake and degradation determined with an ELISA.
Figures 21E, 21F:
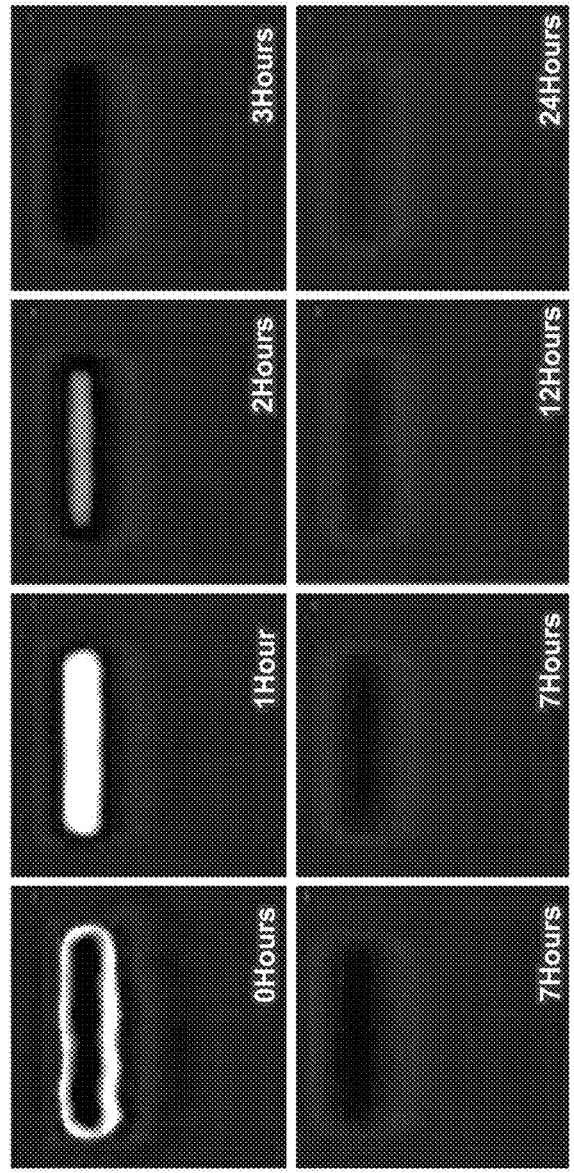
FIG. 21E is a series of formulas used to model release and uptake kinetics of growth factors and antibodies in COMSOL. The key assumptions used here were: (i) Complete/free mixing in media and 90% mixing within scaffolds; (ii) Antibody and protein-antibody degradation were assumed to be equal; (iii) the protein-antibody lifetime was considered infinite (no dissociation).
FIG. 21F depicts the release kinetics of a growth factor using COMSOL as modeled in FIG. 21E.

Another system involves a similar spatial segregation into a central 'core' and an outer 'shell' compartment that has a latent growth factor complex, Latent TGF-β1 (LTGF-β1), and a commercially available small molecule inhibitor (SB) that blocks its effects contained in them. Activation of the LTGF-β1 using specific parameters of laser irradiation (U.S. Ser. No. 61/449,249, incorporated herein by reference) permitted temporal control the onset of morphogen action. The utility of this system was demonstrated using the same reporter line described above. The data demonstrated the spatial and temporally regulated morphogens fields were generated to direct biological behavior (FIG. 18).

In the two variants of this system, the results demonstrated activation of the TGF-β1 pathway in a spatially defined manner indicating that the compositions and methods promote morpho-differentiation of tissue. For example, the scaffold systems promote differentiation of stem cells to a desired tissue type. In one example, a single cue and its corresponding inhibitor are used in the scaffold, but more complex systems with multiple cues that can be temporally controlled are manufactured and used in a similar manner. Such polymer-based scaffold systems use a biologically-inspired design and have been shown to provide distinct spatial and temporal cues to program cells, direct tissue organization and remodeling and ultimately define biological function.

Clinical Applications

Applications of the compositions and methods include: (1) Precision Engineering of Tissues and Organs that contain interfaces between distinct tissue types (e.g., engineering of joints, teeth, and spinal implants), and (2) in situ models to analyze biological mechanisms.

Precision Engineering Organs

With advance in tissue engineering approaches, it is now relatively simple to direct a single tissue differentiation to enable replacement or regeneration of diseased/destroyed tissue. The present system provides a powerful tool in defining two or more distinct tissue lineages from a homogenous population of cells, either recruited from host or externally provided along with the scaffold system. For example, current scaffold systems are able to either recruit or differentiate transplanted cells into bone or cartilage based on the delivery system. But prior to the invention, the production of specialized tissues constituting the joint are made of two juxtaposed specialized connective tissue was not achievable with conventional scaffold systems. The improved scaffold systems described herein recruit and differentiate host cells into two distinct lineages to regenerate the complex joint architecture and promote restoration of function (FIG. 19).

Another key application of this system is to drive cartilage and bone differentiation in vertebral defects as spinal implant systems. The differentiated cartilage, better than any synthetic inert material, provides the necessary mechano-elastic behavior that bone implants alone cannot provide effectively that is a key functional determinant of the clinical success in these applications (FIG. 20).

Many other such applications involving two differentiated tissue that need to be engineered juxtaposed to each other could benefit from this system design. Some examples are teeth (enamel and dentin, dentin and cementum, cementum and periodontal ligament), lung (respiratory epithelium and endothelium), liver (hepatocytes and sinus endothelium), kidney (glomerular filtration apparatus), cardiac valves (endocardium and myocardium), pancreas (β islets and a cells), among others. Suitable target tissues and corresponding morphogens for use in the scaffolds of the invention are provided in the table below. Exemplary inhibitors of the morphogens described herein include antibodies and small molecule inhibitors.

| Organ | Juxtaposed Tissue | Induction Ligand/Molecule |
|---|---|---|
| Teeth | Enamel | Ectodysplasin |
|  | Dentin | TGFβ1 |
|  | Cementum | Periostin |
|  | Periodontal ligament | BMP12 & 13 |
| Lung | respiratory epithelium | FOXM-1 |
|  | Endothelium | VEGF |
| Liver | Hepatocytes | FGF & HGF |
|  | sinus endothelium | VEGF |
| cardiac valves | Endocardium | TGF-β2 |
|  | Myocardium | VEGF, bFGF |
| Pancreas | β islets | Glucagon like Peptide1, NGF |
|  | Endotheloium | VEGF |
| Joints | Bone | BMP2, 4 or 7 |
|  | Cartilage | TGF-β3 |

In Situ Models to Analyze Biological Mechanisms

A significant limitation of current experimental approaches in the laboratory are either they are too simplistic cell culture and limited 3D culture systems or involve in vivo animal studies that are extremely complex, multiparametric systems. The described scaffold systems are useful as research tools. The scaffolds are used to build multi-tissue types and even critical functional organ systems on the bench allowing analyses of these intricate tissue interactions in vitro. Tissues constructed in this manner are used to analyze these systems as well as allow key perturbations to gain mechanistic insights into the biology of the tissues or organs. This provide a powerful tool to perform clinically relevant translational studies including disease modeling and therapeutic interventions.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for promoting cartilage regeneration, comprising:

contacting a target site of a subject with a device comprising a polymeric scaffold comprising a first and a second spatially distinct restricted zones, wherein the first zone comprises a purified morphogen that promotes cartilage regeneration, and wherein the second zone comprises a purified inhibitor of the morphogen;

wherein the morphogen and the inhibitor are released from the device into the target site;

wherein the morphogen promotes cartilage regeneration over a sustained period of time at a spatially restricted first region of the target site contacted by the first zone, thereby creating a field of action; and wherein the inhibitor inhibits the activity of the morphogen at a spatially restricted second region of the target site contacted by the second zone, thereby creating a boundary between the first region and the second region of the target site defining where cartilage regeneration is promoted.

2. The method of claim 1, wherein said morphogen is released at a first rate and said inhibitor is released at a second rate.

3. The method of claim 1, wherein the morphogen that promotes cartilage regeneration is a transforming growth factor-β (TGF-β).

4. The method of claim 3, wherein the TGF-β is selected from the group consisting of TGF-β1, TGF-β2, TGF-β3, and Latent TGF-β1 (LTGF-β1).

5. The method of claim 3, wherein the inhibitor is an anti-TGF-β antibody.

6. The method of claim 5, wherein the anti-TGF-β antibody is an anti-TGF-β1 antibody.

7. The method of claim 3, wherein the inhibitor is the small molecule inhibitor SB431542.

8. The method of claim 1, wherein the purified morphogen that promotes cartilage regeneration is Latent TGF-β1 and the purified inhibitor is the small molecule inhibitor SB431542.

9. The method of claim 1, wherein the morphogen is encapsulated within a microsphere.

10. The method of claim 1, wherein the inhibitor is encapsulated within a microsphere.

11. The method of claim 1, wherein the morphogen and the inhibitor are released from the device by diffusion.

12. The method of claim 1, wherein the polymeric scaffold comprises poly(lactic-co-glycolic) acid (PLGA).

13. The method of claim 1, wherein said device further comprises cells.

14. The method of claim 13, wherein said cells comprise mesenchymal stem cells, embryonic stem cells, or induced pluripotent stem cells.

15. The method of claim 1, wherein said device further comprises:
   a) a second purified morphogen, wherein the second purified morphogen promotes bone regeneration, and wherein the second purified morphogen is present in a spatially distinct restricted zone from the purified morphogen that promotes cartilage regeneration; and
   b) a second purified inhibitor, wherein the second purified inhibitor inhibits the activity of the second purified morphogen, and wherein the second purified inhibitor is present in a spatially distinct restricted zone from the second purified morphogen.

16. The method of claim 15, wherein the second purified morphogen is a bone morphogenetic protein (BMP).

17. The method of claim 16, wherein the bone morphogenetic protein is BMP4.

18. The method of claim 16, wherein the second purified inhibitor is an anti-BMP antibody.

19. The method of claim 18, wherein the anti-BMP antibody is an anti-BMP4 antibody.

20. The method of claim 1, wherein said method is performed in vivo.

21. A method of inducing cartilage regeneration in a spatially restricted region of a target site, comprising:
   contacting the target site with a device comprising a polymeric scaffold comprising a first and a second spatially distinct restricted zones, wherein the first zone comprises a purified morphogen that promotes cartilage regeneration, and wherein the second zone comprises a purified inhibitor of the morphogen;
   wherein the morphogen and the inhibitor are released from the device into the target site;
   wherein the morphogen promotes cartilage regeneration at a spatially restricted first region of the target site contacted by the first zone, thereby creating a field of action; and
   wherein the inhibitor inhibits the activity of the morphogen at a spatially restricted second region of the target site contacted by the second zone, thereby creating a boundary between the first region and the second region of the target site defining where cartilage regeneration is promoted, and inducing cartilage regeneration in a spatially restricted region of the target site.

22. The method of claim 21, wherein the morphogen that promotes cartilage regeneration is a transforming growth factor-β (TGF-β).

23. The method of claim 22, wherein the transforming growth factor-β is selected from the group consisting of TGF-β1, TGF-β2, TGF-β3, and Latent TGF-β1 (LTGF-β1).

24. The method of claim 22, wherein the inhibitor is an anti-TGF-β antibody.

25. The method of claim 24, wherein the anti-TGF-β antibody is an anti-TGF-β1 antibody.

26. The method of claim 22, wherein the inhibitor is the small molecule inhibitor SB431542.

27. The method of claim 21, wherein the morphogen is encapsulated within a microsphere.

28. The method of claim 21, wherein the inhibitor is encapsulated within a microsphere.

29. The method of claim 21, wherein the morphogen and the inhibitor are released from the device by diffusion.

30. The method of claim 21, wherein the polymeric scaffold comprises PLGA.

31. The method of claim 21, wherein said device further comprises cells.

32. The method of claim 31, wherein said cells comprise mesenchymal stem cells, embryonic stem cells, or induced pluripotent stem cells.

33. The method of claim 21, wherein the device further comprises:
   a) a second purified morphogen, wherein said second purified morphogen promotes bone regeneration, and wherein the second purified morphogen is present in a spatially distinct restricted zone from the purified morphogen that promotes cartilage regeneration; and
   b) a second purified inhibitor, wherein said second purified inhibitor inhibits the activity of the second purified morphogen, and wherein the second purified inhibitor is present in a spatially distinct restricted zone from the second purified morphogen.

34. The method of claim 33, wherein the second purified morphogen is a bone morphogenetic protein (BMP).

35. The method of claim 34, wherein the bone morphogenetic protein is BMP4.

36. The method of claim 34, wherein the second purified inhibitor is an anti-BMP antibody.

37. The method of claim 36, wherein the anti-BMP antibody is an anti-BMP4 antibody.

38. The method of claim 21, wherein said method is performed in vivo.

* * * * *